United States Patent
Eskandar et al.

(10) Patent No.: US 11,641,087 B2
(45) Date of Patent: May 2, 2023

(54) ACQUISITION OF INTERFEROMETRIC RECORDINGS OF BRAIN AND NEURON ACTIVITY BY COHERENT MICROWAVE PROBE WITH THERAPEUTIC ACTIVATION, INACTIVATION, OR ABLATION OF MOLECULAR, NEURONAL OR BRAIN TARGETS

(71) Applicant: Emad Eskandar, Swampscott, MA (US)

(72) Inventors: Emad N. Eskandar, Swampscott, MA (US); James Joseph Cohen, Wenham, MA (US)

(73) Assignee: Emad Eskandar, Swampscott, MA (US)

( * ) Notice: Subject to any disclaimer, the term of this patent is extended or adjusted under 35 U.S.C. 154(b) by 233 days.

(21) Appl. No.: 17/148,120

(22) Filed: Jan. 13, 2021

(65) Prior Publication Data
US 2021/0212764 A1   Jul. 15, 2021

Related U.S. Application Data

(60) Provisional application No. 62/961,263, filed on Jan. 15, 2020.

(51) Int. Cl.
  *H01S 1/04*   (2006.01)
  *H01S 4/00*   (2006.01)
  (Continued)

(52) U.S. Cl.
  CPC ............ *H01S 1/04* (2013.01); *A61B 18/1815* (2013.01); *A61B 90/36* (2016.02); *A61N 5/045* (2013.01);
  (Continued)

(58) Field of Classification Search
  CPC ... H01S 1/04; H01S 1/005; H01S 1/02; H01S 1/06; H01S 4/00; A61B 90/36;
  (Continued)

(56) References Cited

U.S. PATENT DOCUMENTS 3,283,147 A   11/1966  Avakian
9,042,413 B1   5/2015  Brown
(Continued)

FOREIGN PATENT DOCUMENTS

WO   2018026424   2/2018
WO   2019021002   1/2019
(Continued)

OTHER PUBLICATIONS

International Search Report dated Apr. 7, 2021 in co-pending PCT application PCT/US2021/013261.
(Continued)

*Primary Examiner* — Linda C Dvorak
*Assistant Examiner* — Abigail Bock
(74) *Attorney, Agent, or Firm* — Andrs Intellectual Property Law, LLP

(57) ABSTRACT

Low power MASER (Microwave Amplification by Stimulated Emission of Radiation) radiation is used to non-invasively record molecular activity in a biological object such as a brain. Low power MASER radiation is also used to neuromodulate molecular targets via Rabi coupling, resulting for example in conformational and function change in specific molecular targets such as ligand-gated ion channels, voltage-gated ion channels, G-proteins, or dopamine receptors. The method can be used to change the energy state of targeted molecules via energization or enervation, or to ablate targeted molecules.

8 Claims, 25 Drawing Sheets

(51) Int. Cl.
  *H01S 1/02* (2006.01)
  *H01S 1/00* (2006.01)
  *A61B 90/00* (2016.01)
  *A61B 18/18* (2006.01)
  *A61N 5/04* (2006.01)
  *H01S 1/06* (2006.01)
  *A61B 18/00* (2006.01)
  *A61N 5/02* (2006.01)

(52) U.S. Cl.
  CPC .............. *H01S 1/005* (2013.01); *H01S 1/02* (2013.01); *H01S 1/06* (2013.01); *H01S 4/00* (2013.01); *A61B 2018/0016* (2013.01); *A61B 2018/00446* (2013.01); *A61B 2018/00577* (2013.01); *A61B 2018/1861* (2013.01); *A61B 2090/374* (2016.02); *A61B 2090/3762* (2016.02); *A61N 2005/027* (2013.01)

(58) Field of Classification Search
  CPC .......... A61B 18/1815; A61B 2090/374; A61B 2090/3762; A61B 2018/0016; A61B 2018/00577; A61B 2018/1861; A61N 5/045; A61N 2005/027
  See application file for complete search history.

(56) References Cited

U.S. PATENT DOCUMENTS

| | | | |
|---|---|---|---|
| 9,966,720 | B2 | 5/2018 | Liu et al. |
| 2003/0098979 | A1 | 5/2003 | Dress et al. |
| 2006/0262876 | A1 | 11/2006 | LaDue |
| 2009/0287274 | A1 | 11/2009 | De Ridder |
| 2012/0289763 | A1 | 11/2012 | Boyden et al. |
| 2013/0335706 | A1 | 12/2013 | Schmitt-Manderbach et al. |
| 2015/0214687 | A1 | 7/2015 | Oxborrow |
| 2017/0367613 | A1 | 12/2017 | Eckert et al. |
| 2019/0117109 | A1 | 4/2019 | Grundfest et al. |
| 2019/0252842 | A1 | 8/2019 | Breeze et al. |

FOREIGN PATENT DOCUMENTS

| | | |
|---|---|---|
| WO | 2019202114 | 10/2019 |
| WO | 2019222436 | 11/2019 |

OTHER PUBLICATIONS

International Search Report dated Apr. 7, 2021 in co-pending PCT application PCT/US2021/013269.
International Search Report dated Apr. 6, 2021 in co-pending PCT application PCT/US2021/013279.
Breeze, et al. Continuous-wave room-termperature diamond maser, Mar. 22, 2018, vol. 555, Nature, pp. 493-500.
Gordon, et al. The Maser—New Type of Microwave Amplifier, Frequency Standard, and Spectrometer, Physical Review, vol. 99, No. 4, Aug. 15, 1955.
Hernandez-Lopez, et al. D1 Receptor Activation Enhances Evoked Discharge in Neostriatal Medium Spiny Neurons by Modulating an L-Type Ca2+ Conductance, The Journal of Neuroscience, May 1, 1997 17(9):3334-3342.
Hoppe, et al. Laser interstitial thermotherapy (LiTT) in epilepsy surgery, British Epilepsy Association, Feb. 16, 2017.
Mach, L. Via an interference refractory, March 1892 (machine translation included).
Maiman, T.H. Stimulated Optical Radiation in Ruby, Nature Aug. 6, 1960 vol. 187 pp. 493-494.
Schawlow, et al. Infrared and Optical Masers, Physical Review, vol. 112, No. 6, Dec. 15, 1958 pp. 1940-1949.
Wu, et al. Modeling the Pulse Signal by Wave-Shape Function and Analyzing by Synchrosqueezing Transform, May 26, 2016.

ACQUISITION OF INTERFEROMETRIC RECORDINGS OF BRAIN AND NEURON ACTIVITY BY COHERENT MICROWAVE PROBE WITH THERAPEUTIC ACTIVATION, INACTIVATION, OR ABLATION OF MOLECULAR, NEURONAL OR BRAIN TARGETS

FIELD OF THE INVENTION

This invention describes a process for utilizing low-power (2-10 Watts), coherent phase-locked anisotropic microwave emission, or MASER radiation, for non-invasively recording brain and general neuron activity and/or neuromodulation such as the energization/enervation of specific brain or axonal targets. The invention also can be used in the brain or other biological objects to image, activate, and inactivate targeted molecules for therapeutic purposes, or to disrupt targeted molecules so as to ablate tissue by causing cellular death.

BACKGROUND OF THE INVENTION

Neural Activity Recording and Neuromodulation: Single-unit recordings obtained using penetrating electrodes remain the "gold standard" for assaying in-vivo neural activity (Patel et al., 2013). This technique allows the isolation of action potential waveforms from individual cells and correlation of the neuronal firing to various brain processes. Historically, single unit recordings from anesthetized cats and from awake-behaving non-human primates have provided considerable insights (Hubel & Wiesel, 1968; Mountcastle, 1957). In humans, single unit recordings are obtained using tungsten micro-electrodes during surgery for placement of deep brain stimulating electrodes (30-90 minutes) and through microwire arrays that are occasionally used in epilepsy patients implanted with depth electrodes (1-2 weeks). In addition, arrays of silicon microelectrode are being experimentally implanted in quadriplegic patients to drive a cursor or a robotic arm. In each of these instances, electrodes are implanted into areas that are pathological and will be modulated (DBS), resected (Epilepsy), or are clearly without utility (motor strip of quadriplegic patients). This highlights a central challenge of using any invasive device at a large scale, which is how to justify the added risk to normal brain areas. Access to sulci, subcortical and medial/ventral areas is topologically difficult and perforce carries increased risk. Endovascular approaches can access certain area but carry other risks such as stroke. Chronic implantation incurs additional technical risks (signal instability, device breakage, and battery depletion) along with additional biological risks (inflammation and infection). Noninvasive imaging techniques such as functional magnetic resonance imaging (fMRI) have poor spatial and temporal resolution and cannot resolve activity at the level of single neurons.

Analysis of existing neuromodulatory techniques reflects similar issues. Deep brain stimulation (DBS) is the most precise and effective neuromodulatory technique, but—being invasive—carries risks and currently is reserved for the surgical treatment of intractable movement disorders. On the other hand, repetitive transcranial magnetic stimulation (rTMS) is a non-invasive neuromodulation technique that has been approved as a treatment in resistant depression and obsessive compulsive disorder. However, rTMS has a relatively low resolution and limited penetration in deep brain areas. Further, rTMS operates by generating induced electrical currents within the brain. The manner and degree in which these low frequency eddy currents dissipate is a relatively unreliable and unresolvable poly-mechanism and cannot be controlled. As the induced current is orthogonal to the coils used to couple the magnetic pulse, the inverse voltage induced in the axon will have an unknown effect. However, it is agreed that some effect is had.

The limitations of existing techniques provided the motivation for developing the current invention, which employs the use of room temperature, MASER technology. The use of coherent emissions is fundamentally different from other modalities. Coherent emissions can be used to interact with matter in a quantum manner. Hence, they are highly precise when used for measurement or recording purposes and surprisingly powerful when harnessed for certain effects. Applicant's system is designed to use a low-power (2-10 Watt) continuous wave MASER beam to "paint" a 3-dimensional activity map onto a structural map generated by 3-dimensional computer tomography (CT) or magnetic resonance imaging (MRI). This activity map is based on the interplay between a probe beam, resonant frequencies of molecules, and the interference patterns de-convolved when the probe beam with the reference beam are mixed.

Table 1A below lists a comparison of functional MRI, penetrating micro-electrode recordings and the disclosed system for coherent microwave interferometry.

TABLE 1A

| LARGE SCALE RECORDING | Functional MRI | Penetrating Micro-electrodes | Coherent Microwave Interferometry System |
|---|---|---|---|
| Signal | Blood Oxygenation | Action Potentials | Molecular Activity |
| Spatial Resolution | ~1 mm | 50 microns | 0.12 micron |
| Temporal Resolution | 500 ms | 1 ms | 10 nano sec |
| Whole Brain Recording | ✓ | x | ✓ |
| Cellular Level Recording | x | ✓ | ✓ |
| Noninvasive | ✓ | x | ✓ |

In another aspect, Applicant's system is designed to enervate signature molecular targets which in turn can be used for large scale therapeutic modulation. Table 1B below list a comparison transcranial magnetic stimulation, deep brain stimulation, and enervation through the disclosed coherent microwave therapeutic modulation system.

TABLE 1B

| LARGE SCALE MODULATION | Transcranial Magnetic Stimulation (TMS) | Deep Brain Simulation (DBS) | Coherent Microwave Therapeutic Modulation System |
|---|---|---|---|
| Mechanism | Magnetic Induction | Electrical Current | Resonant Coupling |
| Targeting Accuracy Precision | 1-2 cm Cortical Areas | 1-2 mm Subcortical Nuclei | 1 micron Molecular Changes |
| Whole Brain Neuromodulation | ✓ | x | ✓ |
| Targeted Neuromodulation | x | ✓ | ✓ |

TABLE 1B-continued

| LARGE SCALE MODULATION | Transcranial Magnetic Stimulation (TMS) | Deep Brain Simulation (DBS) | Coherent Microwave Therapeutic Modulation System |
|---|---|---|---|
| Excitation | ✓ | ✓ | ✓ |
| Enervation | x | x | ✓ |
| Noninvasive | ✓ | x | ✓ |

Electromagnetic Radiation (EMR): Visible light is part of the electromagnetic spectrum, which ranges from radio waves to gamma rays. Electromagnetic radiation waves, as their names suggest are fluctuations of electric and magnetic fields, which can transport energy from one location to another. Visible light is not inherently different from the other parts of the electromagnetic spectrum with the exception that the human eye can detect visible waves. Electromagnetic radiation can also be described in terms of a stream of photons which are massless particles each travelling with wavelike properties at the speed of light. A photon is the smallest quantity (quantum) of energy which can be transported. Electromagnetic radiation covers the range from radio waves to hard x-rays, which are also called gamma rays, see FIG. 1.

Interaction of EMR with Matter: The interaction of electromagnetic radiation (EMR) and matter is central to current imaging techniques and to the proposed technique. EMR is conveyed by photons. The frequency of a photon is proportionate to its energy:

$$E = h\nu = hc/\lambda$$

wherein E is energy, h is Planck's constant, v is frequency, c is the speed of light, and λ is the wavelength. Simply put, the higher frequency of the photon, the greater its energy.

Electromagnetic radiation interacts with matter through a limited number of mechanisms: transmission (including refraction and diffraction), reflection, absorption, or emission. Transmission implies that photons pass through a substance with minimal interaction, as is the case of visible light passing through a non-opaque gas. Refraction is a function of the different speeds with which electromagnetic radiation is transmitted through different substances, whereas diffraction describes its behavior as it passes through narrow apertures or around edges. Reflection describes the circumstance where an incident beam of electromagnetic radiation encounters a reflective surface such that the resultant beam has an angle equal to the incident beam. Absorption refers to a specific interaction between a photon and an atom or a molecule and emission refers to the discharge of a photon from an atom or a molecule.

At one end of the EMR spectrum are X-rays representing high-energy and high-frequency photons. Interaction of such a photon with an atom is associated with considerable energy transfer. If a photon in the x-ray band of the spectrum interacts with an atom, it causes an electron to be completely ejected from its shell, ionizing the host atom, disrupting its covalent bonds, and potentially damaging or breaking molecules including strands of DNA. At the opposite end of the spectrum are radio-waves, which are composed of low-energy, low-frequency photons. Photons in the radio-wave region of the spectrum generally have weak interactions with biological molecules and are transmitted through without change to either the photon or the molecules (FIG. 1).

Photons in visible light interact with biological molecules primarily through absorption and reflection. Visible light does not transmit through the body, meaning that photons are either reflected or absorbed. Reflected photons give rise to the color of biological tissues, whereas absorbed photons add kinetic energy, or heat, to biological tissues. Microwave emissions occupy a portion of spectrum between visible light and radio-waves and have properties of both. Depending on the frequency, microwaves can interact with biological molecules through, absorption and emission (as with visible light) or be transmitted (as with radio-waves).

Spontaneous Absorption and Emission: Quantum physics describes the behavior of atoms and electrons in relation to discrete quanta or packets of energy. Table 2 below provides definitions of a number of terms pertaining to quantum physics.

TABLE 2

| Term | Definition |
|---|---|
| Ground State | An atom with its electron(s) at their lowest orbital is said to be in its Ground State |
| Excited State | An atom in a higher energy state than its ground state reflecting electrons being in higher orbitals |
| Spontaneous Absorption | Electron transitions from lower energy to higher energy orbitals by absorption of photons and/or heat. |
| Spontaneous Emission | Electron transitions from higher energy to a lower energy orbitals by emission of photons and/or heat. |
| Stimulated Emission | Electron stimulation by photons to transition from higher to lower energy orbitals by emitting photons having the same frequency and phase as the incident photons. |
| Coherence | Photons having the same frequency and phase as generated in stimulated emission |

Electrons can absorb or release energy in the form of photons or heat. However, electrons are constrained to occupy discrete orbitals at specific energy levels. Electrons can transition from lower orbitals to higher orbitals through absorbing a photon with a frequency equal to the difference in energy between two orbitals in a process called "spontaneous absorption". Excited electrons relax back to their preferred lower energy levels by emitting photons having a frequency equal to the difference in energy between two orbitals through the process of "spontaneous emission" (Dirac & Bohr, 1927). Excitation into higher energy states can be only induced only by photons with the requisite frequency. Similarly, relaxation emits photons with specific frequencies corresponding to particular transitions.

Atomic and Molecular Transitions: The state of an electron can be described by four quantum numbers—the principal quantum number or orbital n (orbital), the azimuthal quantum number l (subshell), the magnetic quantum number m (magnetic moment) and the spin quantum number s. The energy of an electron is determined by its orbital and subshell. The Pauli exclusion principle states that no two electrons in an atom can have the same values for all four quantum numbers, though it is possible for electrons to have different quantum numbers but have the same energy levels, which are called degenerate orbitals.

Electrons can become excited and transiently occupy higher energy orbitals through the absorption of photons or heat. Relaxation of electrons can occur through radiative decay with the emission of photons, or through non-radiative decay with the emission of heat.

At the level of atoms, spontaneous absorption can occur with photons frequencies in the ultraviolet, visible, and infra-red range of the spectrum. Electron relaxation may occur through a series of smaller steps associated with emission of photons with lower energy and frequency including those in the microwave range. The energy of an atom is also a quantum state and reflects the quantum states, as defined by the four quantum numbers, of all its constituent electrons. Molecules have additional degrees of freedom, beyond the four quantum numbers, that are described as molecular vibration and rotation. Transitions between these states are also quantal and generally occur through the absorption and emission of photons with frequencies in the infra-red or microwave range.

Transitions between different quantum energy states can be represented using Jablonski diagrams. An atom or molecule in the lowest energy state possible, known as the ground state, can absorb a photon with a specific frequency whereby it becomes excited and attains a higher energy state FIG. 2A. A substance made of such atoms will absorb this characteristic frequency, and likely other specific frequencies associated with other transitions, thereby imparting its color. The atom or molecule tends not to stay in this excited state and can relax back to its ground state in several ways. In FIG. 2A, the atom or molecule relaxes in two quantum steps, through an intermediate quantum state, and emits two photons both of which have lower frequency and energy than the absorbed photon. The photons emitted will be characteristic for the energy transitions appropriate for that particular atom or molecule, and by studying the light emission the matter under investigation can be determined.

In FIG. 2B, the excited atom or molecule initially loses energy not emitting a photon but by a nonradiative process (heat) emission, to reach an intermediate state. The atom or molecule then relaxes from the intermediate energy state to the ground state by the emission of a lower energy photon than originally absorbed. A uniform collection of atoms or molecules can relax through a combination of mechanisms, the distribution of which depends on the lifetime of the different intermediate states and external factors such as magnetic fields.

Stimulated Emission: The fundamental idea behind the process called "stimulated emission" was first described in 1917 as part of a more extensive paper by Albert Einstein on "The Quantum Theory of Radiation" (Einstein, 1917). In stimulated emission, an excited electron is stimulated by an incident photon, not into a higher orbital but rather into a lower orbital (FIG. 3). In this case, the incident photon is not absorbed, but rather just induces the excited electron back into its preferred lower-energy ground or state (loosely analogous to just touching a ball perched on top of a wall so it falls to the ground). This downward transition of the electron results in the emission of a photon. Initially, there are two quanta—the excited electron and the incident photon. Subsequently, there are also two quanta—the incident photon and the emitted photon. Hence, energy is conserved. Critically, however, after the encounter both the incident photon and the emitted photon, having been transiently enmeshed, emerge having the same phase and frequency. Thus, there are three important features to this process. 1) Before emission, the incident photon has a frequency equal to the difference in energy between the excited state and the lower energy state. 2) After emission, both the incident and emitted photon are coherent, having the same frequency, phase, and direction. 3) The process starts with one photon having the requisite frequency to generate an emission and ends with two photons having the necessary frequency to evoke an emission. These two coherent photons can stimulate other atoms potentially leading to 4 coherent photons, which could lead to 8 coherent photons etc.

Hence, under the right circumstances and with an appropriate source of energy, this process can be optimized so it becomes self-reinforcing or multiplicative. Upon reaching a population inversion into a metastable state, the lasing or masing threshold, this process creates a surfeit of coherent photons having the same frequency (monochromatic in the case of lasers), phase, and direction—a LASER beam for visible light or—a MASER beam for microwaves. Such beams have unique properties and applications that cannot be realized with incoherent light or microwave radiation, which has a mixture of frequencies, phases, and directions.

Devices for Creating Coherent Emissions: In 1955, American physicist Charles Townes of Columbia University, an expert in molecular spectroscopy, and his co-workers, showed how stimulated emission could be used to make a device for generating coherent microwave emissions, which they called a MASER (Microwave Amplified Stimulated Emission of Radiation) (Gordon et al., 1955). Three years later. Townes and Arthur Schwalow explained how to extend the idea to visible and infrared frequencies and make an "Optical MASER", a name later changed to LASER—L for visible light (Schawlow & Townes, 1958). Their ideas were subsequently realized with the demonstration of a functional laser by Theodore Maiman at Hughes Research Laboratories in 1960 (Maiman, 1960). Since then, there has been an increase in sophistication surrounding the design, fabrication, and use of coherent emissions in the visible region of the EMR spectrum.

There are many important steps in the practical implementation of a successful system. The first is to identify a substance having favorable quantum transitions, either on theoretical or empirical grounds. This substance is called the gain medium. Identification and selection of the gain medium entails several considerations: 1) The substance must have suitable transition states that can be stimulated at the desired frequency. 2) Useful transitions are commonly associated with frequencies in the visible, infra-red or microwave range. 3) The sequence of transitions can be complex, and a limited number of substances may be suitable for stimulated emission. 4) Favorable substances may relax through a particular sequences of state transitions including a ground state, an excited state, and a metastable excited state that on-average takes longer to relax back to the ground state than competing states.

Once a suitable gain medium is identified, the next practical step is to establish the process of stimulated emission by providing the energy necessary to establish and drive the process. This energy is usually provided in the form of photons, a process called photon-pumping. Photons can be provided by a laser, a light-emitting diode (LED), or other means. The next step is to create conditions that preferentially enrich the metastable state so that stimulated emissions overtake spontaneous emissions as the predominant process. This may involve using electrical fields, magnetic fields, or a means for promoting resonance in the desired frequency using a resonator box (Laser systems have mirrors while MASERs have a physical cavity). Finally, it is important to consider whether the system should be designed to have a constant but lower output (Continuous Wave) or higher but periodic outputs (Pulsed Wave) (Wu et al., 2019).

Until recently, solid-state MASERs have been large devices with low efficiency and considerable heat generation, necessitating cryogenic cooling to sustain continuous wave (CW) operation. Hence, their utility was limited to certain applications. For example, hydrogen MASERs have been used as atomic frequency standards (Bauch, 2007). In other applications, the Jet Propulsion Laboratory developed a MASER to provide amplification of microwave signals from deep space probes (Reid, 2008).

Recent Advances in MASER Technology: In 2018, it was demonstrated that a room temperature, continuous wave MASER was achievable using bulk synthetic diamonds containing specifically engineered lattice defects (Breeze et al., 2018). A laser was used to pump photons into nitrogen-vacancy defects within the diamond matrix. That paper described an experimental benchtop MASER, essentially a single emitter, housed in a large copper resonator box, not a design suitable for commercial manufacture nor in large flat panel arrays. On May 8, 2018 Renbao Liu, and Liang Jin from the Chinese University of Hong Kong, were issued U.S. Pat. No. 9,966,720. This patent describes a system and a method for coherent emission of continuous wave MASER beams from a bulk diamond crystal gain medium having nitrogen vacancy centers. The system in '720 patent uses optical pump energy within a moderate magnetic field and describes a MASER or amplifier functioning at room temperature (15° C.-50° C.) in the continuous-wave mode. The gain medium is bulk diamond single crystal, with the emitters nitrogen-vacancy (NV) centers in the diamond.

Since the potential for a room-temperature MASER has only recently been realized, there is little prior art on the commercial manufacture of MASER emitters. In contrast, there have been tremendous commercial, industrial, medical, and scientific advances in lasers, which are informative and reviewed below.

Co-pending application Ser. No. 17/148,215 entitled "Thin Film MASER Emitter and Thin Panel Phased Array of Emitters," by James Joseph Cohen and Emad N. Eskandar, filed on even date herewith and incorporated by reference, describes a unique combination of thin epitaxial diamond film implanted with nitrogen ions in combination with other component layers to enable the fabrication of a thin panel, phased-array of MASER emitters. The present invention preferably uses the thin panel of phased array of emitters described in Applicant's co-pending application Ser. No. 17/148,215, entitled "Thin Film MASER Emitter and Thin Panel Phased Array of Emitters," by James Joseph Cohen and Emad N. Eskandar.

The relevant metastable state in the nitrogen-vacancy (NV) centers has a lifetime of ~1.6 microseconds, sufficient for generating continuous wave, mode-locked MASER emissions, but unlikely to generate transients or other undesirable effects.

Continuous Wave Lasers: Continuous-wave lasers produce a continuous, uninterrupted beam of light, ideally with a very stable output power. The exact wavelength(s) or line(s) at which this occurs is determined by the characteristics of the laser medium. For example, $CO_2$ molecules readily lase at 10.6 μm, while neodymium-based crystals (like YAG or vanadate) produce wavelengths in the range between 1047 and 1064 nm. Each laser wavelength is associated with a linewidth, which depends on the gain bandwidth of the lasing medium and the design of the optical resonator. The ideal laser would produce only one wavelength, however, even a single laser line actually covers a range of wavelengths. For example, laser diodes produce light over a wavelength range of several nanometers corresponding to their "gain bandwidth." The specific wavelengths of the output beam within this gain bandwidth are determined by the longitudinal modes of the resonant cavity, and the actual output wavelengths of the laser will correspond to longitudinal cavity modes that fall within the gain bandwidth.

Pulsed Lasers: Pulsed laser devices produce trains of very brief emissions lasting 0.5 to 500 ns. The most important characteristic of a nanosecond-pulsed laser is the capability to "store" and release energy very rapidly, on a nanosecond scale, so that the laser output can achieve kilowatts to megawatts of peak power. Materials such as excited dimers (or "excimers") of a noble gas with a halogen, such as Ar:F and Xe:Cl, sustain laser action for only several nanoseconds and can only be used for pulsed operation. Some lasers, like Nd or Yb diode-pumped solid-state (DPSS) lasers, can be used in either continuous wave or pulsed operation, while other lasers are not suitable for any pulsed operations. The key to producing these energetic pulses is storing energy from the pump in the atoms or molecules of the lasing medium by preventing the laser gain and the amplification process. Then, when the stored energy is at its maximum, lasing action is rapidly enabled.

Q-Switching: A Q-switch is essentially a means of spoiling or disrupting the light path within the resonator, with a very fast response time. Q is shorthand for quality, in this case the quality of the cavity or of light transmission. Hence in one state (low Q) the switch creates cavity loss, poor quality of resonance, and prevents lasing; in the other case (high Q), there is essentially no loss, so lasing can occur. The most commonly used Q-switch devices for lasers are electro-optic (EO) and acousto-optic (AO) modulators. In EO modulators, a crystal rotates the polarization of light passing through it when a voltage is applied, and disrupts lasing. In an AO modulator, a crystal deflects the intracavity beam by a fixed angle when radio frequency (RF) power is applied, also disrupting lasing.

Mode-Locking: Laser materials with a wide gain-bandwidth, such as Titanium/Sapphire, $TiAl_2O_3$ can produce a broadband frequency output (tens of nanometers of more). Detailed examination reveals that this output consists of hundreds, thousands, or even tens of thousands of individual longitudinal modes. These modes gain and lose intensity and have random phase relationships relative to each other. In mode-locking, the relative phase of all these modes is fixed. There are two categories of mode-locking called active and passive mode-locking. Active mode-locking entails fast gating of the cavity (for example, by using an AO modulator as in the Q-switching). Passive mode-locking is performed through materials that change their properties in response to the generation of mode-locked emission. One technique uses a "bleachable" optic, essentially a special mirror within the cavity that approaches 100% reflectivity when its absorbing semiconductor layer is overloaded by the high peak power of mode-locked operation.

Coherent Synthetic Aperture Detection: In a typical flat-panel detector array, the elements are strictly arranged in two dimensions—similar to tiles on a floor. In contrast, synthetic aperture/interferometric imaging information is derived by correlating intensity and phase information from groups of detectors. For N detectors, there are $N(N-1)/2$ detector pairs corresponding to $N(N-1)/2$ pixels in a reconstructed image. Hence, unlike typical arrays where the number of detectors equals the number of pixels, the number of pixels increases by the square of the number of detectors, meaning that fewer detectors and faster frame rates are possible for a desired resolution compared with either a raster-scan or an N detector focal plane array. However, it is necessary to correlate evaluations from different groups of detectors in order to realize this advantage, which entails aperiodic and/or multidimensional detector arrangements.

As an example, consider the two types of arrays for imaging with a set resolution at a given distance using the same number of detectors and a fixed area corresponding to an even number of arbitrary pixels. For the sake of this math that number shall be set to be 1596. The number of detectors is chosen to be N=57, so that the number of pixels in the image is the same for both the focal plane array image (with scanning) and the interferometric imaging method. The focal plane array, at a rate of 57 pixels per scan, would need 28 scans to cover the entire area. In this estimate, it is assumed that the time to digitize or acquire the data from each detector is the same for both the interferometric and the focal plane array approach. This is a reasonable assumption, for example, if the same or comparable detectors are used for both the approaches and the correlation calculations are not a rate-limiting step. The interferometric imaging array can record the entire image with one scan. However, there is a tradeoff—1596 correlations are needed to reconstruct the interferometric image. This correlation hardware requirement is not necessary with a focal plane array. In essence, one is trading imaging speed for backend image processing.

If there is no time restriction to generate an image, one can reduce the required number of detectors for interferometric imaging accordingly. For example, if the aperiodic interferometric array is angled, the equivalent number of pixels in the reconstructed image is M*N (N−1)/2 where M is the number of unique rotational positions of the array. Assuming 28 different rotation positions for the interferometric array, the corresponding time to acquire an image would be the same for both the techniques. However, to maintain the number of pixels at 1596, only 11 detectors are required in the interferometric approach compared with 57 for the focal plane array. This reduction in the number of detectors reduces the required number of correlations from 1596 to 55. Thus, if there are technical limitations or difficulty in fabricating focal plane detector arrays with a large number of detectors, synthetic aperture approaches, such as interferometric imaging, can reduce the number of required detectors while maintaining the same number of image pixels.

Synthetic-Aperture Imaging (SAI) is a form of imaging that is used to create two-dimensional images or three-dimensional reconstructions of objects. SAI uses the motion or the dimensional displacement of the detector over a target region to provide finer spatial resolution than conventional array or detector scanning. SAI detectors are typically mounted on a moving platform, such as an aircraft or spacecraft. The technology has its origins in an advanced form of side looking airborne radar (SLAR). The distance the SAI device is displaced or travels over a target in the time taken for the radar pulses to return to the antenna creates the large synthetic aperture (the size of the detector). Typically, the larger the aperture, the higher the image resolution will be, regardless of whether the aperture is physical (a large detector) or synthetic (a moving detector array)—this allows SAI to create high-resolution images with comparatively small physical or 2-dimensional detector arrays. Additionally. SAI has the property of having larger apertures for more distant objects, allowing consistent spatial resolution over a range of viewing distances.

To create a SAI image, successive pulse trains are transmitted to "illuminate" a target, and the convolved mixed interferometric beam is received and recorded. The beams are transmitted, and the convolved beams are received using single beam-forming mixers. As the SAI device is scanned, the detector relative to the target changes with time. Signal processing of the successive recorded pulse trains allows the combining of the recordings from these multiple detector positions. This process forms the synthetic antenna aperture and allows the creation of higher-resolution images than would otherwise be possible with a given 2-dimensional static array. SAI is capable of high-resolution remote sensing, as SAI can select frequencies to avoid signal attenuation. SAI has continuous imaging capability as illumination is provided by the Synthetic Aperture emitter.

Synthetic Aperture images have wide application in remote sensing and mapping. Applications of SAI include topography, oceanography, glaciology, geology (for example, terrain discrimination and subsurface imaging), and forestry, including forest height, biomass, deforestation. Volcano and earthquake monitoring use differential interferometry to detect subtle changes in elevation. SAI can also be applied for monitoring civil infrastructure stability such as bridges. SAI is useful in environment monitoring such as oil spills, flooding, urban growth, global change and military surveillance, including strategic policy and tactical assessment. SAI can be implemented as inverse SAI by observing a changing or moving target over a substantial time with a stationary antenna.

A synthetic-aperture detector is an imaging system mounted on a moving platform, or on a 3-dimensional detector array accessible in a temporally regular fashion. Electromagnetic waves are transmitted sequentially, the modulated beam, scatters or echoes are collected, and the system stores the data for subsequent processing. As transmission and reception occur at different times, they map to different positions. The well-ordered combination of the received signals builds a virtual aperture that is much larger than the physical detector array. That is the source of the term "synthetic aperture," giving it the property of an imaging system. The range direction is parallel to the 3-dimensional offset and perpendicular to the azimuth direction.

Basic principle: The 3-dimensional processing is done in two stages. The azimuth and range direction are focused for the generation of 2-dimensional (azimuth-range) high-resolution images, after which a digital elevation model (DEM) is used to measure the phase differences between complex images, which is determined from different look angles to recover the height information. This height information, along with the azimuth-range coordinates provided by 2-dimensional SA focusing, gives the third dimension, which is the elevation. The first step requires only standard processing algorithms. The second step requires additional pre-processing such as image co-registration and phase calibration.

In addition, multiple baselines can be used to extend 3-dimensional imaging to the time dimension. Four-dimensional and multi-dimensional SAR imaging allows imaging of complex scenarios and has improved performance with respect to classical interferometric techniques such as persistent scatter interferometry. Co-pending application Ser. No. 17/148,275 entitled "Phased-Array MASER Detector for Synthetic Aperture Interferometric Imaging," by James Joseph Cohen and Emad N. Eskandar, filed on even date herewith and incorporated by reference herein, describes a phased array of detector elements, for example Schottky detector diodes with sufficient sensitivity to reliably detect and reflect different values of MASER emissions. The detectors are arranged in layers offset in three dimensions. The phased-array MASER detector is particularly useful for detecting characteristics in a biological object using low energy (2-10 Watts), coherent MASER radiation.

The SAI algorithm, as given here, generally applies to phased arrays.

A three-dimensional array (a volume) of scene elements is defined, which will represent the volume of space within which targets exist. Each element of the array is a cubical voxel representing the probability (or "density") of a scattering surface being at that location in space.

Initially, the SAI algorithm gives each voxel a density of zero. Then for each captured waveform, the entire volume is iterated. For a given waveform and voxel, the distance from the position represented by that voxel to the detector(s) used to capture that waveform is calculated. That distance is represented as time delay of the waveform. The sample value at that position in the waveform is then added to the voxel's density value. This represents a possible signal from a target at that position. Note there are several optional approaches here, depending on the precision of the waveform timing, among other things. For example, if phase cannot be accurately determined, only the envelope magnitude (with the help of a Hilbert transform) of the waveform sample might be added to the voxel. If waveform polarization and phase are known and are sufficiently accurate, then these values might be added to a more complex voxel that holds such measurements separately.

After all waveforms have been iterated over all voxels, the basic SAI processing is complete. What remains, in the simplest approach, is to decide what voxel density value represents a solid object. Voxels whose density is below that threshold are ignored. Note that the threshold level must be higher than the peak energy of any single wave, otherwise that wave peak would appear as a sphere (or ellipse, in the case of multistate operation) of false "density" across the entire volume. Thus, to detect a point on a target, there must be at least two different antenna echoes from that point. Consequently, there is a need for large numbers of detectors positions to properly characterize a target. The voxels that passed the threshold criteria are visualized in 2D or 3D. Optionally, added visual quality can sometimes be had by use of a surface detection algorithm like marching cubes.

Synthetic Aperture via Phased Array Control: Provided that the wave propagating emitter is stable and controllable, the well-established principles of Phased array beamforming may be utilized to synthesize a diffraction limited MASER beam with a determinate numerical aperture.

Since the MASER emitters emit diffraction limited energy isotropically, it is necessary to synthetically create a wave front that has selective directionality and mode locked character adequate for the contemplated pass length. Regardless of the source, the principles underlying wave addition may be applied.

Shifted emission phased array principles have been widely used in radar, sonar, seismology, oceanology, and medical imaging. Simply stated, a "phased array" is a group of emitters or sensors located at distinct spatial locations in which the relative phases of the signals are varied in such a way that the overall gestalt propagation mode is reinforced in a selectable direction and deconstructed in all other directions. The phased array principles have allowed the development of emitter and detector assembly's that can beam form and beam steer without any mechanical control.

Phased arrays can act as both wave transmitters (emitters) and wave receivers (detectors). When a phased array works in transmission mode, the relative amplitude of the signals radiated by the array in different directions determines the effective radiation pattern of the array. In practice, a phased array may be used to point toward a fixed direction, or to scan rapidly in azimuth or elevation.

The array acts as a spatial filter, attenuating all signals except those propagating in certain directions. "Beamforming" is the name given to a wide variety of array-processing algorithms that are used to focus the array's signal-receiving or signal-transmitting abilities in a particular direction. A beam refers to the main lobe of the directivity pattern. Beamforming can apply to transmission from the array, to reception in the array, or to both. A beamforming algorithm points the array's spatial filter toward desired directions. This is similar to the dish antenna of conventional radar swiveling to steer its beam into a desired direction; however, the phased-array beam-steering is achieved algorithmically rather than physically. The beamforming algorithm generally performs the same operations on the sensors' signals regardless of the number of sources or the character of the noise present in the wave field.

A phased array system requires fine frequency and phase coherence to a specific and stable operating mode. That may be achieved by a variety of means or by the use of a coherent emitter such as a MASER. Symbolically all phased arrays of any integer plurality of emitters (N) is an example of N-slit diffraction provided that the EMR field at the detection point is a consequence of the coherent addition of N point sources in a line.

Since each emitter behaves as a slit diffraction optic or a point isotropic radiator the diffraction pattern can be derived by summing the phase shift p to the fringing term.

Starting with N-slit diffraction pattern with N slits of equal size a and spacing d $$\psi = \psi_0 \frac{\sin\left(\frac{\pi a}{\lambda}\sin\theta\right)}{\frac{\pi a}{\lambda}\sin\theta} \frac{\sin\left(\frac{N}{2}kd\sin\theta\right)}{\sin\left(\frac{kd}{2}\sin\theta\right)}$$

Fringe effects must be included: therefore, it is necessary to add the φ term to the kd sin θ to produce:

$$\psi = \psi_0 \frac{\sin\left(\frac{\pi a}{\lambda}\sin\theta\right)}{\frac{\pi a}{\lambda}\sin\theta} \frac{\sin\left(\frac{N}{2}\left(\frac{2\pi d}{\lambda}\sin\theta + \phi\right)\right)}{\sin\left(\frac{\pi d}{\lambda}\sin\theta + \frac{\phi}{2}\right)}$$

The intensity of the wave is calculated by taking the square of the wave function.

$$I = I_0 \left(\frac{\sin\left(\frac{\pi\alpha}{\lambda}\sin\theta\right)}{\frac{\pi\alpha}{\lambda}\sin\theta}\right)^2 \left(\frac{\sin\left(\frac{N}{2}\left(\frac{2\pi d}{\lambda}\sin\theta + \phi\right)\right)}{\sin\left(\frac{\pi d}{\lambda}\sin\theta + \frac{\phi}{2}\right)}\right)^2$$

$$I = I_0 \left(\frac{\sin\left(\frac{\pi\alpha}{\lambda}\sin\theta\right)}{\frac{\pi\alpha}{\lambda}\sin\theta}\right)^2 \left(\frac{\sin\left(\frac{\pi}{\lambda}Nd\sin\theta + \frac{N}{2}\phi\right)}{\sin\left(\frac{\pi d}{\lambda}\sin\theta + \frac{\phi}{2}\right)}\right)^2$$

For convenience it assumed that the emitters are separated by $$d = \frac{\lambda}{4}$$

apart. (any scalar fraction of the wavelength would function as well).

$$I = I_0 \left( \frac{\sin\left(\frac{\pi\alpha}{\lambda}\sin\theta\right)}{\frac{\pi\alpha}{\lambda}\sin\theta} \right)^2 \left( \frac{\sin\left(\frac{\pi}{4}N\sin\theta + \frac{N}{2}\phi\right)}{\sin\left(\frac{\pi d}{\lambda}\sin\theta + \frac{\phi}{2}\right)} \right)^2$$

Sine achieves its maximum value at $$\frac{\pi}{2},$$

thus, the numerator of the second term=1.

$$\frac{\pi}{4}N\sin\theta + \frac{N}{2}\phi = \frac{\pi}{2}$$

$$\sin\theta = \left(\frac{\pi}{2} - \frac{N}{2}\phi\right)\frac{4}{N\pi}$$

$$\sin\theta = \frac{2}{N} - \frac{2\phi}{\pi}$$

As N gets large, the result will be overshadowed by the π/2 term. In a oscillatory system, it is expected that sine will oscillate between −1 and 1, therefore setting $$\phi = -\frac{\pi}{2}$$

will provide the maximum energy on an angle derived by $$\theta = \sin^{-1} 1 = \frac{\pi}{2} = 90°$$

If an adjustment to the angle at which the maximum energy is emitted is required, it is only necessary to adjust the phase shift φ between successive emitters.

This technique can control any amount of paired integer elements in a phased array emission device. It is through this means that a nascent isotropic room temperature MASER oscillator can have a plurality of similar devices organized and controlled to produce a coherent beam of extremely large and stable characteristics. Inversely, a similarly active detector array will be able to deconstruct such a beam in order to get information that would otherwise be lost in the diffraction blur.

Established Uses of Lasers: In order to appreciate the potential utility of MASERs, it is useful to consider the physics and applications of Laser technology. Lasers have found a range of applications in medicine because of their inherent spatial precision. One such example is laser-assisted in-situ keratomileusis (LASIK) surgery for the treatment of refractive disorders in Ophthalmology (Reinstein et al., 2012). The precision and reproducibility required for this surgery would be difficult to achieve through other means (Asbell et al., 2001). However, Lasers cannot penetrate optically opaque tissues, limiting their use to externally accessible areas or requiring surgical access for targeting deeper pathologies. The recent development of laser interstitial thermotherapy (LiTT) for the treatment of epilepsy or brain tumors, requires stereotactic insertion of a catheter into the target area, through which a fiber-optic probe is introduced, and hence this technique is still invasive (Hoppe et al., 2017). Outside of medicine, Lasers are used for innumerable applications including precise spectroscopy ranging, sensing, micro-manufacturing, signal generation, material processing and microscopy (Milonni & Eberly, 2010). Two important concepts, established in the field of Lasers, but applicable to MASERs, are of particular relevance for this invention. Interferometry is the basis for Dynamic MASER Interferometry while doppler based laser-cooling inspired MASER Neuromodulation through energy coupling.

Interferometry: Interference patterns are generated when two mode-locked wave trains, or in the case of visible light—Laser beams, or Microwave—MASER Beams, coincide. If the two coincident beams have the same frequency and phase, the result is constructive interference, reinforcing the amplitudes. If they are out of phase, by ½ period, the result is destructive interference. Other combinations result in more complex, but interpretable, interference patterns. Interferometers are instruments that use this property for very precise measurements of processes occurring from the astronomical scale down to the microscopic scale (Bond et al., 2016). The Mach-Zehnder interferometer configuration is flexible and commonly used (Mach, 1892). The basic principle is to start with one laser beam, which is then split into two beams having the same frequency and phase. One serves as the reference or analyzing beam while the other serves as the probe beam and interacts with the relevant sample. The two beams are then integrated into a single convolved beam. The resultant convolved beam may be analyzed by both digital and analog techniques. Further, the convolved beam may be used as an illumination source for generating a derivative interference pattern that can be analyzed as a 2d or 3d image.

Laser Cooling: Laser cooling relies on quantum properties and the well-known Doppler Effect. In a given volume of non-constrained atomic gas above absolute zero, the atoms move randomly in Brownian motion. A source of narrowband coherent electromagnetic radiation can be deliberately tuned to a frequency slightly lower than that for spontaneous absorption of a favorable transition. Because of the Doppler effect, an atom randomly moving toward the source could experience the radiation as occurring at a slightly higher frequency than that of the beam, potentially its absorption frequency, absorb a photon, and transition to a higher energy state (FIG. 4). Once that electron relaxes back to its ground state after a few nanoseconds, it emits a photon, but now at its characteristic emission frequency, which is slightly higher than that of the originally absorbed photon. The small difference in frequency between the absorbed and emitted photons means that the atom loses a very small amount of kinetic energy with each cycle, which is dissipated in the surrounding volume. By using pairs or arrays of opposing beams, it is possible to effectively trap a volume of atoms, so they lose energy in multiple directions of movement. Since each event is very brief, the process can repeat many times in a short period, with the atoms losing kinetic energy over many iterations. This approach has been used to rapidly cool substances close to absolute zero and was critical in the recent demonstration of the Bose-Einstein condensate (Anderson et al, 1995).

Resonant Coupling: Doppler-cooling is an effective demonstration of how coherent emissions can achieve surprising and seemingly counterintuitive results through their quantum effects. However, the tuning range for Doppler cooling is very narrow and another quantum interaction, resonant coupling, is the basis for the current disclosure. Wave-coupling occurs when two waves are linked in some way so they can transfer energy. Resonance occurs if the two have a common frequency and are at least partially in-phase. An imperfect but helpful analogy is the example of an adult pushing a child on a swing. The swing has a natural frequency of oscillation. After a few pushes, if the adult repeatedly pushes the swing at the same frequency the oscillation, both the adult and the swing are in-phase, and the child goes higher and higher An analogous phenomenon can be observed with the behavior of two-level quantum systems in the presence of coherent electromagnetic radiation. For practical purposes, most quantum shifts can be reduced to two-level systems. American physicist Isaac Rabi's derived the formula for estimating the probability of finding such a system in one or the other state, as a function of time see FIG. 5 and the following equations: $\Omega=\sqrt{\lambda^2+(\omega-\omega_{21})^2/4}$; $P_2(t)=1-P_2(t)$;

$$P_2(t) = \left[\frac{\lambda^2}{\lambda^2 + (\omega - \omega_{21})^2/4}\right]\sin^2(\Omega t).$$

These equations and the plot in FIG. 5 illustrate the probability of finding one of the states in presence of coherent emission at the resonance frequency ($\Gamma=0$) and at increasingly detuned frequencies ($\Gamma=\Omega/10$) . . . wherein $\Omega$ is the Rabi frequency, $\gamma$ is equal to 1 in non-relativistic conditions, $\omega$ is the frequency of the perturbation, $\omega_{21}$ is the resonance frequency of the system, t is time, $P_1$ is the probability of finding the system in state-1, and $P_2$ the probability of the system being in state-2, and $\Gamma$ represents different levels of detuning. If the coherent radiation has the same frequency as the resonant frequency, then over time, the system alternates between states 1 and 2 at the frequency of the radiation. Critically, coherent radiation is effective at modulating the probability of states, or transitions, even if the frequency is not exactly the same as the resonant frequency of the molecule, so long as falls within a certain range. Practically, this means that frequency coupling is more forgiving than the Doppler Effect, described above in laser cooling, which requires extremely narrow tuning.

Diffraction Limits: The Abbe limit is a well settled understanding of the behavior for diffraction-based optics. This holds true for all electromagnetic radiation, which ranges from radio waves to gamma rays, and includes visible light (FIG. 5). Electromagnetic radiation waves, as their names suggest are fluctuations of electric and magnetic fields, which can transport energy from one location to another. Visible light is not inherently different from the other parts of the electromagnetic spectrum with the exception that the human eye can detect visible waves. Electromagnetic radiation can also be described in terms of a stream of photons which are massless particles each travelling with wavelike properties at the speed of light. A photon is the smallest quantity (quantum) of energy which can be transported.

The observation of sub-wavelength structures with microscopes is difficult because of the Abbe diffraction limit. Ernst Abbe found in 1873 that electromagnetic oscillatory fields with wavelength $\lambda$, traveling in a medium with refractive index n and converging to a spot with half-angle $\theta$, will have a minimum resolvable distance of:

$$d = \frac{\lambda}{2n\sin\theta} - \frac{\lambda}{2NA}$$

The portion of the denominator n sin $\theta$ is called the numerical aperture (NA) and can reach about 1.4-1.6 in modern optics, hence the Abbe limit is d=$\lambda$/2.8. Considering green light around 500 nm and a NA of 1, the Abbe limit is roughly d=$\lambda$/2=250 nm (0.25 µm), which is small compared to most biological cells (1 µm to 100 µm), but large compared to viruses (100 nm), proteins (10 nm) and less complex molecules (1 nm). To increase the resolution, shorter wavelengths can be used as in UV and X-ray microscopes. These techniques offer better resolution but are expensive, suffer from lack of contrast in biological samples, and may damage the sample.

Near-field Techniques: The diffraction limit is only valid in the far field as it assumes that no evanescent fields reach the detector. Various near-field techniques that operate at less than ≈1 wavelength of light away from the image plane, can obtain substantially higher resolution. These techniques exploit the fact that the evanescent field contains information beyond the diffraction limit which can be used to construct very high-resolution images, in principle beating the diffraction limit by a factor proportional to how well a specific imaging system can detect the near-field signal. For scattered light imaging, instruments such as near-field scanning optical microscopes peripherally resemble an atomic force microscope. The data recorded by such instruments often requires substantial processing, essentially solving an optical inverse problem for each image.

The use of synthetic aperture techniques in the emitter and the detector in the subject disclosure permits the recovery of information well beyond the diffraction limit.

MASER Interaction with Brain in Activity Mapping: The brain represents a complex mixture of organized atoms, molecules, membranes, and cells. However, one goal of the invention is to apply some of the same considerations related to activity mapping to a complex biological object such as the brain. Referring to FIG. 6, neuronal processes such as axons or dendrites are antennas, preferentially coupling MASER emissions to molecules such as voltage gated ion channels and receptors embedded within the phospholipid bilayer. However, the brain is not a uniform substance. Hence, one object of the invention is to selectively record activity and either enervate or activate specific areas based on a number of features including 1) the pattern of activity, 2) the molecular characteristics of different neurons, 3) the spatial location of neurons in the brain relative to a three-dimensional structural map obtained using conventional 3-D MRI or CT images and 4) the size and configuration of particular neuronal subtypes. In the exemplary embodiment of the invention, each of these factors affects interaction of the probe beam with the brain. These changes are then detected in the interference pattern generated by recombining the probe beam with the reference beam. In the exemplary embodiment, a low energy probe beam and reference beam are generated using the phased array of MASER emitters as described in the incorporated, co-pending application Ser. No. 17/148,215 entitled "Thin Film MASER Emitter and Thin Panel Phased Array of Emitters". The interference pattern is detected preferably using the phased array of detector elements described in the incorporated, co-pending application Ser. No. 17/148,275, entitled "Phased-Array MASER Detector for Synthetic Aperture Interferometric Imaging".

High frequency MASERs can predictably penetrate optically opaque tissues and can affect state conditions of vibratory molecules via resonant coupling. This invention capitalizes on these capabilities to create systems to modulate specific brain areas. For example, the system can de-energize molecules just enough to temporarily stop or perturb neuronal activity, but not to cause any long-lasting harm. The system can energize hypoactive brain areas to restore a more normal pattern of activity; and the system can ablate pathological areas such as deposits of neoplastic cells or abnormal areas giving rise to seizures (cortical dysplasia, sclerotic hippocampi in Mesial Temporal Lobe epilepsy).

Biological Basis of Neuronal Activity: The basic work of the brain is performed by neurons. A typical neuron has three important elements, the dendritic tree, the soma, and the axon (see FIG. 7). Neurons maintain a resting membrane potential of −70 Mv primarily through the Na+/K+-ATPase, an active molecule in the cell membrane that moves 3 Na+ ions out of the cell and two K+ into the cell for each unit of ATP.

Neurons communicate through the release of neurotransmitters at synaptic junctions (see FIG. 8). A neuron integrates the excitatory and inhibitory inputs to its dendritic tree, which are generated by synapses from other neurons. If there are enough excitatory potentials at a given time causing the membrane at the take-off of the axon from the soma (the axon hillock) to reach its threshold (−55 Mv), then an action potential is initiated through the local opening of voltage-gated $Na^+$ channels allowing $Na^+$ ions to rush into the cell causing the membrane potential to become transiently positive to a peak of +30 Mv (see FIG. 7). As the membrane becomes depolarized, voltage-gated $K^+$ channels start to open allowing $K^+$ to leave the cell. Once the action potential reaches its peak, the Na+ channels close while K+ channels continue to be open, causing the membrane to return to, and slightly exceed, its resting potential (a period called hyper-polarization), during which it is refractory to the generation of action potentials.

Synaptic Vesicle Release: Once an action potential is initiated, adjacent areas of the membrane become depolarized, reach the threshold and depolarize, leading to a wave of depolarization traveling along the axon, away from the soma, in the process of propagation. Once the wave of depolarization reaches the axon terminal it causes voltage-gated $Ca^{++}$ channels to open. The increased intracellular concentration of $Ca^{++}$ causes synaptic vesicles to fuse with the membrane at the synaptic terminal and release their neurotransmitter into the synaptic cleft (FIG. 8). At this point, the neuron under discussion becomes the presynaptic neuron affecting the next postsynaptic neuron.

Neurotransmitters exert their effects through ligand-gated channels, or G-protein coupled receptors that can induce inhibitory or excitatory potentials in the postsynaptic neuron. Ligand-gated channels and G-Protein coupled receptors are critical to neurotransmission and are the targets of a large number of pharmacologic agents as well as substances of abuse.

Molecular Changes Recorded by MASER System: This process of summating inputs, initiating action potentials, and releasing neurotransmitters is the essence of neuronal activity. Most of the critical elements are mediated by conformational changes in membrane bound ion channels. These activity based conformational changes are a primary signal for MASER activity mapping using this invention and a primary target for MASER neuromodulation using this invention. In addition, the flow of ions in and out of neurons is associated with changes in water volume representing another signal the MASER system can record.

Voltage-Gated Channels: Voltage-gated ion channels ($Na^+$, $K^+$, $Ca^{++}$) share a similar structure. There is an α-subunit tetramer having four repeat domains, labelled I through IV, each containing six membrane-spanning segments, labelled S1 through S6. The S4 segment acts as the channel's voltage sensor. The voltage sensitivity of this channel is due to positive amino acids located at every third position. When stimulated by a change in the membrane potential, this segment moves toward the extracellular side of the cell membrane, allowing the channel to become permeable to ions which move down their gradient.

Ligand-Gated Channels: Ligand-gated ion channels (LICs, LGIC), also commonly referred to as ionotropic receptors, are a group of trans-membrane ion-channel proteins that respond to particular neurotransmitters (ligands) by undergoing a conformational change thereby opening a pore to allow ions such as $Na^+$, K+, $Ca^{++}$, or $Cl^-$ to pass through the membrane (see FIG. 9). There are three classes of these channels. Cys-loop receptors are pentameric structures. Examples include the Serotonin receptor and the nicotinic acetylcholine receptor found in the neuromuscular junction. Ionotropic glutamate receptors are tetrameric structures that generate a rapid influx of Na ions into the cell and depolarizing the membrane, in response to glutamate, the primary excitatory neurotransmitter in the brain. GABA receptors are pentameric structures that bind GABA and permit $Cl^+$, which is the primary inhibitory neurotransmitter in the brain. Upon binding GABA, the receptors permit $Cl^+$ into the cell, thereby hyperpolarizing the membrane.

G protein-coupled receptors (GPCR's): These constitute a large and important family of receptors that bind with molecules outside the neuron and activate internal signal transduction pathways (G proteins) that affect cellular activity. The receptors have seven membrane spanning regions (FIG. 10). Upon binding with a ligand, the receptor undergoes a conformational change releasing a GDP molecule in exchange for a higher energy GTP molecule. This then activates the G protein which then activates further signaling cascades. GPCR's mediate the effects of a large number of agents including dopamine, norepinephrine, histamine, and opiates such as morphine. It is estimated that about 35% of all pharmaceutical drugs target GPCR's.

Neuropsychiatric disorders such as Addiction, Major depression, Post-traumatic Stress Disorder (PTSD), and Obsessive-Compulsive Disorder are associated with abnormal patterns of activity in different brain regions in response to provocative stimuli—the Orbital-Frontal cortex and Nucleus Accumbens in addiction, Area 25 of the medial frontal cortex in Major Depression, the amygdala in PTSD, and the dorsal Anterior Cingulate Cortex in OCD. These areas have been targeted with invasive therapies such as deep brain stimulation (DBS) and non-invasive therapies such as Transcranial Magnetic Stimulation (TMS), though the effects have been modest given the limited volume modulated by DBS along with the poor spatial resolution and steep attenuation of TMS energy for deeply situated targets.

Oscillatory Activity. In addition to the activity of single neurons, brain signaling occurs through coherent oscillations that may span groups of neurons or small nuclei, cortical regions such as the primary visual cortex or the hippocampus, or networks encompassing multiple cortical and subcortical areas. Brain oscillations are thought to bind certain areas together and to transmit certain kinds of information—analogous to a carrier frequency in radio transmission. Cortical oscillations occur normally in the following ranges Delta-band oscillations (1-5 Hz) occur during slow-wave sleep, Theta-band oscillations (6-10 Hz) are found in the hippocampus during formation of memories, Alpha-band oscillations (10-12 Hz) occur quite wakefulness, Beta-band oscillations (13-25 Hz) in sensorimotor areas during the planning and execution of movements, whereas low and high Gamma-band oscillations (26-50 Hz and 51-500 Hz, respectively) are important in a variety of cognitive tasks, particularly those requiring sequential processing.

Derangements in cortical oscillations are strongly associated with neurological disorders. For example, paroxysmal bursts of Theta activity in the hippocampus trigger seizures, excessive Beta-band oscillations in Parkinson disease impair movement, and disrupted Gamma-band oscillations are associated with the cognitive impairment of Alzheimer disease. Modulating cortical oscillations is a major goal of current invasive neuro-modulatory therapies as deep brain stimulation (DBS), and noninvasively through the disclosed system using Coherent Microwaves for therapeutic modulation.

MASER System Activity Recording of Channels and Receptors: In accordance with one aspect of the invention, as the probe beam traverses the brain, it encounters molecules that have state changes related to neuronal activity. For example, it will encounter ion channels that maintain the membrane potential of neurons. At one moment, in a particular area of interest, the neurons may be relatively quiescent, which would generate a particular interference pattern. Some milliseconds later, some of the neurons may be nearly depolarized due to changes in the structure of voltage-gated $Na^+$ channels, allowing $Na^+$ into the cell. A few milliseconds later, that group of neurons may be actively firing action potentials, which causes other sequential changes including repolarization through the opening of voltage-gated $K^+$ channels, the movement of vesicles and release of sequestered neurotransmitters through the opening of voltage-gated $Ca^{++}$ channels, the release of neurotransmitters, and their postsynaptic effects on ligand-gated channels and G-protein coupled receptors in post-synaptic neurons. All of these molecular conformational changes can be associated with different interference patterns. One object of the invention is to focus the MASER system on ion channels and receptors because they undergo distinct conformational changes. These have associated changes in energy levels, absorptions, and emissions that are capable of being captured by the system. In addition, the flow of ions in and out of the cell is associated with changes in the amount of water, a signal that can also be captured by the system. Moreover, the activity of ion channels and receptors is the essential mechanism whereby neurons communicate through the generation of excitatory and inhibitory postsynaptic potentials, only some of which lead to action potentials.

In accordance with one aspect of the invention, the system differentially records conformational changes in voltage-gated ion channels, ligand-gated ion channels, and G protein coupled receptors. This allows the recording of neuronal activity at the cellular and subcellular level. Moreover, each of these channels and receptors has unique patterns of absorption and emissions that change depending on the conformational state. Thus, the described system identifies neurons having increased, or decreased, activity relative to the background, but also identifies the particular type of channel in play and hence the associated neurotransmitter or ligand.

Protein Aggregates: Neurodegenerative disorders such as Parkinson, Alzheimer, and Huntington's disease, are characterized by the accumulation of misfolded protein in neurons. Each disorder is associated with the aggregation of a particular moiety: Alzheimer—B pleated sheets; Parkinson—α Synuclein, and Huntington's Disease. Individual protein molecules are easily broken down and cleared by normal cellular processes. However, once these particular proteins aggregate into increasingly larger pathological aggregates (sheets, folds, fibrils, and tangles) they become insoluble and therefore both inaccessible and highly resistant to normal cellular mechanisms for protein degradation. In another aspect of the invention, another object is to selectively energize these pathological aggregates, allowing them to dis-aggregate, at which point they can be cleared by the cells. This method has the potential to arrest and reverse progression of Parkinson disease, Alzheimer disease, and Huntington's disease.

Neuronal processes such as axons or dendrites are antennas, preferentially coupling MASER emissions to molecules such as voltage gated ion channels and receptors embedded within the phospholipid bilayer. Most features of neuronal activity, such as depolarization, generation of action potentials, and neurotransmitter release, are mediated through conformational changes of molecules embedded in the phospholipid bilayer. The activity mapping will identify changes the spatial location of the changes. Molecules susceptible to energy coupling will be apparent as different patterns of spectral absorptions and emissions, occurring during the period of activity. Hence, the map can provide information regarding both the spatial location and the presence of molecular targets for enervation. With that information, it is possible to create a convolved beam targeting particular patterns of activity observed in the interference map of the structure.

Differentiation of Neuronal Subtypes: Neurons play vital roles in central and peripheral nervous systems, including integration, production, and transmission of electrochemical signals, and establishment of plastic network connectivity. From prenatal development through adulthood, these functions are determined by many interacting factors, such as gene expression, intracellular molecular dynamics, and the type and distribution of ion channels.

There are many types of neurons, but the following types are the best characterized and known to participate in the vast majority of important brain processes. They have different dimensions and are found in different areas, providing two means for discrimination (size and location) using the method disclosed in this application.

Cortical Pyramidal Neurons are in layer 5 of the cerebral cortex and project to adjacent cortical areas (U fibers), to nonadjacent areas in the same hemisphere and to the opposite hemisphere. Pyramidal neurons in the motor areas have extremely long axons and project to the brainstem and spinal cord. Cortical Pyramidal neurons are excitatory and use glutamate as their neurotransmitter. Cortical pyramidal neurons are involved in sensation, movement, and cognitive processes such as decision making.

Cortical Interneurons are smaller than pyramidal neurons and have only local connections. The vast majority are inhibitory and use GABA as their neurotransmitter. They regulate cortical activity to maintain a homeostatic balance.

Medium Spiny Neurons (MSN's) are in deep gray matter nuclei called the basal ganglia. They project from one nucleus to another in well-defined cortical basal ganglia loops. These loops, with their constituent MSN's, are important in motivations, learning, and the performance of habitual movements. Derangements of these circuits is implicated in impulsivity, addiction, and the development of compulsive patterns of behavior.

Basal Ganglia Interneurons do not project outside their respective nuclei. The most relevant interneurons use either GABA or acetylcholine as their neurotransmitter. GABAergic interneurons are small, while cholinergic interneurons are quite large (bigger than either GABAergic interneurons or MSN's. Disruption of these interneurons is implicated in movement disorders such as Parkinson disease.

Hippocampal Pyramidal Neurons are found in area CA3 of the hippocampus. They are small and densely packed and play an important role in the formation of memories, particularly spatial memories. Disruption of these neurons is implicated in temporal lobe epilepsy and dementing disorders such as Alzheimer disease.

Modulatory Neurons are found in the midbrain or hypothalamus but have projections to large areas of the cortex and basal ganglia. They include dopaminergic neurons in the Ventral Tegmental Area (VTA) and Substantia Nigra pars compacta (SNpc) of the midbrain, the serotonergic neurons in the Raphe Nucleus (RN), noradrenergic neurons in the Locus Coeruleus (LC), and cholinergic neurons in the Nucleus Basalis (NB). Dopaminergic neurons play an important role in learning and drug addiction, noradrenergic and serotonergic neurons play an important role in setting the overall activity level of the brain and are implicated in depression, while cholinergic neurons play a role in memory formation and are implicated in Alzheimer disease.

Neuronal Location and Size: In some brain disorders such as addiction or epilepsy, there is pathological overactivity or underactivity of specific brain regions relative to the surrounding background activity. In these disorders, it is straightforward to apply enervating or energizing MASER beams to the abnormal area. Other disorders represent an altered pattern or sequence of activity, but not a change in the absolute magnitude of activity.

There is considerable diversity in neuronal size. Brainstem motor neuron and cerebro-cortical stellate dendritic trees have similar shapes and numbers of branches (53 and 51, respectively) but different total lengths (6298 to 1966 μm). Hippocampal CA3 pyramidal and cerebellar Purkinje cell (right) dendritic trees have similar lengths (9670 and 9883 μm) but different numbers of branches (121 and 567).

Overall size encompasses an important subset of morphological characteristics of neuronal arbors. Distinct functional aspects of internal neuron size are defined by the total number of terminal branches (the "degree" of the tree) or by continuous morphometrics including total length, surface area, and internal volume. The spatial extent of the neuron can also be described in terms of distance reached from the soma or by the height, width, and depth of a box containing the whole arborization. Greater length often corresponds to a greater area of invaded space, and thus greater potential connectivity. For axons this may result in increased divergence (one signal sent to many cells). Total wiring is minimized by increasing length for axons over dendrites when divergence is higher than convergence (more presynaptic than postsynaptic neurons). When convergence is greater than divergence, dendrites have relatively greater length. These predictions were confirmed in retinal, cerebellar, olfactory bulb, and neocortical neurons.

Membrane surface area correlates with the number of synapses in dendrites and axon terminals. Signal propagation speed linearly increases with diameter; however, the metabolic cost also escalates due to the squared relationship between diameter and cross-sectional area. Within the generally large metabolic costs of the brain, synaptic transmission and spike generation are particularly energy intensive due to the high ATP requirements of ionic pumps. The total number of branches (defined as the regions between two bifurcations or between a bifurcation and a termination) is another measure of absolute tree size and varies widely between cell types. Individual branches may operate in isolation for the separate processing of specific groups of synaptic inputs. Bifurcations also serve as nodes of integration, enhancing dendritic computational power.

Qualitative and Quantitative Neuromorphological Features: Tree shape is often the most visually obvious identifier of neuronal arbor and cell types. For example, pyramidal cell dendrites are composed of two polarized arbors, apical and basal. Both grow away from the cell body in opposite directions, receiving input from different sources. Basal dendrites spread out as they extend from the soma, taking a conical shape with the apex located at the cell body. Apical dendrites also spread out as they grow away from the soma, but they elongate more than basal dendrites, differentiating further as they advance through multiple layers.

Pyramidal cells are the principal neurons in both the cerebral cortex and hippocampus. Although all pyramidal cells share a relatively similar appearance, some differences also exist between regions. There is less difference between cell types when measuring pyramidal dendrites along their principal axis of growth, where cortical pyramidal dendritic arbors (apical and basal combined) are ~70% the size of hippocampal pyramidal dendritic arbors ($p<0.05$). Hippocampal neurons are relatively spread out along the other two orthogonal axes compared to cortical pyramidal cells, which appear more elongated. Cortical dendrites may be confined within a more restricted lamella thus appearing flatter. Differences in tissue slice shrinkage leading to greater distortion in one of the cell types may also explain the results.

Cerebellar Purkinje cell dendrites are mostly restricted to growth in two dimensions. They fan out significantly in the rostrocaudal direction but are nearly flat mediolaterally. Purkinje cells are thus aligned in neat rows correlating with the deep folds (folia) throughout the cerebellar cortex. This architecture may help minimize the length of shared parallel fiber inputs. Some dendritic types, such as in retinal ganglion cells, stop growing upon reaching neighbors of the same type. The resulting 'retinal tiling' spatial layout suggests repulsion between neighboring neurons as a shape-constraining mechanism. Other neuronal types such as stellate cells and motor neurons grow away from the soma in many directions (i.e. they are multi-polar).

Underlying the shape and physical qualities of dendrites and axons is the cytoskeleton. The cytoskeleton provides and maintains the structural properties of the neuronal trees, mediating intracellular transport, and branch diameter, elongation, and bifurcation. Different cytoskeletal fibers include actin filaments, microtubules, and other intermediate filaments. In dendrites, actin is largely found near the branch surface, where it can give rise to high densities of spines, as well as forming filopodia that sample the extracellular environment to guide direction and growth patterns determining overall shape. Microtubules make up much of the branch core and act as a skeletal backbone maintaining the neuronal tree shape. Microtubules have polarity which determines the direction of resource transport and is an important differentiating factor between axons and dendrites. Axon microtubules only transport distally (towards the plus-ends), while dendritic microtubules face both directions. The loss of function of a motor protein that drags the microtubules into dendrites minus-end first results in elongated dendrites without taper and with an organelle makeup closer to an axon.

The size metrics discussed so far relate to many neuronal functions. However, other functional properties depend on more complex shape and size metrics such as branching distributions and patterns. Branching patterns and distributions can be measured in numerous ways providing a challenging choice for the best metrics to explore for a given cell type and features of interest. The following section reviews some common topological measurements including partition asymmetry and modifications thereof.

Size, Complexity and Asymmetry: Considering the shape of neurons beyond their size opens the door to a more extensive set of metrics. Early measures of complexity were restricted to 2D images of neurons. Sholl analysis is a common metric that counts the number of branches at regular distances from the soma. Modified (or Sholl-like) analyses, including 3D variations, were natural extensions once digital 3D reconstructions became available. Sholl-like analyses expand size metrics by analyzing their distribution relative to distance measures such as branch order or path distance. As an example, dendritic branches tend to thin as they elongate. Accordingly, numerous computational modeling studies have used distance-dependent diameters to stochastically produce realistic neuron/arbor types.

Krichmar et al., loading CA3 pyramidal cell reconstructions into an electrophysiological simulation environment, found that size morphometrics affect firing activity but cannot account for all aspects of electrophysiological behavior. How dendrites are distributed across branch order significantly correlates with aspects of firing patterns. These results suggest that complex morphological properties must be characterized not only by overall size, but how size varies within the given tree.

Partition Asymmetry: Morphological asymmetry reflects the relative balance of branches or size within a tree. Partition asymmetry ($A_p$) is a relative measure of asymmetry at a bifurcation node based on the distribution of degree (number of terminals) between the node's two subtrees. The value ranges from 0 (symmetric) to 1 (asymmetric). Since degrees are integers, the number of possible values of $A_p$ depends on the node total degree. The denominator represents the degrees of freedom (total degree minus two, as both left and right subtrees must have at least one terminal).

The number of possible tree shapes increases exponentially with tree size. Even relatively small trees exhibit an exorbitant number of possible branching patterns. Given the relatively small number of observations enabled by experimental data acquisition, it is impossible to know if there is only a subset of tree shapes that fully represents a given cell type. It is therefore useful to have an informative scalar morphometric about tree shapes. Van Pelt defined the tree asymmetry index as the average partition asymmetry across a tree, finding this measure sensitive to different tree shapes.

Because partition asymmetry measures the asymmetry of a node given all possible degree distributions, nodes that can only have one possible distribution (i.e. nodes with degree 2 or 3) technically do not have an asymmetry value. Van Pelt et al. choose to give the two possible partitions with degrees <4 asymmetry values of 0 and 1 for practical purposes but recognize that these values are arbitrary and mention several alternative methods to measure asymmetry in neuronal trees. Measuring asymmetry at the tree level as opposed to locally provides a different measure that depends on node size.

Nodes that contribute to a greater part of the entire tree have proportionally greater influence on the measured asymmetry. Since this measure is global in nature, a more absolute partition asymmetry is appropriate. This is achieved by not subtracting 2 in the denominator of the partition asymmetry equation, such that trees with a greater absolute difference in subtree sizes always have greater partition asymmetries.

Asymmetry can also be measured using continuous size metrics such as length, surface area, and volume. Since the branches diverging from a bifurcation have continuous size, even a node with two terminals can be asymmetric. There is therefore no reason for limiting the nodes to be included in such a measure. Additionally, since it is length (or surface area or volume) and not degree being measured, degrees of freedom are not a factor. Donohue and Ascoli tested the accuracy of growth models in computer simulations using different asymmetry metrics. Basal and apical tree degree asymmetries were accurately produced by different morphometric constraints (diameter and path distance, respectively). Surface area asymmetry however was best determined by path distance for both arbor types. These results suggest that different asymmetry measures may be determined by distinct factors depending on neuron or arbor type.

A novel implementation of partition asymmetry termed "excess asymmetry" is used to measure morphological homeostasis in hippocampal dendritic trees. This metric is based on the idea that if an arbor grows under homeostatic constraints, then larger subtrees will offset smaller subtrees, limiting the size range of the entire tree. Specifically, consider a node with subtrees l and r, where l has subtrees a and b, and r has subtrees c and d. Switching b with either c or d will result in a more symmetric node in case of homeostasis (if a and b are large then c and d are small or vice versa). Excess partition asymmetry then compares the actual partition asymmetry with the swapped partition asymmetries, producing a positive value if there is homeostasis and a value near 0 otherwise. Degree, length, and surface area were all used to determine excess asymmetry. Significantly positive excess asymmetry values were found in several dendritic types of cortical principal cells, suggesting that subtrees grow under homeostatic constraints.

Relationships: Size metrics have been found to classify arbor and cell types better than some simple asymmetry scalars. However, asymmetry's relevance may require more targeted methods to fully capture cell type variation. Cuntz et al. modeled a dendritic structure by minimizing total wiring to a sample of potential synaptic sites from a reconstructed fly tangential cell. The resulting virtual dendrite was very different from the corresponding reconstructed cell. It was quite asymmetric and had a clear main path. A second model constrained both total wiring and path distance from synaptic site to soma. Diameter and taper rate were also constrained to minimize the current transfer variability between synapse to soma paths. The result appeared much like the source cell, with several levels of fairly symmetric branching followed by more asymmetric regions. A single asymmetry measure would not be capable of describing the multiple dendritic sub-domains, whereas a set of targeted measures could capture such functionally related patterns.

Neurons abide to many constraints and functions beyond homogeneous synaptic efficacy and minimizing metabolic cost. A more generalized recent model to relate neuronal function and morphology involved an evolutionary algorithm, with "genes" made up of tree growth parameters, and electrophysiological simulations to test virtual neuron fitness. Based on the chosen functional parameters, the model finds optimal dendritic arbors over many generations. Within the resulting set of morphological parameters, those vital to the specified neuronal fitness are more highly conserved.

Caulescence: The term "caulescent" was originally used in botany to describe a plant with a main trunk or stem. Referring to FIG. 11, the main path of a neuronal tree can be defined as the path from the soma to a termination which at each bifurcation leads to the greatest extent of a given metric (e.g. degree, length, surface area or volume). Degree-based caulescence ($C_D$) follows the path that leads to the higher degree at each bifurcation, while length-based caulescence ($C_L$) takes the path towards the most length. Caulescence is then defined as the weighted partition asymmetry of nodes along the main path. This choice factors out the influence of secondary subtrees and weights more heavily the bifurcations with the largest extent.

Both the partition asymmetry and weighting are based on the same metric used to determine the main path itself. The equation for caulescence is:

$$C = \Sigma |l-r| / \Sigma (l+r)$$

where l and r are the sizes of the two subtrees at each node on the main path. The resulting value represents the overall balance of extent, where high caulescence (close to 1) indicates a very distinct main path and low values reflect a more balanced tree without a clear main path.

Main paths in example neurons. A. Hippocampal subicular pyramidal dendritic arbor. Main path (red) is more caulescent in apical (gray, $C_L$=0.88; $C_D$=0.88) than basal trees (blue, $C_L$=0.38±0.14; $C_D$=0.36±0.07; N=5). Boxed Inset: Zoomed-in (2×) individual basal tree with main path (red) ($C_L$=0.24; $C_D$=0.43). B. Hippocampal CA1 pyramidal cell dendritic (basal: dark blue; apical: gray) and axonal (light blue) arbors. Axonal main path (thickened red) would not be obvious without color, even though this axonal tree is highly caulescent ($C_L$=0.89; $C_D$=0.89). Some branches are thickened for visual clarity. $C_L$=length-based and $C_D$=degree-based caulescence.

The significance of caulescence in neuronal arborizations is revealed in the drastic differences between the values of various cell and arborization types. Using the length metric and NeuroMorpho.Org arbors, pyramidal cell apical dendrites tend to be highly caulescent (0.62±0.17, N=889), while their basal counterparts have much less caulescence (0.37±0.17; N=1779; p<0.001). The main path is more obvious in apical compared to basal dendritic trees. High caulescence by volume or surface area in dendrites can optimize synaptic integration along the main path, analogous to elongating the soma. In fact, surface area (as well as volume, not shown) caulescence is significantly higher than length caulescence for both pyramidal basal (0.39±0.17; p<0.05) and apical dendrites (0.69±0.16; p<0.001). This fits with secondary (e.g. oblique) branches having smaller diameter than main branches and therefore high input impedance.

Two groups of NeuroMorpho.Org axons had sample sizes large enough for analysis and varied substantially between types. Cortical basket cell axons had a lower mean caulescence (0.54±0.15; N=57) than uniglomerular projection neuron axons (0.73±0.10; N=233; p<0.001). As would be expected due to the lack of taper in axons, neither cell class had axons with a significantly different surface area ($C_S$) or volume-based ($C_V$) caulescence compared to $C_L$ and $C_D$. The main path in both apical dendrites and axons is acting in part as an efficient way to get from an origin (i.e. soma) to a destination (i.e. apical tuft, axonal terminals), as opposed to sending many branches to neighboring targets.

The adaptation of partition asymmetry in the caulescence definition results in a fairly strong correlation between caulescence and several asymmetry measures, particularly global asymmetry. A tree with more than one true main path has lower caulescence due to a highly weighted bifurcation with low partition asymmetry where the second main path begins. The global asymmetry of the tree would then be higher than its caulescence because other highly weighted bifurcations on the second main path would contribute a relatively high partition asymmetry. Rodent cortical apical dendrites show no significant difference in correlation above or below caulescence of 0.5. While rodent hippocampal (0.66±0.21; N=205) and cortical (0.67±0.13; N=258) apical dendrites have similar mean caulescence, primate cortical apical dendrite values (0.57±0.15; N=387) are substantially lower. These results signify important differences between both brain region and species even within a cell and arbor type, see FIG. 12.

FIG. 12 is a scatter plot of rodent pyramidal cell apical dendrite global asymmetry against caulescence (C), both using the length metric. Circles represent hippocampal neurons, and crosses; cortical neurons. Solid is the diagonal, where global asymmetry equals caulescence. At C>0.5, caulescence is greater than global asymmetry, suggesting a difference between bifurcations in the primary and secondary paths. Variability in global asymmetry for hippocampal apical dendrites increases at C<0.5. This could be explained by dendrites with multiple main paths. The top left insert in FIG. 12 plots mean ratios of global asymmetry to caulescence below and above 0.5 caulescence is significantly different for hippocampal cells (p<0.0001). The bottom right insert in FIG. 12 plots partition asymmetry analysis of all rodent apical dendrite nodes. Primary path bifurcations have significantly higher partition asymmetry than secondary path bifurcations (p<0.0001).

Lower global asymmetry may be due to secondary branches. Measuring partition asymmetry separately along the main and secondary paths can distinguish the relationship of potentially separate domains. A 2-sample Kolmogorov-Smirnov test rejected that the primary and secondary branch partition asymmetry values could come from the same population (p<0.001). These results show that main path nodes indeed have significantly higher partition asymmetry than secondary nodes. This means that the asymmetry of apical dendrites is due primarily to the effect of the main path.

For simplicity's sake, only caulescence defined along a single main path was analyzed. Future incarnations of the metric may be expanded by considering the multiple main paths that certain individual trees exhibit, such as some of the low caulescence but high global asymmetry apical dendrites. Additionally, cerebellar climbing fibers and Purkinje cells appear to have main paths that split in multiple directions. Another aspect of separating morphological sub-domains is the determination of where a main path terminates. Removing acaulescent regions would further differentiate sub-domains. For example, the apical tuft of apical dendrites is more symmetric and thus its exclusion from the main path would likely further increase the high caulescence values of these trees.

The EHF coupling coefficient within the scope of this invention is likely to have a high Q limited to the arborized neuronal dendritic spikes. However, multiple resonance and tonal shifts will occur due to the atypical caulescence and possible other dendritic or axonal topological asymmetries.

Absorption of RF Radiation by Human Tissue: A radio wave in space is characterized by its frequency, intensity of electric and magnetic fields, direction, and polarization. The interaction of external radio waves with biological bodies produces internal electric and magnetic fields, which can be calculated by solving Maxwell's equations for the given boundary conditions. This becomes a complex problem, however, because biological bodies are heterogeneous and complex in shape, making an exact solution impossible. In addition, the intensity of the internal field is greatly dependent on the boundary conditions under which the external field is applied. The frequency, intensity, and polarization of the field, in addition to the size, shape, dielectric properties of the exposed body, the spatial configuration of the exposure source and the body, and the presence of other objects in the vicinity, play a big role in the effect the radio waves will have on the body. For this reason, the internal field created in a mouse under a given external field will be much different than the internal field created in a man under the same external field.

We are interested in how external fields couple with biological bodies to create internal fields. The field strength inside a cell nucleus, for example, would be needed to judge any effects on genetic information. Likewise, the field strength across the cell membrane would be needed to evaluate possible membrane excitation phenomena. We must first be able to figure out the field strength inside the human body and then how this is related to membrane potentials etc.

Internal field strength increases proportionally with the external field strength, but the internal field is not necessarily uniform even if the incident field is uniform.

The frequency of maximal absorption is called the resonance frequency (for humans it is between 70 and 100 MHz), and depends on orientation with respect to the incident field. In general, the rule is that the shorter the subject, the higher the resonance frequency, and vice versa.

Exact field strength is dependent on local geometry: in a man standing in a field perpendicular to the ground, the average current density in the legs is greater than in the trunk, by a factor that corresponds to the ratio of the cross-sectional areas of the trunk and leg. Absorbed energy depends on the size of the body, curvature of its surface, ratio of body size to wavelength, and the source characteristics.

Differential Tissue Absorption: The magnetic permeability of most tissues is practically equal to that of free space, meaning that tissue is essentially nonmagnetic. Interactions at high radio frequencies occur through the electric field, which therefore describes the exposure field interactions with the tissue. Frequency characteristics, modulation characteristics, and modulation frequency of the external field are also important in determining interactions with tissue.

Both electric (E) and magnetic (H) fields at radio frequencies decrease exponentially with distance from the boundary of a tissue because of energy dissipation after reflection. Penetration depth is defined as the distance in which the power density decreases by a factor of e^-2 (13.5 percent) and is a function of frequency and tissue properties. At higher frequencies, fields penetrate much less than at lower frequencies. For example, at 2.45 GHz (microwave oven frequency), penetration depth in tissue is about 2.0 cm, while at 10 GHz, it is about 0.4. At higher frequencies, any heating that occurs is primarily surface heating. Penetration depth for fat and bone is nearly five times greater than for higher-water-content tissues. At frequencies between 300 and 3000 MHz, electromagnetic energy can penetrate into more deeply situated tissues, making it especially desirable for therapeutic applications. Two properties of a tissue that determine how electromagnetic radiation is absorbed, are permittivity and conductivity. The permittivity of a tissue is a strong function of frequency, generally decreasing with increased frequency. The whole-body averaged value permittivity is approximately $\frac{2}{3}$ that of muscle tissue.

If the relative permittivity of the object is very close to one, very little scattering occurs. When an object is very small compared to the wavelength of the incident field, very little scattering occurs. When the size of the object is comparable to or larger than a wavelength, significant scattering occurs.

The conductivity of tissue is essentially that of its intra- and extracellular fluids. In general, the wetter a material is, the more lossy it is, and the drier, the less lossy. We see this daily in that a wet paper placed in a microwave oven will get hot only as long as it is wet, after which it will no longer absorb energy and not be heated. Muscle and high-water content tissues will absorb more than drier tissues such as fat and bone.

The time-averaged rate of energy absorption for steady-state sinusoidal fields per unit volume (W/m$^3$) at a point inside an absorber is P=sE$^2$ where is E is the root-mean-squared magnitude of the electric field vector at that point inside the material, and s is the conductivity.

Radiation by Antennas: The expected value of S (absorption) in W/m$^2$ with an antenna with gain G, receiving an input power P, at a distance r, is giving by S=PG/4(pi)r$^2$[2], where PG=ERP (effective radiated power). S is also known as the Poynting Vector. Gain is a measure of the ability to direct RF power in specific directions in comparison to an isotropic antenna, and generally specified in the far-field. In the near field gain may vary, which may be an issue in determining exposure limits. If antennas are propagating efficiently, there should be no field at the base of the antenna.

Specific Absorption Rate (SAR): Because the nature of the interactions between biological tissue and external radio waves is so complex, studies are done either through simplified theoretical models or experiments. Of course, the usefulness of these studies depends on the accuracy of the models and the instruments used to make measurements. Measurement of internal fields, however, is not possible in humans, and has only been done in animals. In order to determine hazardous exposure levels for man, it is therefore necessary to measure external fields. External fields which are dangerous for man are determined by measuring levels of harmful internal fields created in animals and then extrapolating to determine the corresponding external field that would cause that same specific absorption rate (SAR) in man.

Specific Absorption Rate (SAR) is the time derivative of the incremental energy (dW) absorbed by, or dissipated in an incremental mass (dm) contained in a volume element (dV) of a given density (r).

$$SAR=(1/r)(dW/dt)$$

where dW/dt is the rate of change of the energy per unit volume of charged particles at that point. The SAR is therefore expressed in watts per kilogram (W/kg).

Average SAR (or whole-body average SAR) is defined as the ratio of the total power absorbed in the exposed body to its mass, whereas the local SAR is the value within a defined unit volume or mass, which can be arbitrarily small.

The SAR does not fully characterize the internal fields created (e.g. it does not account for interactions directly through the H field or orientation of the E fields created), but it is a useful unit of measurement in dosimetric studies. For example, because knowing SAR gives a measure of the internal fields, which could possibly cause effects other than direct heating.

Measurement of SAR: The rate of temperature change of tissue in vivo is related to SAR by:

$$\Delta(T)/\Delta(t)=(SAR+Pm-Pc-Pb)/C$$

where $\Delta(T)$ is the temperature increase,
$\Delta(t)$ is the exposure duration,
Pm the metabolic heating rate,
Pc is the rate of heat loss per unit volume due to thermal conduction,
Pb the rate of heat loss per unit volume due to blood flow, and C is the specific heat of the tissue For short periods of exposure, this can be approximated as $\Delta(T)/\Delta(t)=(SAR)/C$ because presumably a steady-state existed before exposure and Pm−Pc−Pb=0. Measurements of SAR are often made using this formula because of its simplicity. Because the temperature must be linear with time, the fields must be intense enough that the temperature rise is not influenced significantly by heat transfer. Because there may be interaction between a thermometer and the field, new methods are being used to measure temperatures, such as thermography which uses an infrared meter to measure temperature over the entire surface.

Dependence of SAR on Orientation: There are three possible orientations to an electromagnetic wave:

E-polarization: the electric field is parallel to the major axis, cross-section of body perpendicular to the incident magnetic field is larger H-polarization: the electric field is perpendicular to the major axis, the magnetic field vector is parallel to the major axis and cross-section is smaller K-polarization: both electric and magnetic field vectors are perpendicular to the major axis.

In general, E-polarization produces the highest energy absorption for frequencies up to and slightly beyond the resonance region. This is because coupling between the body and the electric field is maximized in this orientation. This is due to the antenna-like properties of the body.

To be even more specific, the human body is an ellipsoid, not a spheroid, and hence has six polarizations, but these can be approximated by the three orientations listed above.

A person standing on a perfectly conducting ground plane (link to glossary) with E polarization experiences a resonant frequency approximately one-half that in free space, because the ground plane makes the individual appear about twice as tall electrically. Resonance frequency is then about 40 MHz Dependence of SAR on Size, Shape and Frequency: The frequency of maximal absorption is called the resonance frequency (for humans it is between 70 and 100 MHz), and depends on orientation with respect to the incident field. In general, the rule is that the shorter the subject, the higher the resonance frequency, and vice versa.

For maximum energy coupling (E-polarization defined above), the long-axis of the body is oriented in the direction of the electric field vector, i.e. the incident plane wave is perpendicular to the body. The resonance frequency generally occurs at a frequency for which the length of the body is about one half of a free-space wavelength. Below resonance, SAR is intermediate for K polarization, and least for H polarization. For frequencies such that the ratio of the longest body dimension (L) to the free space wavelength (l) is less than 0.2, the average SAR depends on frequency as $f^2$. The average absorption then goes through a resonance in the region where $0.2<L/l<1.0$. The average SAR increases to a maximum near $L/l=0.4$ and then decreases as $1/f$. When $L/l>1.0$, whole-body absorption decreases slightly but approaches the geometrical optics limit of about one half of the incident power asymptotically. This is shown in FIG. 13.

This resonant absorption length of 0.4 lambda agrees with results from antenna analysis. So for L=175 cm, maximum absorption occurs at about lambda=L/0.4=437.5 cm which is a frequency of 68.6 Mhz.

SAR is higher when the body is more perpendicular than parallel to an incident field. It is also higher when the cross section of the body perpendicular to the incident magnetic field is larger. So for E polarization SAR increases as an object becomes longer and thinner, and decreases as it becomes shorter and fatter.

Average SAR is highest at 0.25 W/kg at 70 MHz for humans for an incident power density of 10 W/m$^2$; at this frequency the average SAR for a rat is only 0.0125 W/kg. Average SAR is highest at 0.8 W/kg at 700 MHz for rats; for humans at this frequency, the SAR is less than 0.04 W/kg. It is thus crucial to take into account the body size and frequency of the external field to establish relationships between biological effects that occur in lab animals and the corresponding effects that might occur in humans at a given incident power density.

Near and Far Field Effects: The far field extends from a minimum distance of approximately 2D2/l, where D is the larger dimension of the antenna and l is the wavelength. In this region the electromagnetic field has a mostly plane-wave character, meaning that the E-field and H-field vectors are perpendicular, and are both also perpendicular to the direction of propagation. The magnitude of the E and H fields is equal in the far field, so only one of the two needs to be measured. Power density varies inversely as the square of the distance from the antenna. For RF exposure measurements in some types of antenna systems, the extent of the near-field is considerably less. For circular parabolic antennas, for example, the distance may be closer to 0.35D2/l.

In the near field, however, power density has an oscillatory dependence on distance from the antenna. Objects placed near the source of the field may have a strong effect on the nature of the field, a fact that becomes especially important in trying to obtain measurements. The far field can be approximated as a spherical wave that can in turn be approximated by a plane wave described below.

Spherical Wave: The wave fronts are spheres and propagate radially outward, with the magnitude of E and H varying as 1/r, where r is the distance from the source. They are otherwise, similar to plane waves at large r.

Plane wave: True plane waves do not exist but serve as a good model for waves in the far field. The wave fronts are planes, and E and H and the direction of propagation are mutually perpendicular. For free space E/H=377 ohms, and E and H are constant in any plane perpendicular to the direction of propagation.

Measurement of External Electrical Fields: Because it is difficult and impractical to measure internal electric fields, in general we must measure external fields and base exposure limits on these. Broadband instruments/survey meters are frequency independent sensitivity and measure integrated intensity of fields, with no frequency spectrum information. Narrowband instruments (e.g. spectrum analyzer) are selective and provide information about field intensity at a selected frequency. Personal Dosimeter attempts—the goal of such a device would be to measure the exposure of a person throughout their daily activities. The dosimeter is only capable of recording cumulative radiation, meaning the power density integrated over time. Biological effects are dependent on the dose rate, and not just on total dose (i.e. exposure to 200 mW/cm$^2$ for 10 min is not the same as exposure to 1 mW/cm$^2$ for 2000 min). The dosimeter is also partially shielded by the wearer. Measurement of internal fields is difficult but can be done with non-perturbing implantable probes. We can then get the SAR if the conductivity of material is known, and then only at a few points. Interference with other objects near the antenna, scattering or reflecting surfaces modulation characteristics of the radiation are important, accuracy of instruments, pulse shape and duration, and repetition rate.

Analytical and Numerical Models of Human Body Absorption: As an alternative to experimental methods, several different kinds of models can be used to predict SAR and heating effects. These include using finite element methods, Fourier transforms, convolution methods, and simplified spheroid models to make predictions without needing laboratory tests. Many of these primary coupling will be to neuronal bodies. More specifically to the dendrite spines themselves models have shown very accurate results.

The EHF and THz range of this invention is well beyond the frequency of maximum absorption. Power density of 2-10 mw/cm$^2$ are expected to be the range of maximum fluence.

Approach to Coupling MASER Energy to Brain Activity: In order to successfully couple adequately to a specified site in the encephalon or other organized tissue system, there are a limited variety of modalities. Discussed herein are exemplars of several processes.

The simplest of these modalities is the focusing of a single emission to a resolvable point at which the fluence of the energy overcomes the dissipative modes of the target. In typical optical systems the energy is diffracted, refracted, or reflected from a geometric lens, (Fresnel, composite, curved, hyperbolic, parabolic, compound etc.) through low-scattering and semi-transparent tissue in progressively smaller spot sizes. The smallest resolvable spot is blurred by diffraction limits related to the wavelength of the energy, the geometric precision of the optics, and the scattering effects of the media (tissue). This continues until the target point, at which, a calculated coupling through thermal, Rabi, electromagnetic, absorption and less prominent processes overcomes the scattering and dissipative effects. The type of coupling lends itself to energizing type of interaction. It is gross in effect and almost always results in thermal enhancement. In therapeutic systems, the thermal effects agglomerate, coagulate and/or denature proteins, resulting in a localized necrosis and subsequent clearance of the tissue by physiologic mechanisms. Other effects which are typically limited to shorter wavelength energies include depolarization and ionization. Almost always this leads to cellular death and occasionally viable mutation. Typical focusing systems are limited in precision due to accessibility to the target, spatial discontinuities in the structures, scattering, and geometric precision. Target volumes under several millimeters are not resolvable.

In contrast to the finesse of focused systems are directed energy mechanisms. Directed energy systems include particle beams and gamma sources. These are used in treatment modalities called radio surgery. Included in these systems are implantable radiation beads, Proton Beams and Gamma Knives.

Referring to FIG. 14, radiosurgery therapeutically functions by the selective ionization of tissue through irradiation by high-energy beams of radiation. Ionization is the production of ions and free radicals which are damaging to the cells. Typically, shell electrons are accelerated by absorbing energy from both particulate kinetic transfer and relativistic oscillatory energy. With a surplusage of energy these electrons exceed the binding force of the nucleus and are freed. Devoid of a balance of charge, these atoms are positively ionized and will react substantially differently to the adjacent atoms or molecules. Moreover, the energetic electron that escaped from the atom participates in electronic current and may contribute to other interactions. These ions and radicals, which may be formed from any of the available ground state atoms in the target cell or biological materials, can produce irreparable damage to DNA, proteins, and lipids, resulting in the cell's senescence or death. By this means, biological action potential and activity is ameliorated within a given volume of tissue by the radiation delivered to the target is measured in grays. A gray "Gy" is the absorption of one joule of energy per kilogram of mass. The direction of the energy is by shielded aperture masks (see accompanying FIG. 1). Even with precision stereotaxis, accuracy is limited. Fortunately, given the lack of scattering and the multiple conflations of energy beams, stability of energy delivery is well understood. Precision in these systems is on the order of a plurality of cubic millimeters. It is noteworthy to state that the use of radiosurgical mechanisms may result in unwanted mutations that may not be senescent or dormant and give rise to neoplastic tumors. This outcome is an ever-present concern in systems using ionizing radiation such as X-rays.

Of greater interest in precision delivery of energy is selective absorption. The precise and selective delivery of energy into tissues represents a critical requirement for therapeutic devices. Intelligent delivery systems that are responsive to a single internal or external stimulus often lack sufficient selectivity, which compromises the efficacy and induces undesired side effects. To overcome this dilemma, photodynamic sensitization is used. In this methodology, a specific absorber is tagged to the tissue of interest. The gross volume of tissue is bathed in a very narrow frequency range of energy which selectively couples exclusively to the tissue that has incorporated the photo-absorber. Typically, this will result in a thermal or photo-catalyzed reaction that will denature the cell. Challenges exist as to how to target non-atypical cells. Even atypical cells merely are faster absorbers and therapy must be precisely regulated.

Further of great concern, is the long-term effect of exposure to ionizing radiation. While the target volume receives a dose orders of magnitude greater than the non-targeted volume, the overall energy of the absorption for a singular ionization event is the same all over. Therefore, while the statistical likelihood of a mutagenic effect is lower, the significance of the singular event is ever-present. It is evident that a non-transcription repairable event will occur, and such event will normally result in senescence, there is a non-trivial expectation that a viable mutagenic event is passed along resulting in new disease. Invasive Coupling. Neuromodulation is a technique for changing neuronal activity to achieve a therapeutic effect. The most relevant example of invasive modulation is deep brain stimulation (DBS) and noninvasive stimulation is TMS. The advent of stereotactic surgery in the 1960's allowed for relatively precise lesioning of deep brain structures. Among the more common procedures was stereotactic ablation of a portion of the thalamus—called thalamotomy to treat essential tremor. In these procedures, a lesioning electrode, measuring about 1 mm in diameter and having a 5 mm non-insulated tip, was used to create a thermal lesion measuring about 5×7 mm. Prior to making the lesion, surgeons would stimulate 130-18 Hz to confirm the location of the electrode tip. If the tremor was ameliorated, then the electrode was in the right spot. Lesions are not reversible, and the actual size is variable. This led to the idea of using a permanently implanted electrode stimulating at the same frequencies—DBS.

Initially, DBS was thought to be a functional lesion—essentially silencing the neurons—since the effect was the same as an ablation. However, simultaneous recording and stimulation revealed that was not true. DBS may reduce or entrain neuronal firing but does not silence an area. Modest changes are often sufficient for achieving the therapeutic effect. However, DBS surgery is invasive and carries a small but non-trivial 5-10% risk of hemorrhage and effectively only two electrodes can be placed.

In contrast, the energy band of a system constructed in accordance with an exemplary embodiment of the invention is well below the ionization threshold of molecules within the brain or other biological tissues. The system can "energize" or enervate neurons, which effectively means increasing or decreasing the probability of neuronal firing within a specific volume. Individual neurons are noisy (stochastic) and neuronal activity is best described using probability density functions. The average signal-to-noise or information transmission of firing rates improves greatly as the number of neurons increases and there is considerable redundancy of neurons in the cortex and subcortical nuclei (~15000 neurons per $mm^3$). Hence changing the probability of firing in a volume of neurons is the appropriate goal and would have a significant effect on the signals being transmitted.

The disclosed system modulates the probability of neuronal activity by coupling of microwave energy to transitions of molecules. Molecules have vibrational modes which correspond to conformational isomerization. These are configurations the molecules can adopt just by rotations about formally single bonds without breaking covalent bonds. The population distribution of conformational isomers depends on electrostatic factors and steric factors, but also on orbital interactions. The transition frequencies for many biologically relevant molecules are in the infra-red and microwave portion of the spectrum including saccharides, peptides, neurotransmitters, and amino acids.

Saccharides: One mode involves coupling to transitions of saccharides such as glucose—the primary energy source for neurons. These molecules have multiple conformations with transition frequencies (energies in the microwave range (Alonso et al, 2019; see FIG. 15). These conformational profiles have only been recognized recently. One goal of the invention is to enable the use of the MASER system to preferentially bias the glucose molecules within a volume to a less biologically available conformation, transiently decreasing the amount of glucose available to neurons and reducing their activity. With acutely reduced levels of glucose, neurons become less active but are viable for some period of time 5-10 minutes Neurotransmitters: Another goal of the invention involves coupling to neurotransmitters such as glutamate, GABA, dopamine and serotonin. As with the saccharides, catecholamines have very recently been found to have multiple conformations with dopamine, noradrenaline, and adrenaline, having 7, 8, and 11 conformers respectively (Cabezas, et al, 2020). In this mode, energy coupling via the MASER system is used to bias the population of dopamine molecules, within a volume, toward either more or less biologically active conformers, with resultant effects on the activity of post-synaptic neurons having G-protein coupled dopamine receptors. Similar strategies can be used for other neurotransmitters.

Amino Acids: Amino acids are the building blocks of protein chains found in Ion channels and G-protein coupled receptors. They play a critical role in large conformational changes of channels and receptors. Moreover, it has recently become clear that interconversion between specific conformations of amino acids found in ligand-gated channels are important in either facilitating or blocking ion flow. Viable conformations have been found for the amino-acids: Glutamate, Tyrosine, and Arginine, among others.

Ion Channels & G-protein coupled receptors: Another mode involves coupling to amino-acids in relevant trans-membrane molecules important for neuronal signaling which include Voltage-gated ion channels (Na+, K+, Ca++) that are responsible for the initiation, propagation and termination of action potentials, Ligand-gated ion channels that mediate the effects of excitatory neurotransmitters such as Glutamate and Acetylcholine along with inhibitory neurotransmitters such as GABA, and G protein-coupled receptors including those for dopamine, serotonin, epinephrine, and endogenous endorphins or exogenous opiates such as morphine and fentanyl. Recent work on pentameric ligand-gated ion-channels gated ion channels, whose different subtypes are important in allowing cations ($Na^+$ or $K^+$) or anions ($Cl^-$) to enter the cell, demonstrated that interconversion between specific glutamate and alanine rotamers was important in allowing a protein side chain to keep the channel closed or to allow ions through the pore. FIG. 16 shows data of the physical differences that occur with a conformational change in the a1-GluCL channel.

Another mode involves coupling to molecular targets associated with patterns of excessive neuronal activity or exaggerated cortical oscillations. Interconnected neurons that are active at the same time may exhibit Long-Term Potentiation (LTP), which is important in learning and memory, providing the means for linking various stimuli. Once established, LTP is maintained by occasional but less frequent co-activation of involved neurons. In the absence of expected co-activation, long-term potentiation will slowly decays back to a baseline. Particular patterns of excessive neuronal activity are associated with addiction to substances and behaviors along with neuropsychiatric illnesses such as Addiction, Major Depression, PTSD, and OCD. Recurrent experiences with the addictive substance, behavior, proactive stimuli, or compulsion reinforce and maintain the abnormal potentiation. Coherent oscillations represent simultaneous activity across many neurons. Beyond a certain point, oscillations become self-reinforcing. In Epilepsy, pathological theta band oscillations arising from one area can potentiate or stimulate other areas into becoming independent seizure foci. Hence one aspect of the invention is to prevent or minimize recurrent potentiation of pathologically excessive evoked neuronal activity or abnormally prominent cortical oscillation across multiple treatment sessions. This therapy promotes the decay of established and pathologic patterns of potentiation, allowing neurons and circuits to return to their premorbid patterns of activity.

Electromagnetically Induced Transparency: One method for coupling is derived from recent descriptions of a phenomenon called electromagnetic induced transparency (EIT). Referring to FIG. 17, consider a three-state system having a ground state G, an excited state E, and an intermediate state N. Transitions can occur between states but dipole transitions are forbidden between the ground state and the intermediate state, see FIG. 17A. Transition from Ground to Excited has an associated frequency and Excited to intermediate has a different frequency. There are two coherent electromagnetic beams directed at the system: The couple beam with angular frequency couples the Excited to intermediate transitions, while the probe beam probes the Ground state to Excited state transition. If the couple beam is switched off (FIG. 17B) while the frequency of the probe beam is varied one would expect an absorption profile around the resonance frequency, as illustrated in FIG. 17B. If the couple beam is turned on (FIG. 17C) at the resonance frequency of transition Excited to intermediate, a peculiar phenomenon occurs: A tiny transparency window opens around the resonance frequency, reaching a transmission of nearly 50% in an otherwise opaque surrounding. This effect was first observed in Strontium vapor. This means that a medium can be made transparent for a certain frequency by switching two beams. The explanation for this phenomenon lies within the afore-mentioned Rabi cycle. If the coupling beam is at the same frequency as the excited to intermediate transition, oscillations between state intermediate and excited states are fully modulated and occur at the Rabi-frequency, which has two important implications: 1) Integrated over time, the resonant condition results in the greatest probability for finding the system in the excited state. 2) Since the two transitions share the same excited state, the resonant transition, and by extension the whole 3-state system, is fully entrained in oscillating between the Excited and Intermediate state, resulting in a destructive interference with the other transition. Hence when the probe beam is at the frequency of the other transition from state Ground to state Intermediate, photons at the transition frequency between the Ground state and the Excited state, cannot interact with the substance, and are transmitted straight through, as if it were transparent.

EIT Cooling: The phenomenon of EIT was predicted theoretically and first demonstrated in Strontium vapor. However, the same type of system can be used for cooling or heating as depicted in FIGS. 18A and 18B. The three-state system is the same as before. In this case, we will change the name of the probe beam to a modulatory beam.

The coupling beam is only slightly detuned and above the resonance frequency while the modulatory beam is more detuned and below the resonance frequency. Neither state is fully entrained, and consequently the probability of being in one transition is higher than the other. In this case, the system can be biased to absorb photons and oscillate between the intermediate and excited frequency, though there exists a low but real probability of decaying to the lower energy ground state. The quantum of energy released in decaying to the ground state, is larger than that gained in the transition from intermediate to the excited state. Over multiple iterations, this leads to significant cooling. The same type of system can also be used for heating. If the coupling beam is adjusted to optimize photon absorption at the Ground to excited frequency and the modulatory beam to preferentially decay to the intermediate resonance, there is greater energy absorbed from the photon than released in the decay, and the net result is heating. This approach was first demonstrated using lasers to cool calcium ions.

In one aspect, the invention builds on this approach in multiple innovative ways. A practical example is helpful. Recent work on the acetylcholine nicotinic receptor (ACHNR), a ligand-gated ion channel allowing Na+ to enter the cell, demonstrated that interconversion between specific glutamate rotamers was important in allowing a protein side chain to keep the channel closed or to allow Na+ into the pore.

Consider the situation where one of these glutamate rotamers has a transition outside the frequency range of the MASER when the channel is closed, but inside the range when the channel is open. When the channel is closed, there would be no change in the detected frequency. However, when the channel is open, this transition becomes apparent as an absorption profile during the time it was open (FIG. 19A).

Referring to FIG. 19B, the system can be programmed so that upon detection of this pattern, a modulation beam is applied at a detuned frequency so as to minimize the probability of this transition, preferentially keeping the channel closed. Alternatively, the beam could be tuned to maximize the probability of this transition keeping the channel open. Either one could disrupt the function of the channel and potentially the neuron by impairing their ability to participate in neuronal signaling.

There are multiple channels and receptors which function in a well known sequence: Iontropic Glutamate receptors generate excitatory post-synaptic potentials, Voltage-gated Na channels then initiate an action potential, voltage-gated K+ channels which terminate an action potential, and voltage-gated Ca++ channels cause transmitter release. Any of these are potential targets. Moreover, since they activate in stereotypical manner, an absorption profile seen later in the sequence can be used as a reporter to indicate whether modulation of an earlier event was successful. Subsequently, these can be modulated in combination to maximize the effect.

It is also possible to use the principle of EIT cooling or heating to modulate neuronal function. Experimental studies in primates using implanted cooling coils have demonstrated that cooling the cortex within to about 20 degrees Celsius silences the area but is reversible and does not cause any permanent damage.

The system may also be used to permanently necrotize localized tissue by selectively heating or cooling it beyond the range of reversibility (heating to 50 degrees Celsius or cooling to 0 degrees Celsius). The nearly instantaneous coupling will allow for extremely rapid heating or cooling of a target much faster than the targets ability to kinetically transfer the energy either out of or in. In addition, cells can be induced to undergo programmed cell death, or apoptosis, under a variety of circumstances such as a sustained imbalance between energy demands and the availability of glucose and oxygen. In one contemplated use, Inotropic glutamate receptors are biased toward staying open, causing irreversible ecotoxic injury to cellular mechanism. In another contemplated use, glucose molecules in a particular volume of the brain are biased toward biologically unfavorable conformations limiting their availability and eventually resulting in energetic exhaustion and cellular death. In certain disorders such epilepsy, the most definitive treatment is resection or ablation. The disclosed system provides a means for noninvasive ablation of seizure foci, where none currently exist.

The brain contains neurons and glia (astrocytes and oligodendrocytes, all three of which are derived from the same progenitor cells. Neurons are post-mitotic and stop dividing in infancy, while glia continue divide throughout life. Like neurons, glia have membrane potentials, voltage-gated ion channels, ligand-gated ion channels, and g-protein coupled receptors, though glia do not fire action potentials and hence changes in activity occur at a slower rate. Glia work in concert with neurons to regulate the concentration of extracellular $Na^+$, $K^+$, $Ca^{++}$ ions, maintain the blood brain barrier and clear neurotransmitters from the extracellular compartment. Glial cells have neither dendritic trees nor axons and exhibit different distributions of transmembrane channels and receptors. These factors allow for the differentiation between glial and neuronal cells.

Glia can acquire mutations leading to unregulated cell division and neoplastic growth. The vast majority of primary brain tumors are glial and the most common glial tumor is also the most aggressive—Glioblastoma (GBM).

Glioblastoma often has areas of solid tumor, composed almost exclusively of neoplastic glial cells without interposed neurons, along with areas of adjacent brain tissue that remain functional but are infiltrated by malignant astrocytes. In most cases, but not all, surgery is effective in removing the solid tumor. However, surgery cannot remove infiltrating cells in the surrounding brain, which inevitably leads relapse and the demise of affected patients. Devising an effective therapy for infiltrating cells has been vexingly difficult: Most chemotherapeutic agents do not cross the blood brain barrier; Immune modulators are not as effective in the brain which is "immune-privileged", hence lacking many cell types needed to mount an effective immune response; Radiosurgery is suited for small well-circumscribed tumors (less than 3 cm), but not for GBM's, which are large and have indistinct boundaries. The average survival for GBM patients has remained stuck at 12-18 months for more than 40 years.

The disclosed system can be used to noninvasively and selectively cause necrosis of tumor cells, including GBM, based on their differential interference patterns and activity maps. Malignant transformation of glial cells is associated with amplification/overexpression of oncogenes (e.g, p53), along with the loss of tumor suppressor genes (e.g, RB1) and DNA-repair genes. These changes result in uncontrolled proliferation. Malignant astrocytes also overexpress a number of receptor subtypes including the Interleukin 13 receptor (IL-13RA2) and the Ephrin receptor (EphA2). Malignant astrocytes exhibit elevated rates of metabolic activity compared to normal glia or neurons. In solid portions of tumor, the multiplication rate exceeds the local blood supply, thereby limiting the availability of Oxygen, forcing malignant cells to utilize anaerobic metabolism. Collectively, these changes result in over-expression of transcription factors, receptors, and metabolic enzymes. Hence the associated molecular signature is vastly different from normal glia and neurons. In one aspect of the invention, the disclosed system can be used to induce necrosis in otherwise unresectable tumor cells involving the brainstem, thalami, or basal ganglia.

Infiltrating tumor cells also have abnormal expression of transcription factors, receptors, and metabolic enzymes. The high spatial resolution of the disclosed device allows for the identification of discrete differences in the interference pattern and activity mapping associated with individual tumor cells and the use of one or more techniques (heating, cooling, excitotoxic, or energetic exhaustion) for inducing necrosis of tumor cells. Another aspect of the disclosed invention is the use of target molecules found exclusively, or almost exclusively, on tumor cells such as the IL-13RA2 and EphA2 receptors, without explicitly targeting individual cells. Given the specificity of coupling to particular molecules, it is possible to treat the whole brain so that only cells expressing malignant molecular phenotypes are targeted, while normal neurons and glia not expressing such molecules are unaffected by the therapy.

SUMMARY OF THE INVENTION

In one aspect, the invention pertains to a process for utilizing low-power (2-10 Watts), continuous wave, coherent mode-locked anisotropic MASER radiation, to noninvasively record molecular activity in the brain and other extensions of the central nervous system and thereby provides data for the production of an energy activity map of specific molecular targets. In another aspect, the invention also can be used to neuromodulate by enervation or energization or to cause cellular necrosis in specific targets in the brain. It is contemplated that the invention be used to record and modulate brain activity, or to record from and modulate other biological tissues or objects besides the human brain. It is expected, however, that the invention will be most useful when applied to record brain activity and/or modulate molecular targets within the brain.

The method of activity mapping uses a real-time MASER diffraction-limited interferometer. As a first step, a beam of coherent MASER radiation is created by an emitter array and passed through a collimator. The collimated MASER beam is split into a probe beam and a reference beam. The probe beam passes through a head and a brain of a patient creating a post-engagement beam and simultaneously the reference beam is passed through a uniform substance resulting in a delay of the reference beam similar to that caused by the probe beam's traverse through the head. The delay generates a lagged reference beam. The lagged reference beam and the modulated probe beam are combined to create a convolved beam characterized by a time-shifting interference pattern. The time-dependent interference pattern in the convolved beam is detected by a detector array, and the interference pattern is deconvolved to quantify changes in phase, modulation, amplitude, and lag between the post-engagement probe beam and the lagged reference beam. This information is then used desirably to generate, time-shifting, 3-dimensional energy activity maps of the brain. This energy activity mapping can then be associated with a physical image of the brain taken via MRI or CT scan.

In the exemplary embodiment, the beam of coherent MASER radiation is generated from a phased emitter array using synthetic aperture techniques. In particular, the emitters and the phased array are constructed in accordance with the teachings in the above incorporated, co-pending application Ser. No. 17/148,215, entitled "Thin Film MASER Emitter and Thin Panel Phased Array of Emitters," by James Joseph Cohen and Emad N. Eskandar, filed on even date herewith. The incorporated co-pending patent application describes a unique combination of thin epitaxial diamond film implanted with nitrogen ions in combination with other component layers to enable the fabrication of a thin panel, phased-array of MASER emitters, which uses Q-switching to form a mode-locked continuous wave MASER beam.

Also, in the exemplary embodiment, the interference pattern formed by the convolved post-engagement and lagged reference beam is detected by a phased array of detectors again using synthetic aperture techniques. In particular, the detectors and the phased array are constructed in accordance with the teachings in the above incorporated, co-pending application Ser. No. 17/148,275, entitled "Phased-Array MASER Detector for Synthetic Aperture Interferometric Imaging," James Joseph Cohen and Emad N. Eskandar.

A system configured in accordance with the invention has the capability to map brain activity at high levels of spatial (potentially 0.3 microns or better) and temporal (potentially 10 nanoseconds or less) resolution with differential resolution of about 100 femto-seconds. For comparison, neuronal cell-bodies range in size from about 10 to 50 microns while changes in neuronal firing rates occur in the millisecond range. Hence, the system can provide information about neuronal activity at the cellular and potentially sub-cellular level. The system is not a traditional imaging modality, though it has parallels to such systems having emitter and detector arrays. At large scale, it may be considered a topological energy mapping and recordation system since it has the potential to capture neural activity changes with a spatial and temporal fidelity that matches or exceeds that of penetrating electrodes.

In another aspect, the invention can be used to energize or enervate molecules with targeted signature receptors. The system can be operated to activate or inactivate multiple discrete brain or axonal targets with the same spatial and temporal precision as used for energy activity mapping. The energy activity maps provide both the basis for potential manipulation, and the measure of its success. Hence, at scale, combining the two functions creates a closed-loop adaptive, noninvasive neuro-modulatory system. In this regard, the system implements a method of transferring energy via MASER radiation to one or more targeted molecules at a specified point in time within a biological object, such as the brain or the body or a part of the body. First, a mode-locked beam of coherent MASER radiation is emitted by the emitter array and passed through a collimator. Then, the mode-locked MASER beam is optionally passed through a photonic modulation plate and then through an object in which one or more targeted molecules are expected to reside, based on the mapping function. The phase of the mode-locked MASER beam is shifted by controlling the Q-switching of the phase emitter array and/or by the photonic modulation plate in order to Rabi couple the mode-locked MASER beam to said one or more targeted molecules in the object. This results in transferring energy from the mode-locked MASER beam to the respective Rabi coupled signature targets. The energy absorption is used to change the state of the molecule targets. For example, the system can be used to bias dopamine, glutamate, acetylcholine, GABA or other neurotransmitters toward conformations that are less favorable in activating associated receptors, within a particular volume of brain. In addition, the system can be configured to favor certain conformational transitions in trans-membrane voltage-gated ion-channels, trans-membrane ligand-gated ion-channels, or G protein-coupled receptors, thereby impairing or enhancing their function.

It is contemplated that the brain be actively mapped intermittently while transferring energy via MASER radiation to said one or more targeted signature receptors, as mentioned above to create a closed-loop adaptive noninvasive neuro-modulatory system. The transfer of energy can be controlled to activate or inactivate specific volumes in the brain or in some applications to disrupt targeted molecules so as to cause cellular necrosis. On the other hand, intermittent activity mapping may not be necessary in all applications, such as whole body scans of low-level radiation to enervate signature biological targets. Such an application can be envisioned in the treatment of a widespread illness, for example systemically modulating ACE2 receptors toward a conformation that is less favorable to binding by the spike protein on SARS-CoV2—the virus causing COVID-19 illness.

Contemplated embodiments of the invention have the ability to collect discrete information on action-potentials arising from neurons and travelling in axons, with enough spatial specificity to create a virtual activity map overlay. Further, other contemplated embodiments have the ability to couple energy into neuronal molecules for either activation or inactivation. Finally, embodiments that are able to ablate brain lesions such as neoplasms based on their molecular activity patterns providing a more precise and less harmful technique than ionizing radiation, are also contemplated.

One object of the invention is to provide a MASER interferometer suitable for use in biomedical activity mapping of the brain. The dynamic interferometer is fabricated using the MASER emitter panel array, a beam splitter, a beam integrator, and the MASER detector panel array.

Another object of the invention is to use a MASER interferometer for the biomedical imaging of the brain and of other components of the central nervous system. The dynamic interferometer is fabricated using the MASER emitter panel array, a beam splitter, a beam integrator, and the MASER detector panel array Another object of the invention is to provide the capability of using real-time deconvolutional hardware and software to capture changes in the interference pattern at a direct resolution of 10 nano-seconds and differential resolution of as low as 100 femtoseconds.

Another object of the invention is to provide a system for large scale recording of neuronal brain activity at sub-micron granularity.

Another object of the invention is to provide a system for large scale recording of neuronal brain activity with a temporal resolution of 100 femto seconds.

Another object of the invention is to provide the capability of using MASER dynamic interferometry to record inferred changes to quantum states of sodium and potassium ions, changes in the conformation and energy states of biological molecules such as ion channels, changes in the molecules and membrane potentials of neuronal dendrites, soma, and axons.

Another object of the invention is to provide a method for recording changes associated with the neuronal and axonal firing of action potentials.

Another object of the invention is to provide a method for recording changes in the activity of groups of neurons previously observed using electrical recordings as oscillations in the delta (~1-5 Hz), alpha (6-12 Hz), beta (13-25), gamma (26-50 Hz) and high gamma (51-500 Hz).

Another object of the invention is to provide the use of MASER Dynamic Interferometry to study, characterize, and understand activity patterns associated with normal sensory functions of the brain including but not limited to vision, audition, somatosensory perception, olfaction, and gustatory responses.

Another object of the invention is to provide of the capability of using MASER Dynamic Interferometry to study, characterize, and understand activity patterns associated with normal output functions of the brain including but not limited reflex movements, simple volitional movements, complex sequences of movements and patterns of behavior.

Another object of the invention is to provide the capability of using MASER Dynamic Interferometry to study, characterize, and understand activity patterns associated with normal cognition including but not limited to learning, short-term memory, long-term memory, conflict resolution, social behavior, subjective decision-making and objective and decision making.

Another object of the invention is to provide the capability of using MASER Dynamic Interferometry to study, characterize, and diagnose activity patterns associated with behavioral, psychiatric, and neurological brain disorders.

Another object of the invention is to provide of the capability of using MASER enervation of the brain for therapeutic purposes by using MASER beams modulated to de-energize or enervate specific brain targets and dissipate energy through Rabi coupling, for the treatment of brain disorders.

Another object of the invention is to provide the capability of using MASER activation to energize focal brain areas for therapeutic purposes through modulated MASER beams, so they are coupled to energize specific brain targets through Rabi resonant coupling.

Another object of the invention is to provide the capability of using MASER enervation and MASER activation, in isolation or in combination promote disruption and absorption of protein aggregates including but not limited to α-synuclein in Parkinson disease and β-amyloid in Alzheimer disease.

Another object of the invention is to provide the capability of using MASER Dynamic Interferometry to study, characterize, and understand activity patterns associated with primary brain tumors such as Glioblastoma and the surrounding brain tissue.

Other objects and features of the described invention are discussed in the Detail Description and still others may be apparent to those skilled in the art upon reviewing the drawings and the description thereof.

BRIEF DESCRIPTION OF THE DRAWINGS

FIG. 18A demonstrates a three-state system with coupling and modulatory beam frequency tunings chosen to dissipate mechanical energy or heat, thereby resulting in cooling.

FIG. 18B demonstrates the same system as in FIG. 18A but now with coupling and modulatory beam frequency tunings chosen to accrue mechanical energy thereby energizing or heating the system.

DETAILED DESCRIPTION

Figure 1:
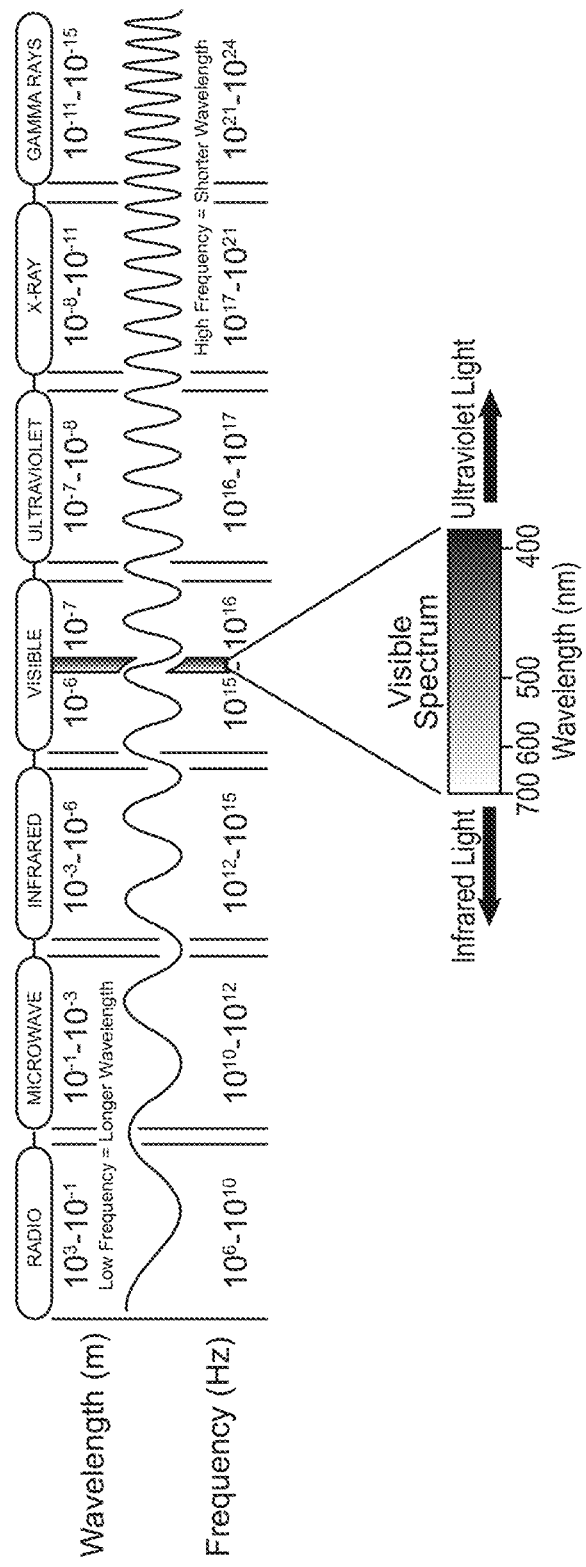
FIG. 1 is a diagram illustrating wavelength and frequency along the electromagnetic spectrum.
Figure 2A:
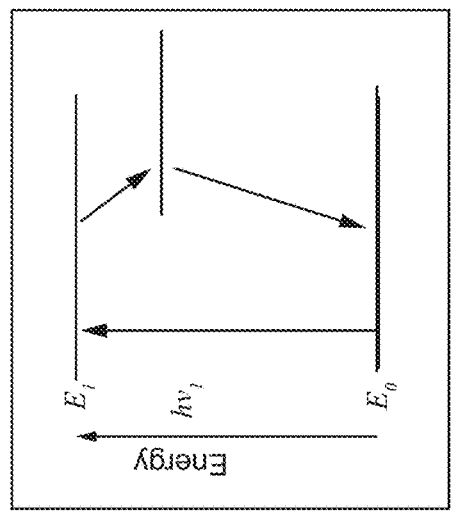
FIGS. 2A and 2B are Jablonski diagrams illustrating the relaxation of a molecule or atom to a lower energy state through emission of photons (FIG. 2A) and relaxation of a molecule or atom to a lower energy state through loss of heat and photon emission (FIG. 2B).
Figure 2B:
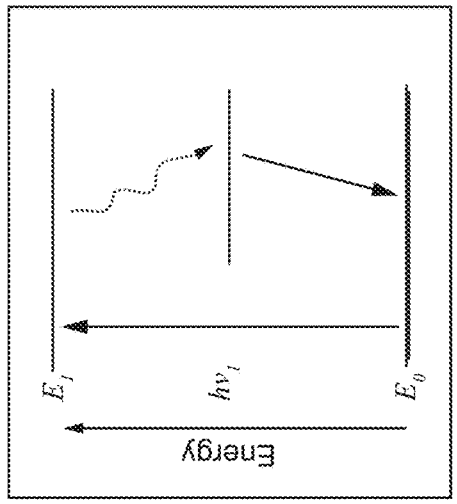
Figure 3:
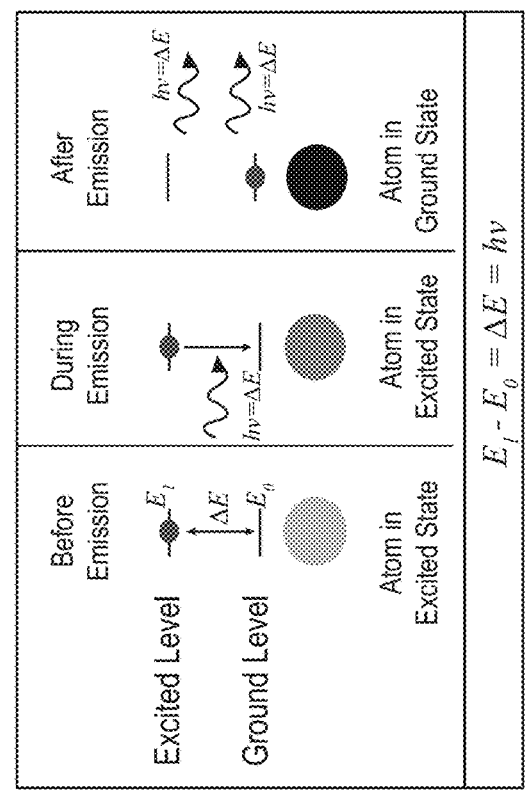
FIG. 3 is a diagram illustrating stimulated emission.
Figure 4:
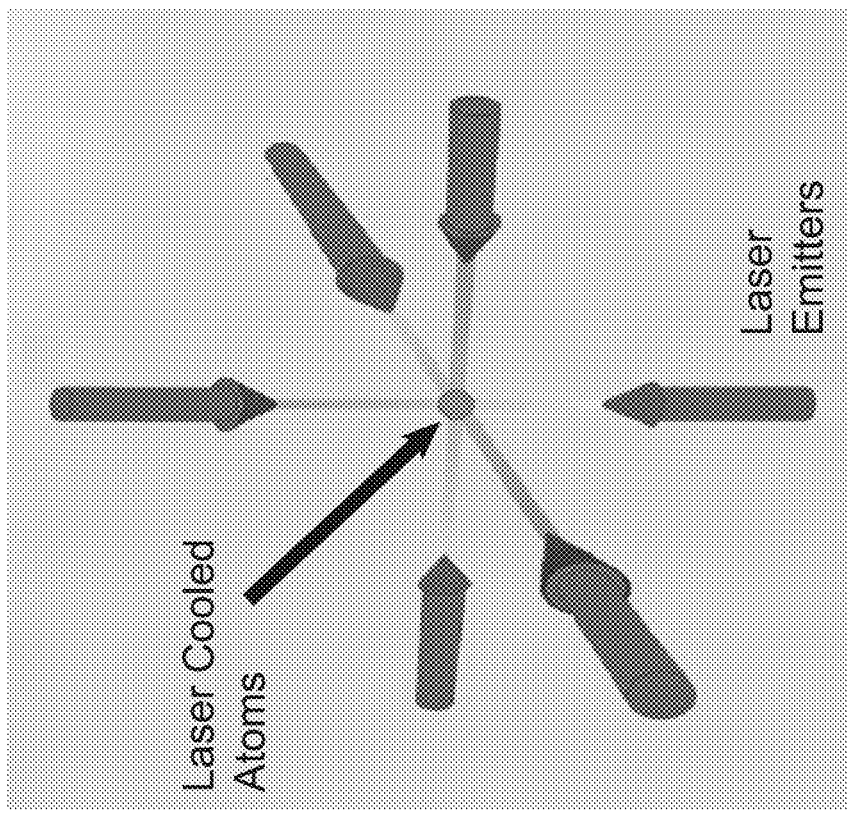
FIG. 4 is a schematic illustration showing doppler cooling by LASER radiation.
Figure 4:
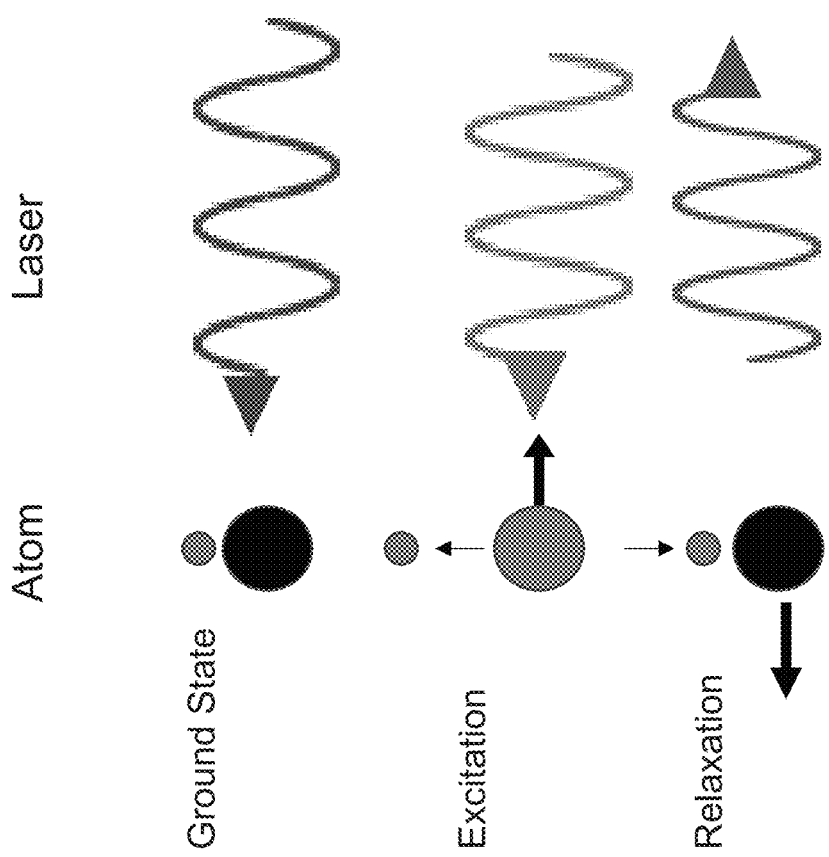
Figure 5:
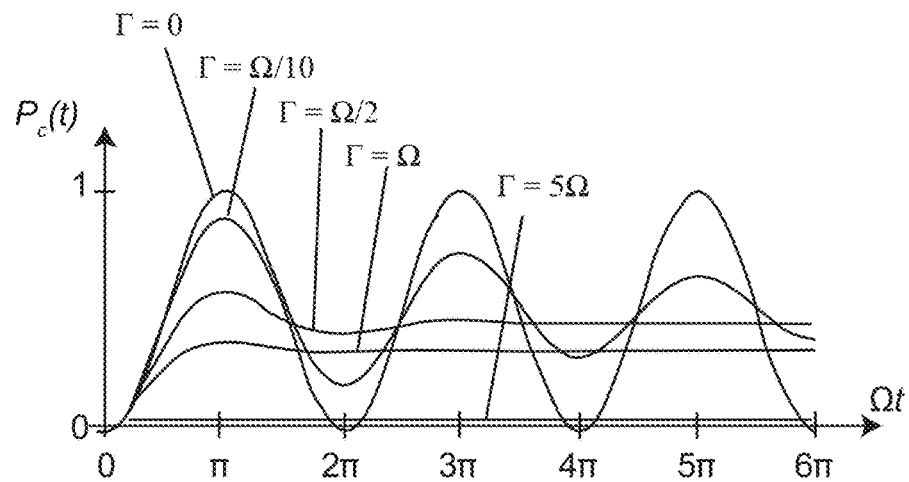
FIG. 5 is a plot illustrating Rabi probability at various frequencies.
Figure 6:
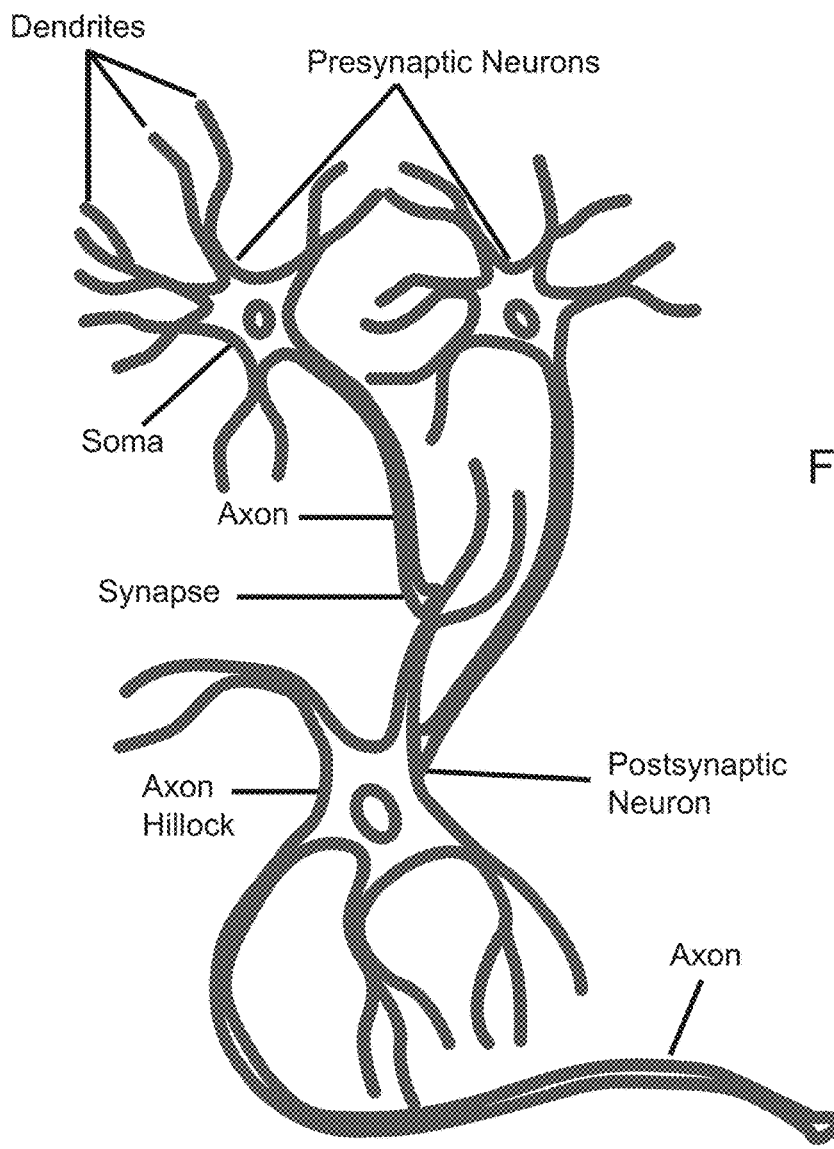
FIG. 6 is a schematic illustration of presynaptic neurons.
Figure 7:
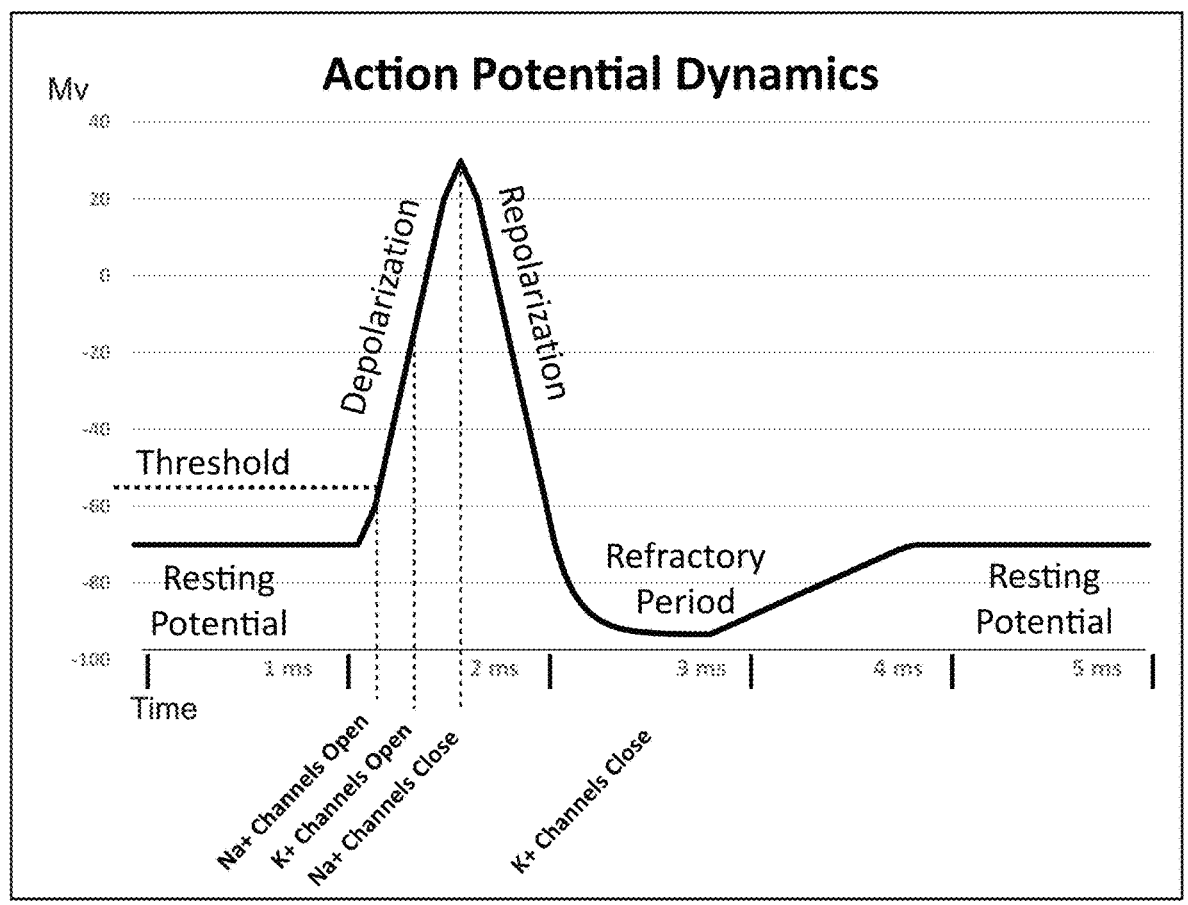
FIG. 7 is a plot of synaptic action potential.
Figure 8:
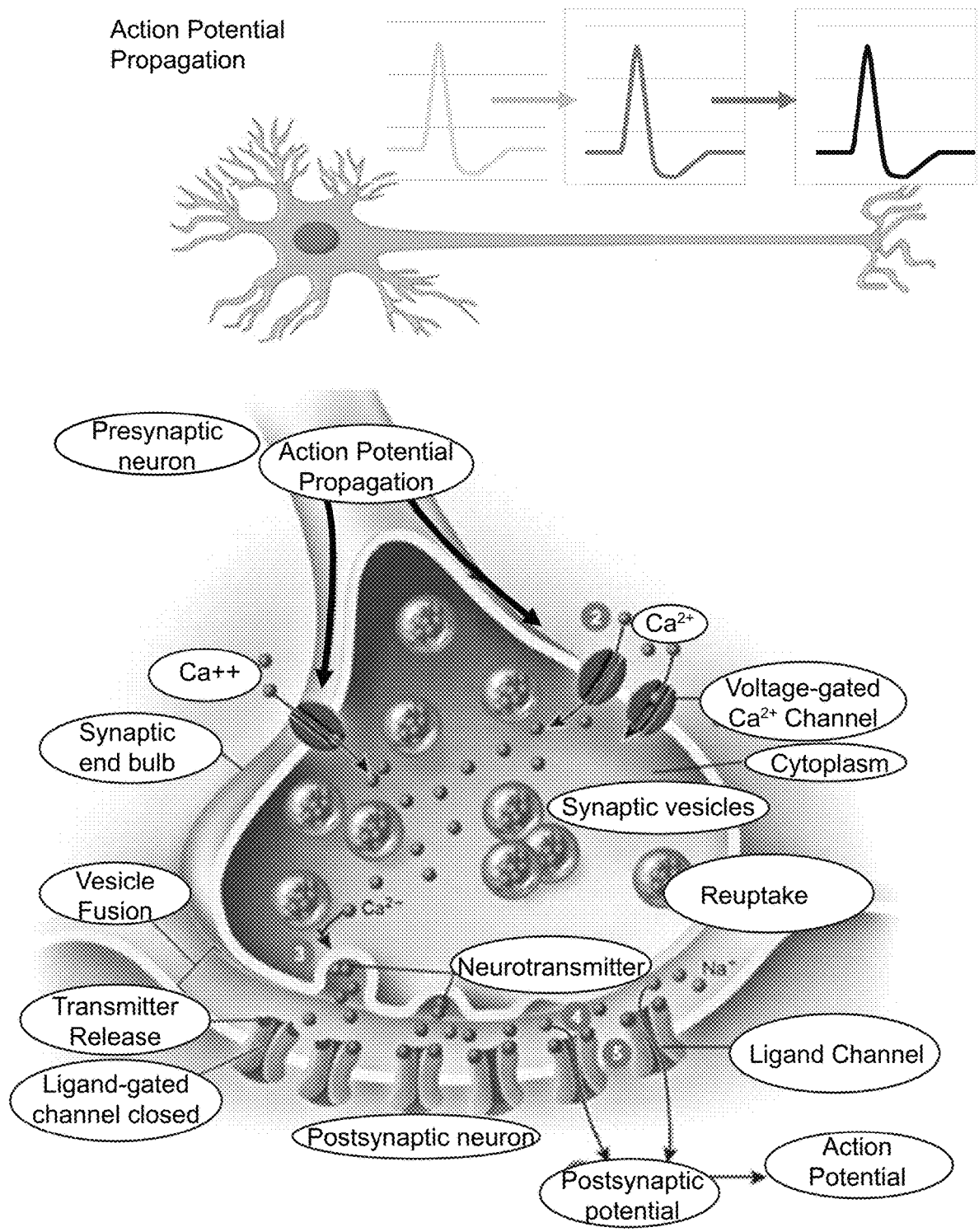
FIG. 8 illustrates synaptic transmission.
Figure 9A:
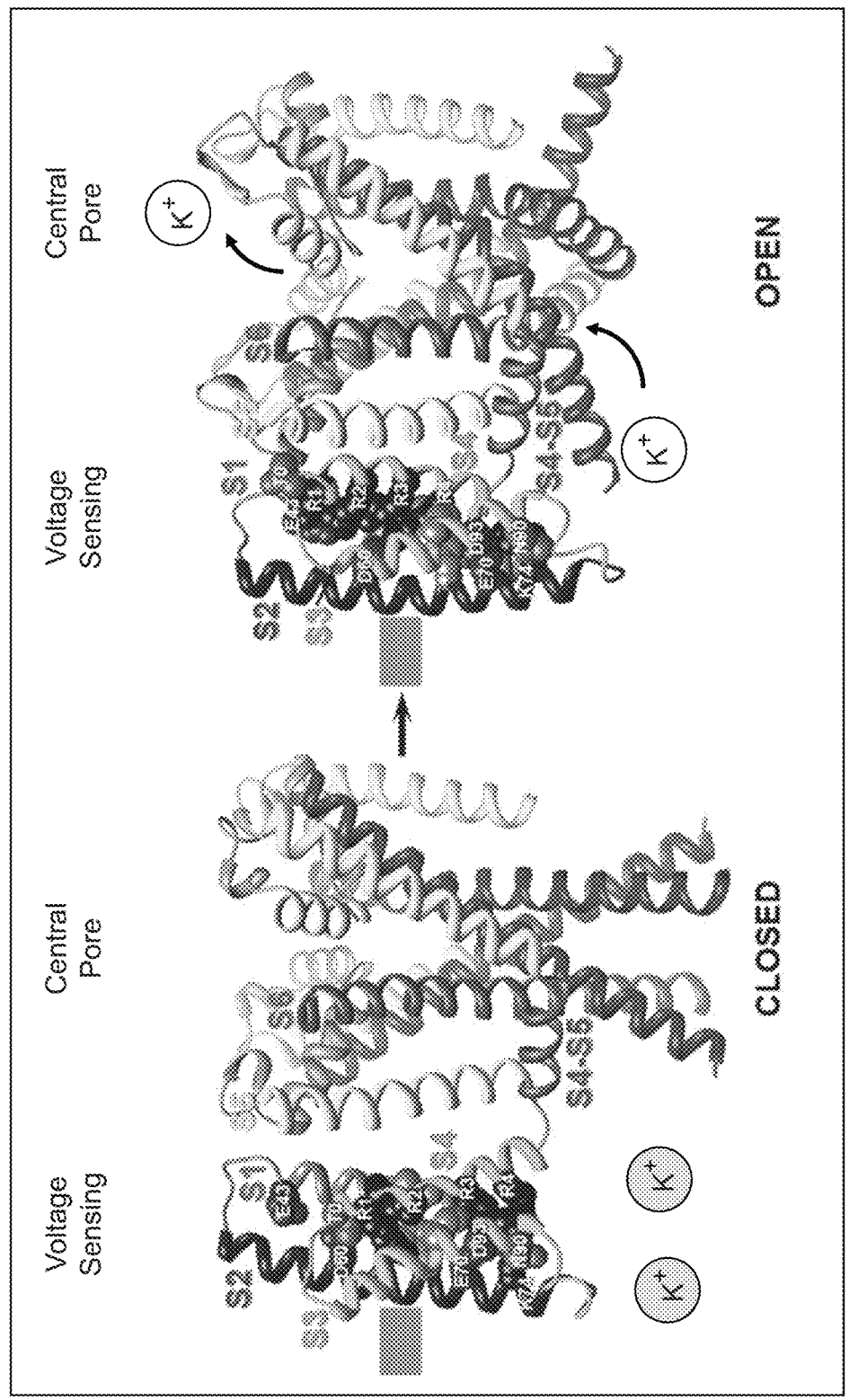
FIG. 9A illustrates conformational change of a transmembrane voltage-gated ion-channel.
Figure 9B:
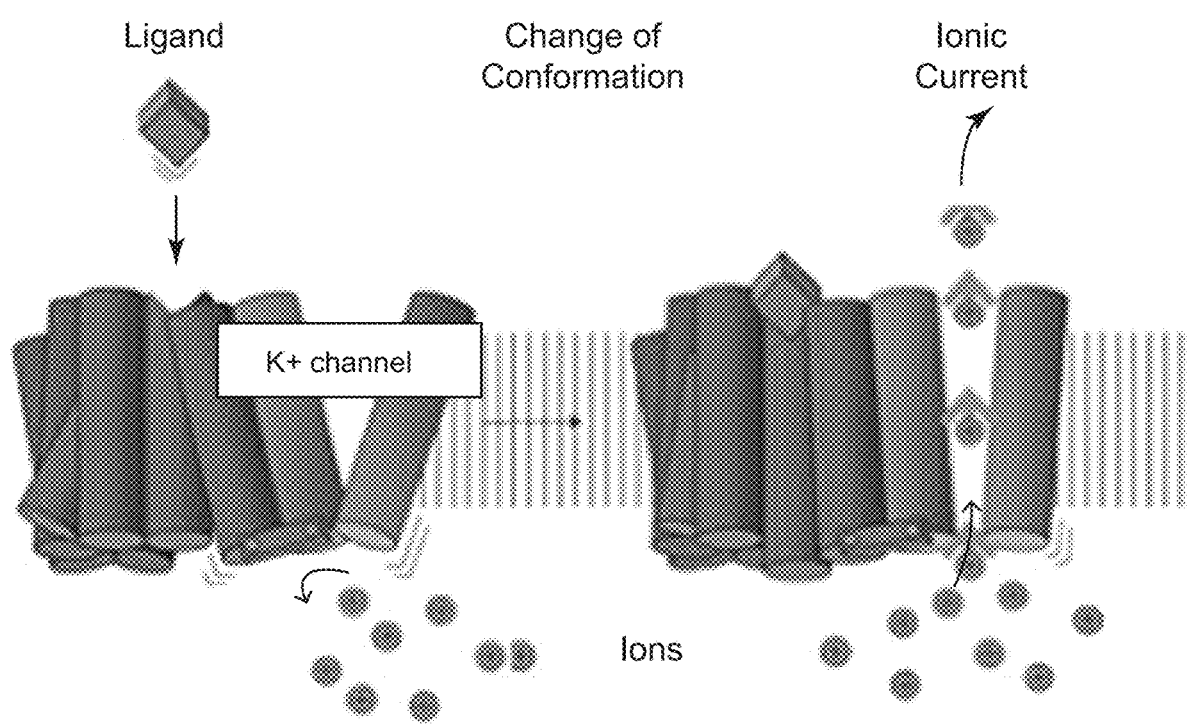
FIG. 9B illustrates conformational change of a transmembrane ligand-gated ion-channel.
Figure 10:
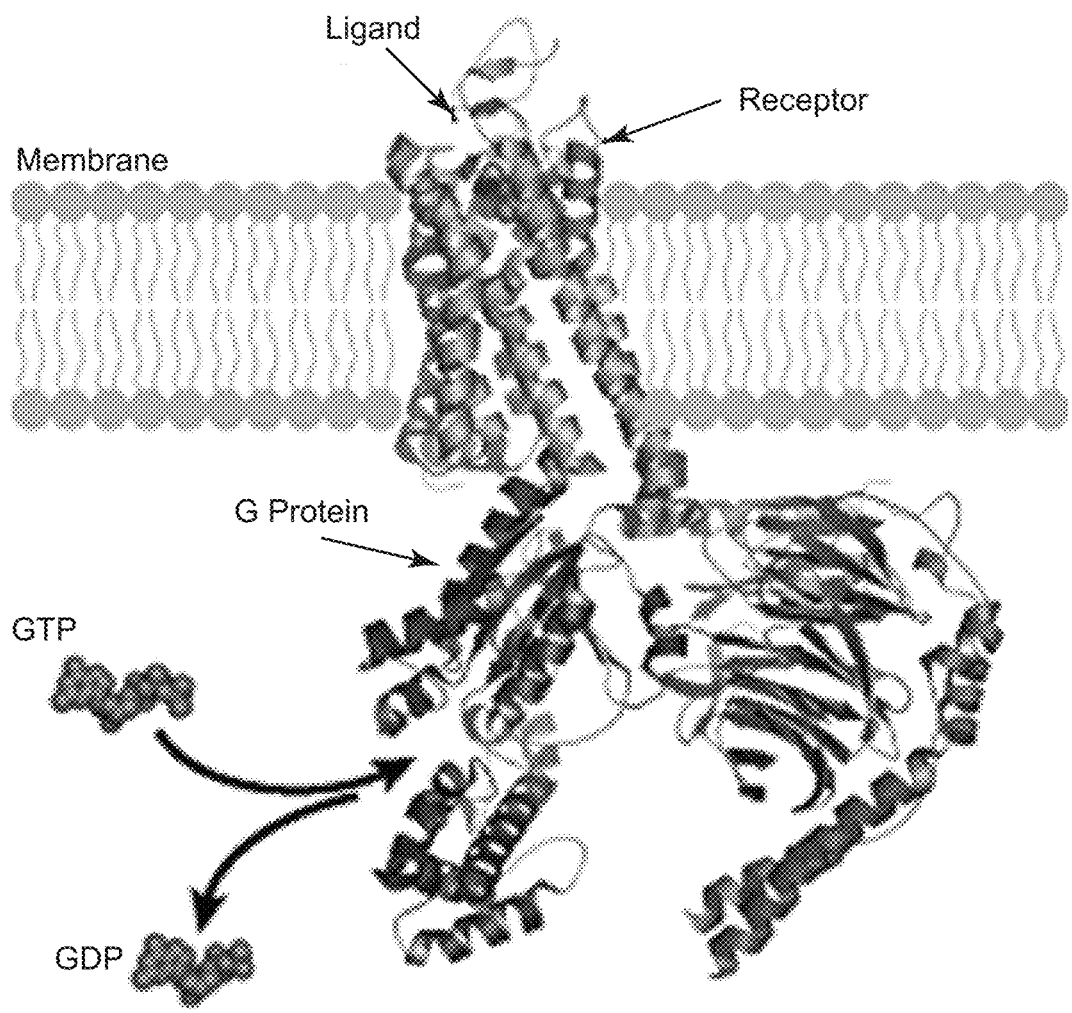
FIG. 10 illustrates G protein-coupled receptors.
Figure 11:
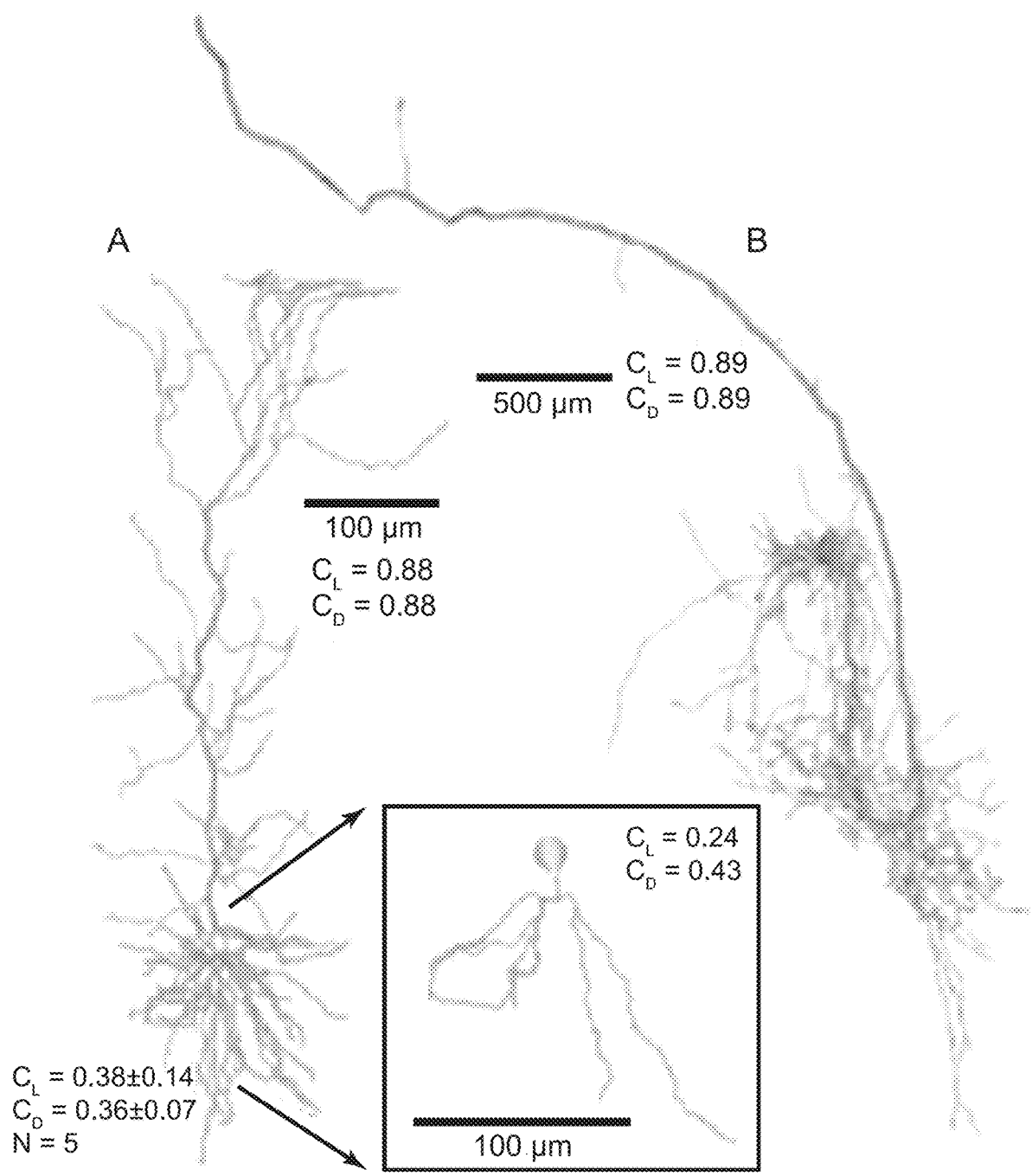
FIG. 11 illustrates exemplary morphometry of neurons, in particular showing a neuronal tree.
Figure 12:
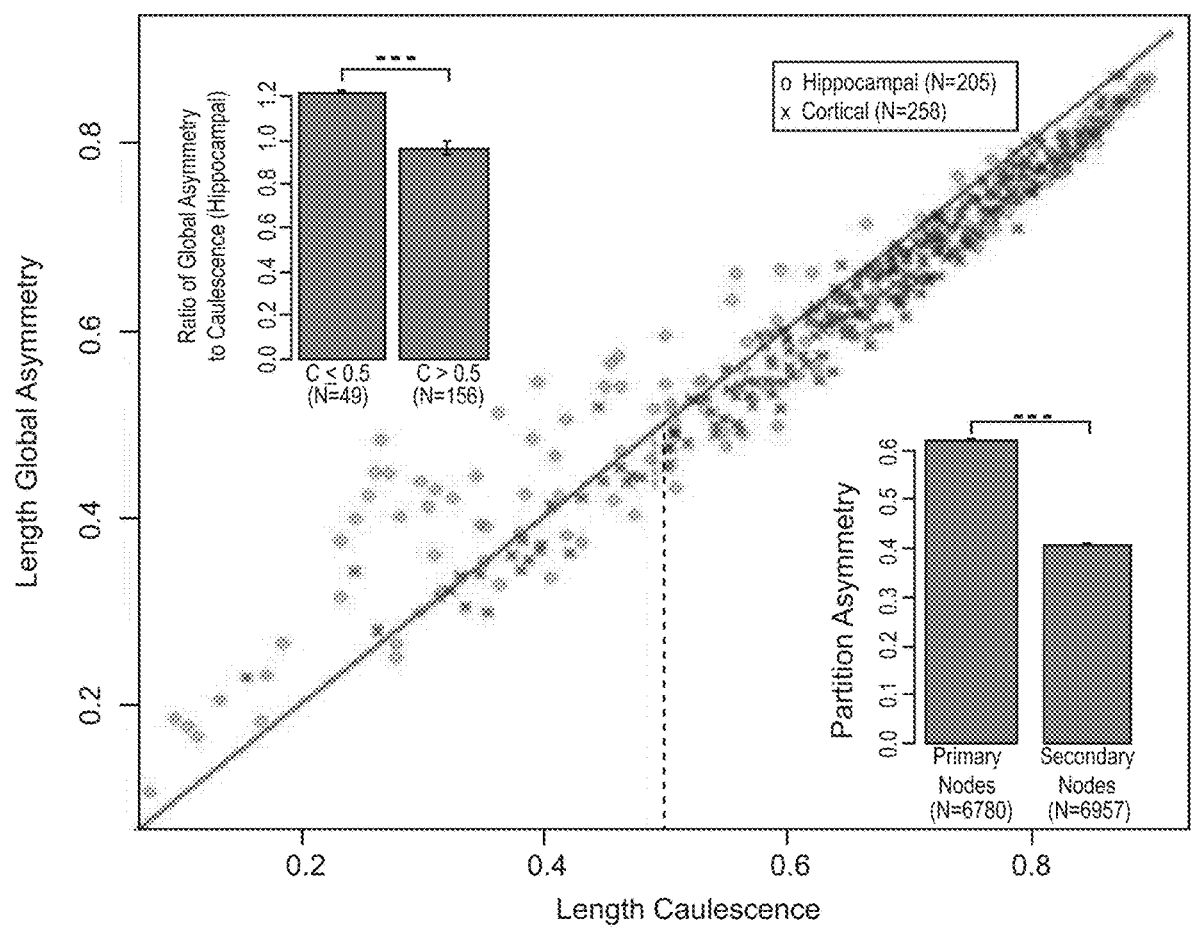
FIG. 12 is a scatter plot of rodent pyramidal cell apical dendrite global asymmetry versus caulescence.
Figure 13:
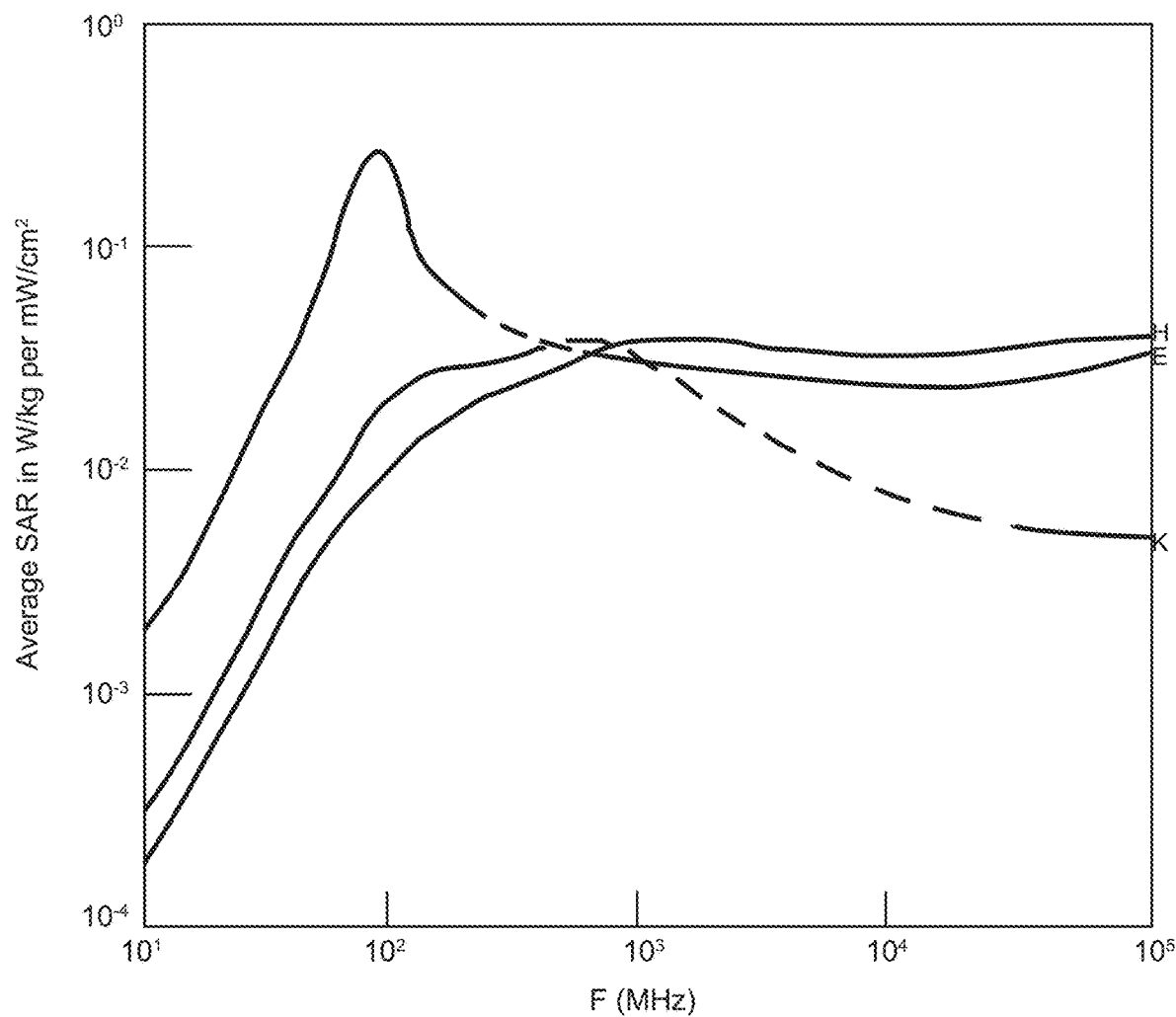
FIG. 13 is plot of Specific Absorption Rate (SAR) versus frequency.
Figure 14:
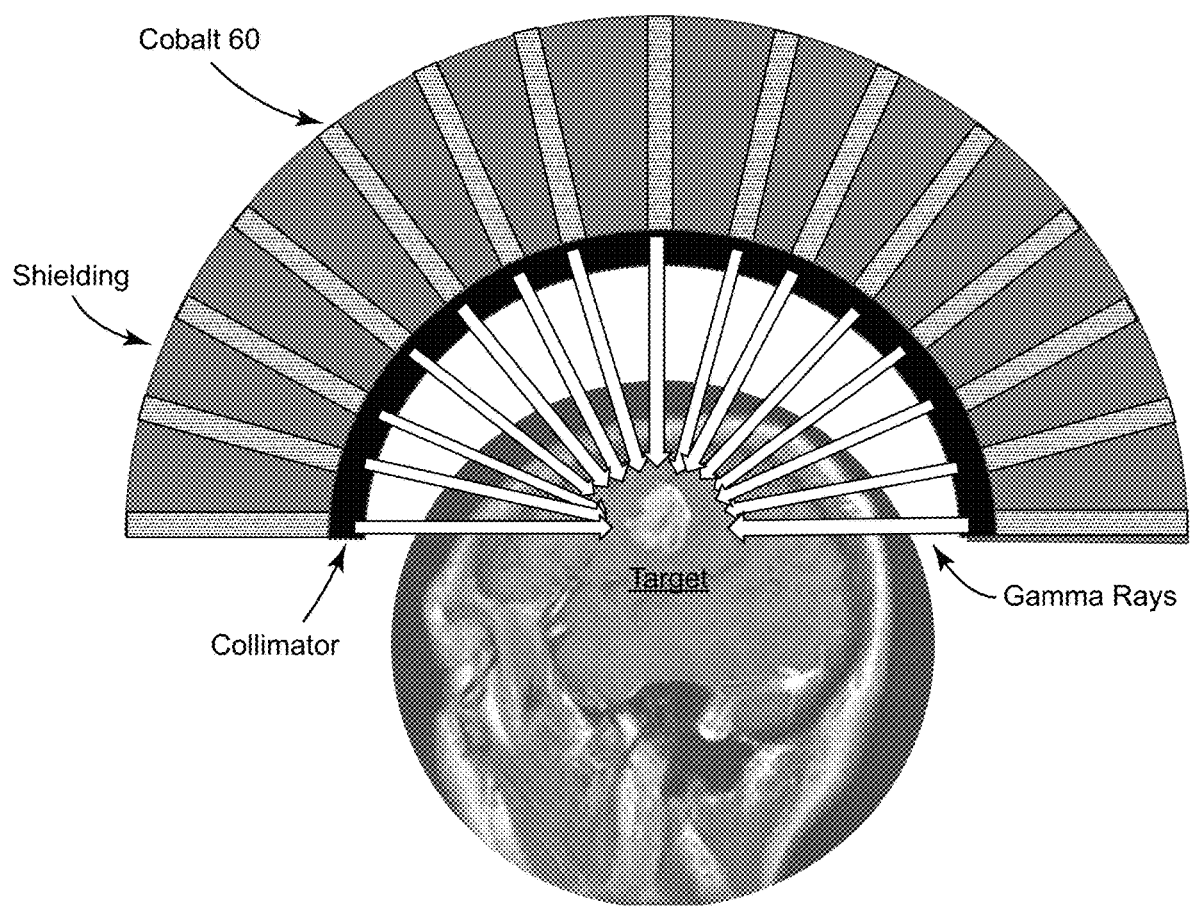
FIG. 14 is a schematic drawing of equipment used in the prior art for Cobalt 60 radiotherapy.
Figure 15:
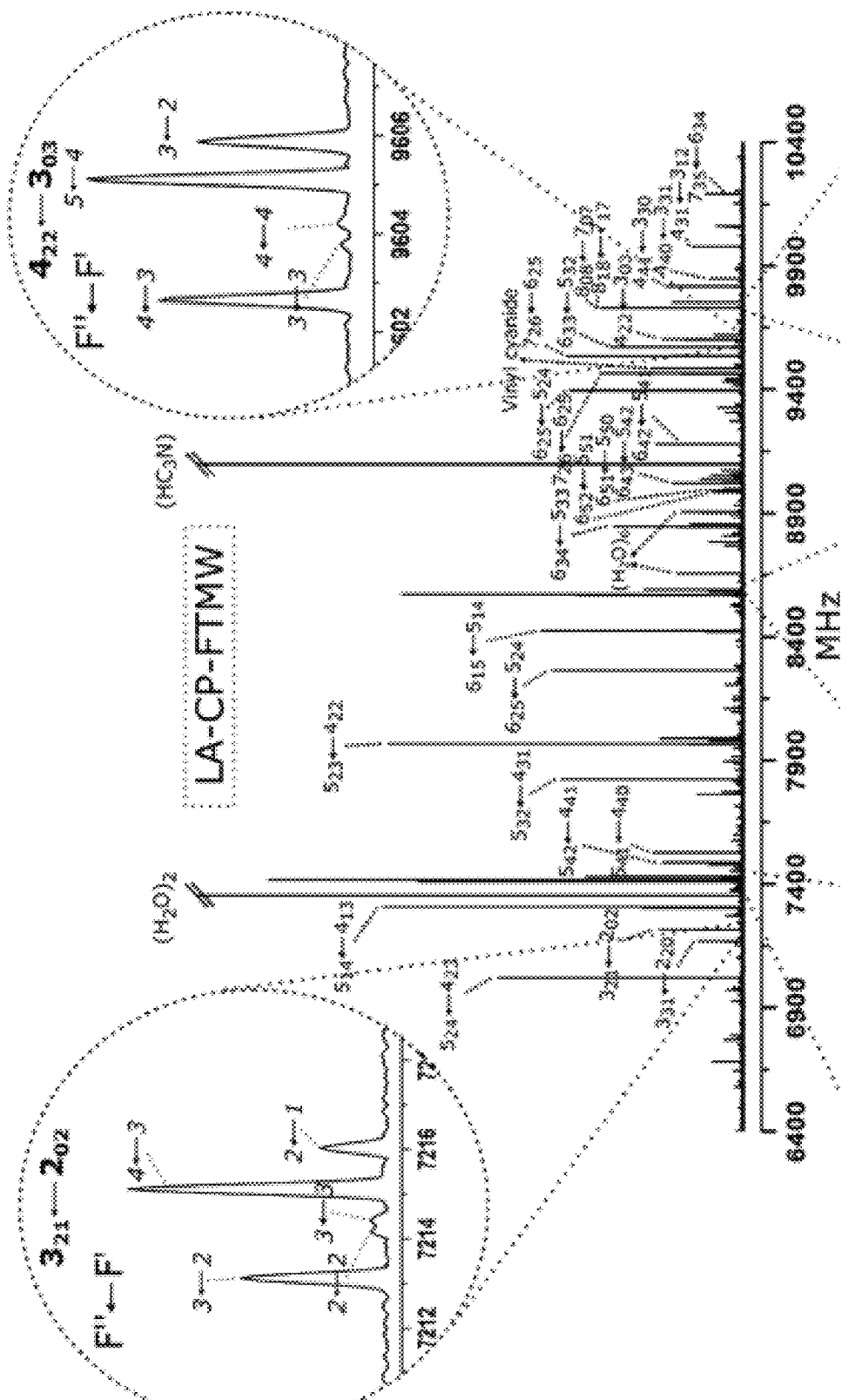
FIG. 15 shows a broadband rotational spectrum of saccharine from 6.4 to 10.4 GHz.
Figure 16:
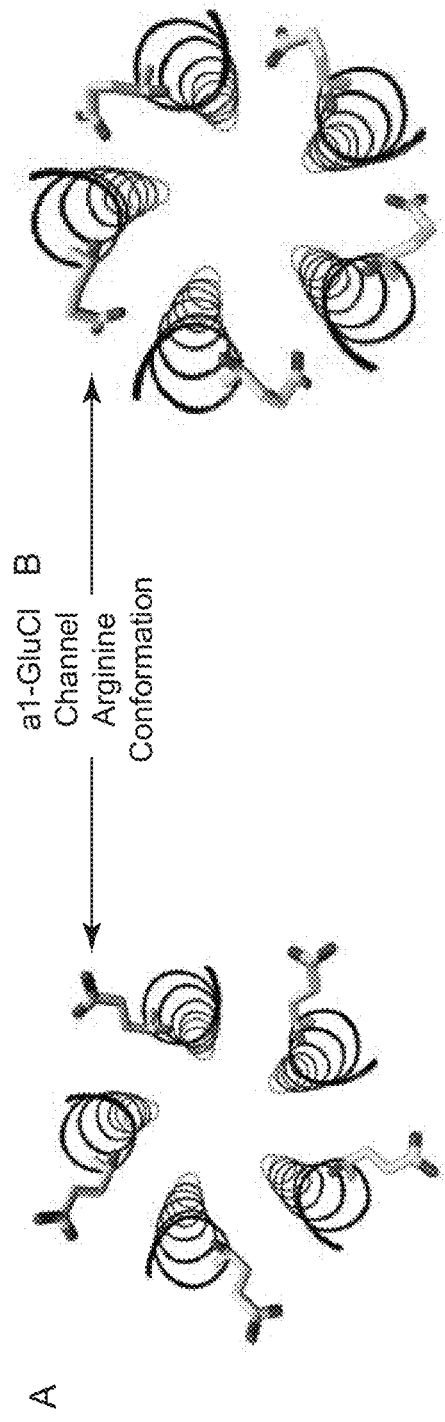
FIG. 16 shows data of the physical differences that occur with a conformational change in the α1-GluCL channel.
Figure 16:
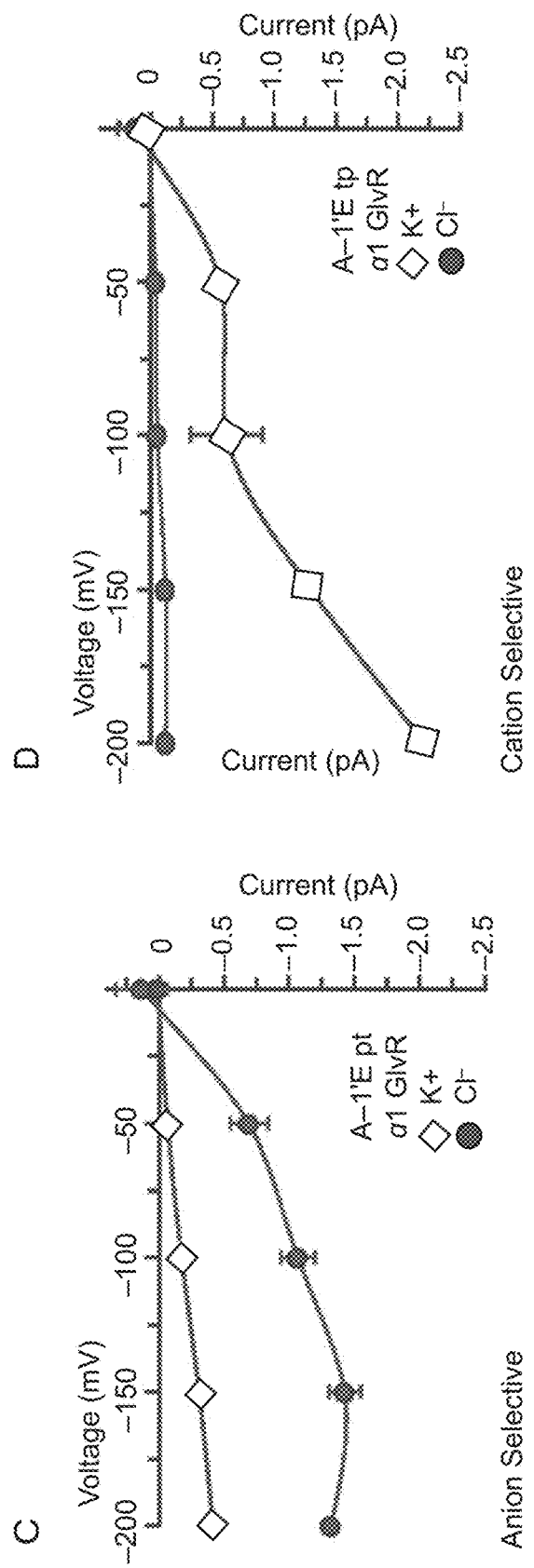
Figure 17:
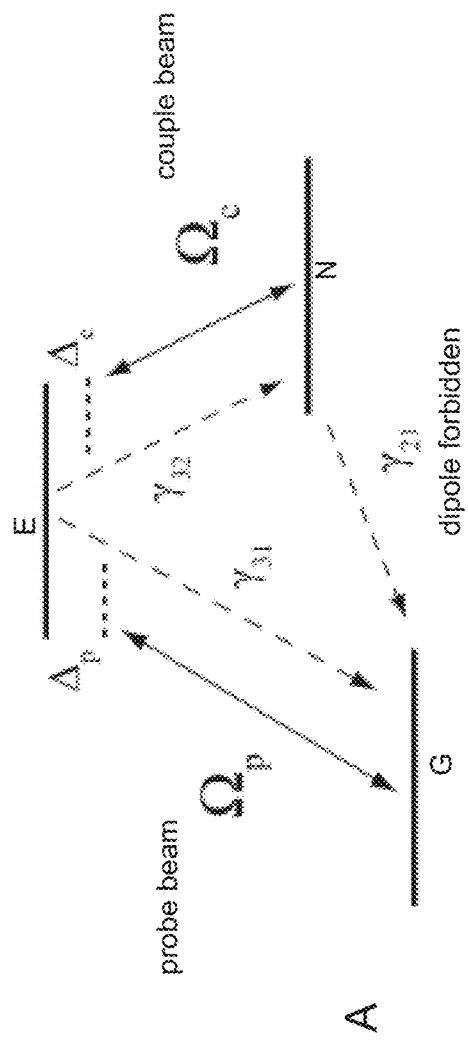
FIG. 17 illustrates a three-state system for electromagnetic induced transparency (EIT).
Figure 17:
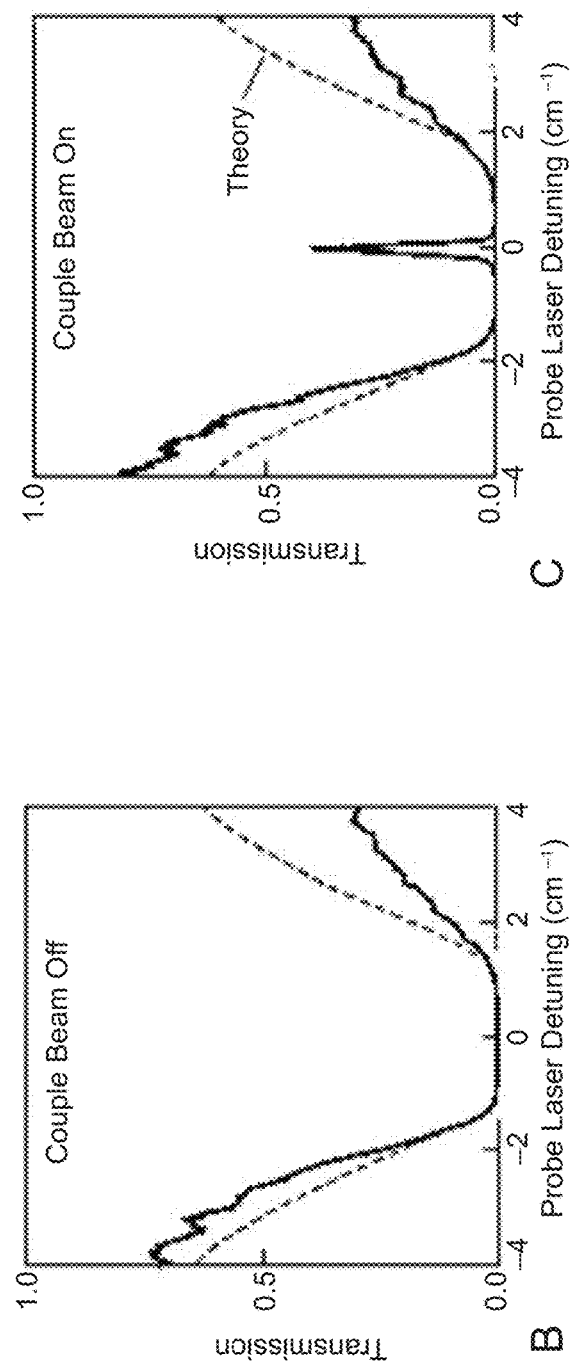
Figure 18:
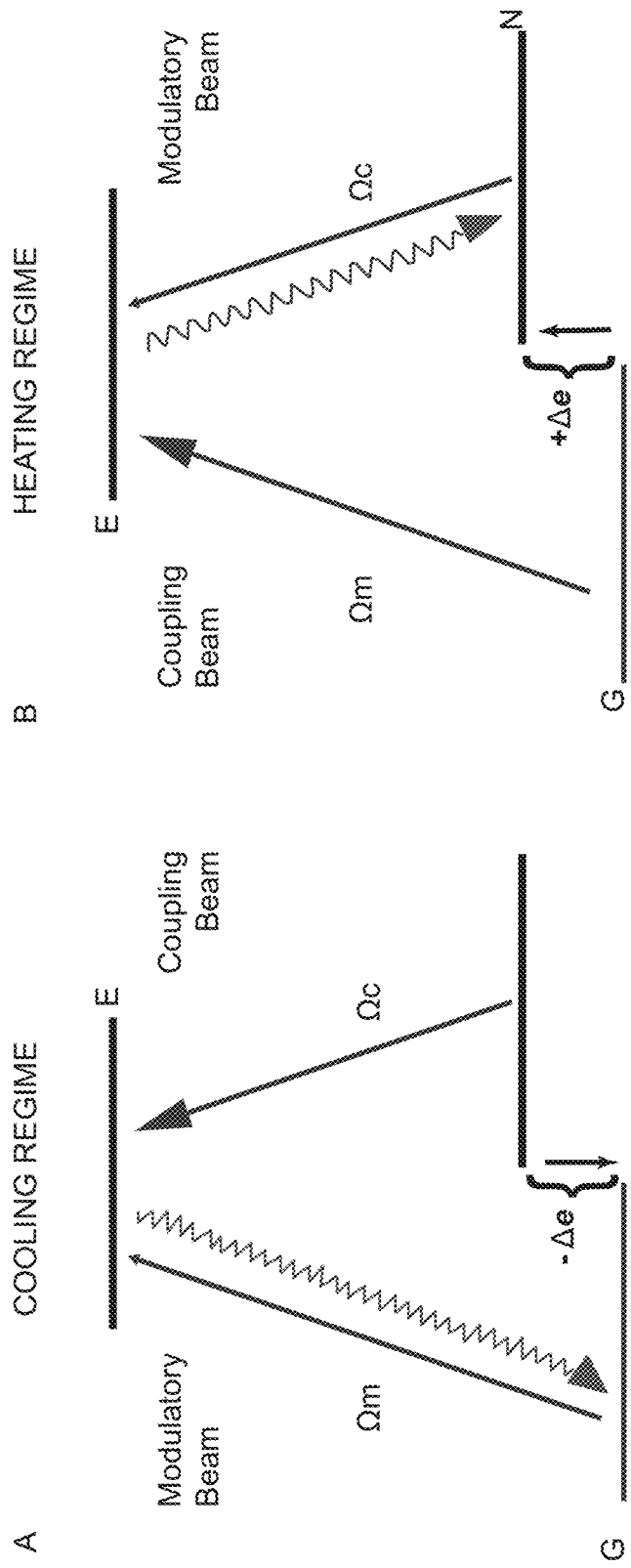
FIG. 18A schematically illustrates electromagnetically induced cooling.
FIG. 18B schematically illustrates electromagnetically induced heating.

The invention, as discussed above, pertains to systems utilizing low-power, coherent mode-locked, anisotropic microwave emission, or MASER radiation, to non-invasively record brain activity, to enervate (de-energize) specific brain targets, to energize specific brain targets, or to ablate specific brain targets. In the exemplary embodiment illustrated in FIG. 20, the invention provides the capacity to record activity at the whole brain level, as with functional magnetic resonance imaging (fMRI), and the capacity to record activity at the level of single neurons, as with penetrating electrodes. In the exemplary embodiment illustrated in FIG. 21, the invention provides the capability to enervate, energize, or ablate specific brain targets for therapeutic use.

While conceptually similar to lasers, a maser produces electromagnetic radiation in the microwave frequency range with longer and less energetic wavelengths than visible light. Unlike lasers, masers can penetrate optically opaque tissues. MASER emission does not have the harmful effects of ionizing radiation such as x-rays. By using interferometry, the comparison of a reference beam with a probe beam, a MASER system configured and operated in accordance with the invention can create activity maps of the human brain with an ultra-high degree of spatial resolution. At the theoretical limit, this approach can detect changes in activity with spatial and temporal resolution of 0.3 microns and 10 nano-second, respectively. The same physical system (with the use of a photonic modulation plate) also has the capability to either energize or enervate (de-energize) molecules, within a circumscribed brain target through resonant coupling of MASER emissions with active molecules. This feature has the potential to provide substantial therapeutic benefit. The critical elements for building a functional MASER system capable of activity mapping and neuromodulation are fabricated using thin film and epitaxial manufacturing processes.

Dynamic MASER interferometry for activity mapping as described herein has substantial medical implications. In one aspect, the invention uses coherent microwave emissions to record and convey dynamic changes in brain activity. Coherent microwave emissions are well-matched to the proposed brain mapping activity for several reasons. First, photons in the microwave range can be transmitted, absorbed, or emitted by biological molecules. Second, microwaves interact with biological molecules through the quantum transitions associated with vibration and rotation, meaning that the brain is semi-translucent from the microwave perspective. Third, in communications, antennas are devices having a dipole, or balanced charge. They are used as an interface between electromagnetic radiation and the current within the conductor. Neuronal processes such as axons or dendrites act as antennas, preferentially coupling MASER emission to molecules such as voltage gated ion channels and receptors embedded within the phospholipid bilayer. Fourth, most features of neuronal activity such as depolarization, generation of action potentials, neurotransmitter release, depolarization (along with various excitatory and inhibitory currents) are mediated through conformational changes of molecules embedded in phospholipid bilayer. Fifth, comparison of a probe beam with a reference beam allows for an exquisite degree of resolution since interferometry can detect minute changes in one beam relative to the other. Sixth, interferometry requires far less energy than using one beam to detect differences above the noise. Seventh, comparing two beams to another greatly reduces noise. Eighth, dynamic interferometry detects and records activity in real-time. Ninth, the technique is designed for detection of subtle changes in molecular properties, as opposed to structural mapping.

Figure 20:
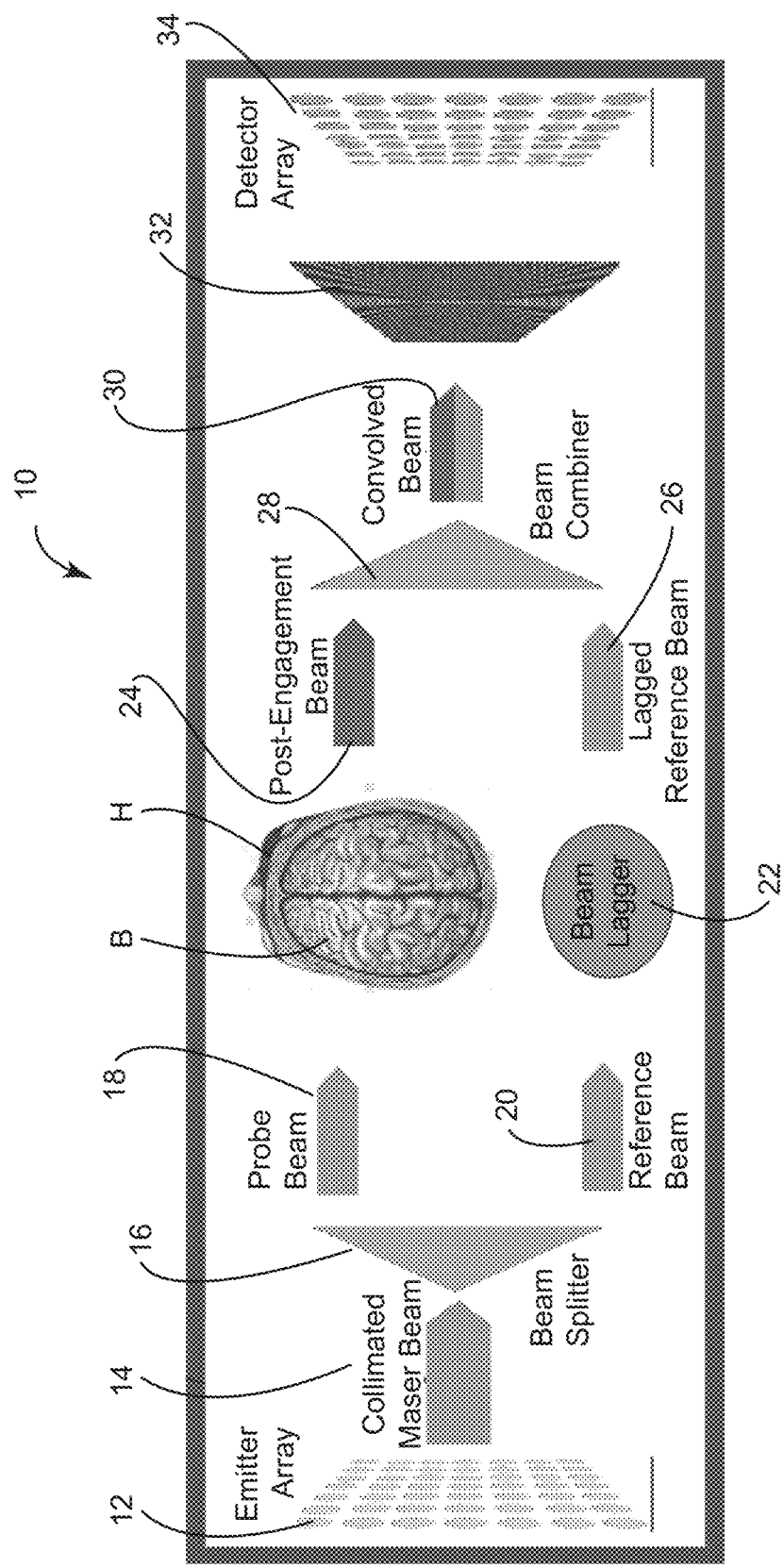
FIG. 20 is a diagram illustrating the components and operation of an exemplary embodiment of the invention.

Referring to the exemplary embodiment illustrated in FIG. 20, the activity mapping system 10 is a real-time MASER diffraction-limited interferometer. The activity mapping system shown in FIG. 20 includes an emitter array 12 that outputs a collimated MASER beam 14. The emitter array 12 is a phased-array of a plurality of emitters that outputs a mode-locked, coherent MASER beam which is then passed through a collimator (not shown). A beam splitter 16 is provided to split the collimated MASER beam into a probe beam 18 and a reference beam 20. Once masing begins, Q-switches in the emitter array 12 can be controlled to adjust phase and frequency of the beam, and can be controlled to include two or more characteristic frequencies, e.g. a coupling component and a modulation component of the beam. The probe beam 18 passes through the biological object which in FIG. 20 is a human head H. The activity mapping is intended to be for the brain B or a region of the brain within the head H. The passing of the probe beam 18 through the head H and brain B results in a post-engagement beam 24. Contemporaneously, the reference beam 20 passes through a beam lagger 22 which delays the reference beam 20 the same amount as the probe beam 18 is delayed passing through the head H. This results in a lagged reference beam 26. The post-engagement beam 24 and the lagged reference beam 26 are combined using a beam combiner 28. The combined beams result in a convolved beam 30 which exhibits a time-shifting interference pattern as depicted by reference number 32 in FIG. 20. A phased array of detectors 34 dynamically senses the interference pattern 32 using synthetic aperture interferometry techniques. De-convolution of the interference pattern quantifies changes in phase, modulation, amplitude and lag between the two beams 18 and 20.

The emitter array 12 in the exemplary embodiment is described in the above incorporated, co-pending patent application Ser. No. 17/148,215, entitled "Thin Film MASER Emitter and Thin Panel Phased Array of Emitters," James Joseph Cohen and Emad N. Eskandar, filed on even date herewith. As mentioned, the incorporated co-pending patent application describes a unique combination of thin epitaxial diamond film implanted with nitrogen ions in combination with other component layers to enable the fabrication of a thin panel, phased-array of MASER emitters, which uses Q-switching to form a mode-locked continuous wave MASER beam.

Briefly, starting at the back of the array the layered components are as follows: 1) A thermo-electric Peltier slab is oriented next to an LED layer to control the temperature of the LED layer. 2) A thin high-output Light Emitting Diode (LED) layer provides the photon pump. 3) A first layer of alternating layers of dielectric polymers to reflect the microwaves and provide the sides of the resonator cavity. 4) A layer of CCD (charge Coupled Device) controlled nematic molecules deposited unto the gain medium, which functions as a Q-switch and provides an interface for addressable control of the emission and entrainment of coherent emissions across the array. 5) The gain medium is composed of a thin-film of epitaxial diamond ion-implanted with nitrogen. 6) A second layer of the alternating layers of dielectric polymers to reflect microwaves and provide the other side of the resonator cavity.

The microwave wavelengths are orders of magnitude greater than the dimensions of a single emitter. The alternative approach of housing the entire flat panel array in a physical resonant cavity, would severely limit its practical application, and being a rigid physical structure, would also limit the potential for tunability.

As shown in FIG. 20, the MASER emitter array 12 takes the form of a panel, which is operated to generate MASER emissions that are stable and have long length coherence. The exemplary embodiment of the invention described above yields a MASER emitter formed by a multi-element phased array having a plurality of 2-dimensional emitters as a homo-structure, layered into a multi layered 3-dimensional assembly with orthogonal spacing offset by the desired resolution of the interferogram. This assembly is manufactured using an epitaxial technology or similar means to generate an implantable zero dangling-bond gain medium, that can be ion milled and implanted to achieve transitional vacancies at the desired masing frequencies. Further, this stacked emitter forms an addressable synthetic-aperture emitter, transparent to the optical pump except for the quantum lattice transition idealized by the ion implantation admixture.

In a typical MASER or laser, the gain media is contiguous, and all of the active moieties are essentially in one unit (such as a doped crystal), potentially participate in the process of amplification. Coherent emission is achieved by stimulated emission through a population inversion. In essence, the gain media, composed of a great plurality of coupled re-radiative components are stimulated with a pump of energy. Thereafter, a preferred step of energy conversion is selected by stimulating the transition in a uniform manner. This causes a cascade of emission from the gain media in an energy signature and vector consistent with the overall resonation of the gain media. Other radiative transitions are minimized and occupy a fractional component of the energy conversion. The overall effect is that the light emission appears to be radiating from a single radiative element. The photon wavefront is coherent and is synthesized from the overall emission topology.

In the exemplary embodiment of the invention, a different approach is used to generate coherent emissions from the array 12 of discrete emitters. As described above, Q-switching is a technique for disrupting transmission in a resonant cavity to allow for storage and emission of energetic pulses. In the exemplary embodiment of the invention, however, the goal is not to generate pulses but rather to drive continuous wave in-phase emissions form the individual emitters. In the exemplary embodiment of the invention, the Q-switch layer is mated to the active diamond layer, both of which are within the resonant cavity of each emitter. The Q-switch layer is transparent to photons (in the visible range) pumped from the LED layer, but selectively scatters photons in the microwave range of interest. Depending on its state (low Q or high Q), the switching layers selectively interferes with microwave transmission, favoring coherent emission across the entire array, and dispersing the rest. It is this effect by which a quasi 2-dimensional emitter/gain media can produce a diffraction limited beam of consequence.

Provided that the wave propagating emitter is stable and controllable, the Q-switch layer is used to generate a coherent beam through the combined emissions of the individual emitters. Before use, the array 12 of microwave emitters is calibrated. Once the array 12 is powered and stable, the Q-switch layer of each element is individually flipped from low-Q (nonpermissive) to high-Q (permissive) to determine the time needed to reach the masing threshold. This is a stable quantity reflecting particular features of each emitter element. Coherent emissions always start at the lowest point of the waveform. Once the timing is ascertained, the Q-Switch layer of each element is programed with a small delay specific to that element. The slowest element has zero delay while faster elements have proportionately longer delay. Subsequently, coherent emission is initiated by first turning all the switches to low-Q (nonpermissive). At the desired time, the individual emitters are flipped to high-Q (no disruption) with the programmed delays so that the faster elements begin emission at the same time as the slowest element. In this fashion, coherent emission from all the arrays starts at the same time. Since MASER emission always starts at the lowest point of the waveform, they are in-phase and the resultant beam, or wave-front, is coherent.

Prior to splitting the MASER beam, the beam is introduced into a collimator, such as a gaussian telescope composed of geometric optics. This telescope is fabricated to ensure that the overall divergence and coherence of the collimated MASER beam 14 is adequate to transverse the free space between the emitter array 12 and the deconvolution detector array 34 without decohering.

Figure 19:
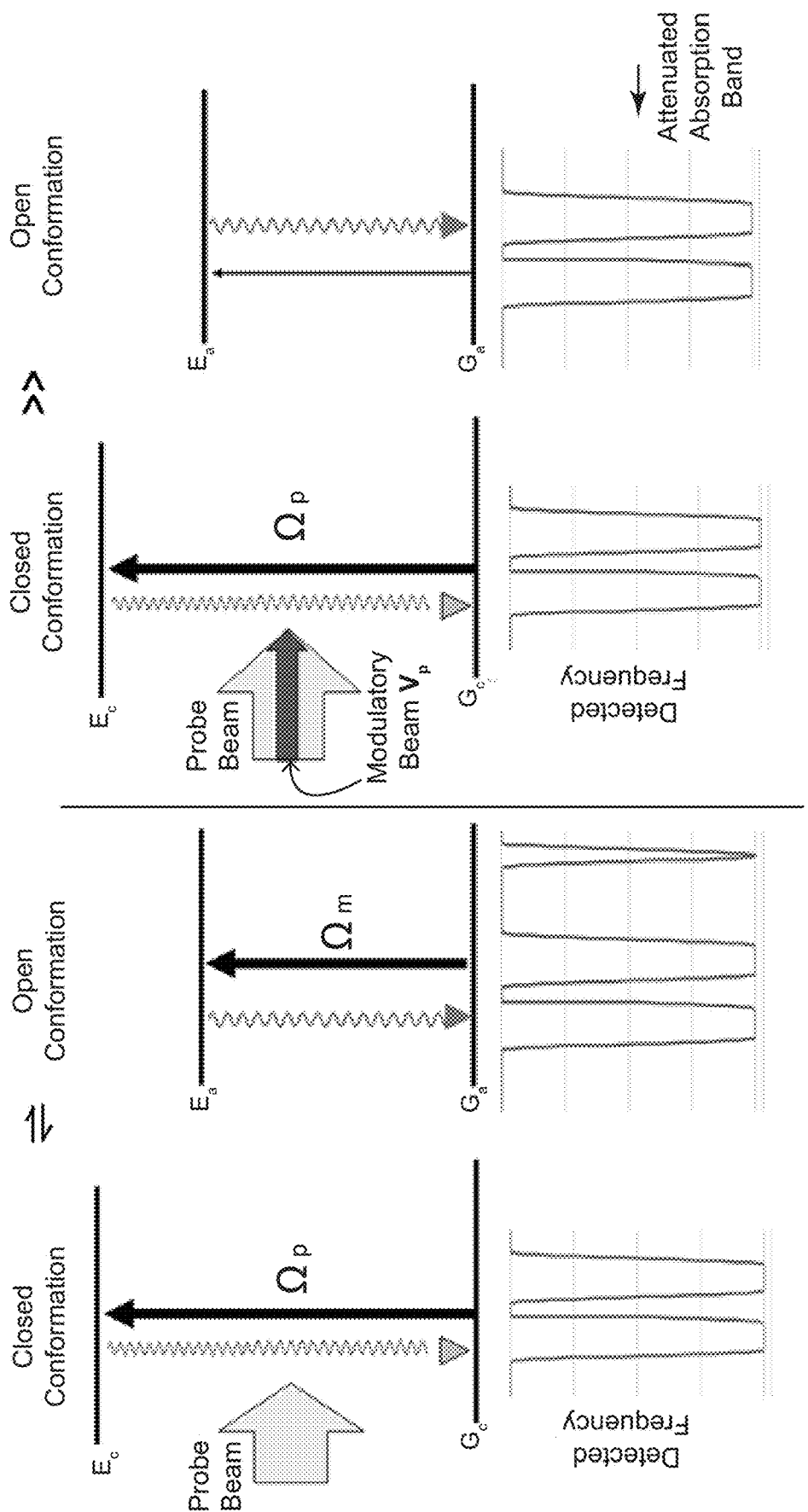
FIG. 19 describes how MASER radiation can be used to modulate conformational change and ion channel activity in accordance with various aspects of the invention.

The system 10 in FIG. 20 includes a geometric optic 16 (i.e. beam splitter 16 in FIG. 19) that serves to split the collimated MASER beam 14 into two coherent, mode-locked beams. Referring to FIG. 19, these beams 18, 20 are identified as the probe beam 18 and the reference beam 20. Being derived from a singular beam split into two components, these beams 18, 20 would normally remain singularly coherent over a free space distance corresponding the theoretical coherence length. Splitting the collimated MASER beam 14 into two beams 18, 20 having the same wavelength and phase/polarization coherence requires a grating 16 or geometric optic 16 made out of an optical grade polymer. The beam splitter 16 can be fabricated from dielectric materials and organized into geometries suitable for scraping. Poly-tetrafluoroethylene bulk material should be suitable. Successful beam splitting can be determined by analyzing the frequency, intensity, and coherence length of the probe beam 18 and the reference beam 20 and ensuring that its characteristics are adequate.

Still referring to FIG. 20, the reference beam 22 must be delayed in order to remain in phase with the modulated probe beam 24. A suitable beam lagger 22 is a pane of uniform material resulting in a delay similar to the delay caused by the head H and brain B. The performance envelope of the emitter array 12 and the detector array 34 requires a fully analog means to combine the modulated probe beam 24 and lagged reference beam 26. The beam combiner 28 should be engineered to preserve the coherence of the beams 24, 26 and not introduce aberrations that would interfere with data deconvolution. The beam combiner 28 is identical to the beam splitter 16 and interposed into the beam paths in the opposite manner of the beam splitter.

The detector array 34 is specifically designed for the detection of MASER energy in a dynamic acquisition sufficiently fast and sensitive to resolve interference patterns 32 in the convolved beam 30. Passage through various substances results in phase distortion of the probe beam 18 relative to the reference beam 20. Combination of the post-engagement beam 24 and the lagged reference beam 26 results in an alteration of the interference pattern 32 in the convolved beam 30. Each element of the detector array 34 has two layers offset by an orthogonal offset. A suitable detector array 34 is described in incorporated, co-pending application Ser. No. 17/148,275, entitled "Phased-Array MASER Detector for Synthetic Aperture Interferometric Imaging," by James Joseph Cohen and Emad N. Eskandar. The orthogonal offset provides a spatially disparate sensing discriminator. The offset sensors can otherwise be identical, such spatially offset sensors permit correspondence to a time difference measured in decades of picoseconds. This architecture permits real time sensing of data otherwise indistinguishable from the noise background.

The diode layers consist of zero Bias Schottky Detector diodes with sufficient sensitivity to reliably detect and reflect different values of MASER emission. These can be biased with Zener diodes to provide the necessary stability for precise edge-detection.

The repeatability and stability of the jitter permits real time data acquisition in the frequency of interest: Pseudo real-time deconvolution requires running parallel Fast Fourier Transforms (FFTs), maximally optimized for rapid execution. These are ASIC (Application Specific Integrated Circuit) components providing digital output. The number of discrete devices and channels coordinates to the jitter maximum of both the emitters and the detectors. Parallel CPUs and data storage subsystems are provided to ensure that time-sliced deconvolution is not recursive nor gapped thereby preventing decoding artifacts from being introduced.

In the system described in the above referenced application entitled "Phased-Array MASER Detector for Synthetic Aperture Interferometric Imaging," the combination or convolution of the beams is accomplished via an analog beam combiner. Time-sliced intensity data of the interference pattern in the convolved beam is detected by the plurality of detector elements in the phased array detector 34. The plurality of detector elements in the phased array detector are arranged in a first planar layer and in a second planar layer that is parallel to the first planar layer and offset in three dimensions from the detector's elements in the first planar layer. The time-sliced intensity data of the interference pattern detected by the plurality of detector elements is recorded in a database, and a computer is programmed to de-convolve the time-sliced intensity data of the interference pattern. As mentioned above, the first step of deconvolution is to apply a Fast Fourier Transform in order to isolate one or more wavefront frequencies for processing. The result of the deconvolution results in processed data that quantifies changes in one or more of phase, modulation, amplitude, and lag between the post-engagement beam and the lagged reference beam and the creation of a holographic perspective map. This projection is holographic in nature as it is a projected volume illumination from a distilled interferogram. A voxel map is populated with the processed data for the slice of time from the given holographic perspective and this is repeated from multiple holographic perspectives in accordance with a synthetic aperture algorithm to improve the resolution. The populated voxel map is then associated with or overlayed on an image generated by an MRI or CT scan to create a three-dimensional energy activity map for the given time slice of the biological object or a portion of the biological object. The three-dimensional energy activity map for the given time slice is then displayed for immediate review or stored for later analysis. The method can be repeated for subsequent time slices to generate time-shifting, three-dimensional energy activity maps.

Figure 21:
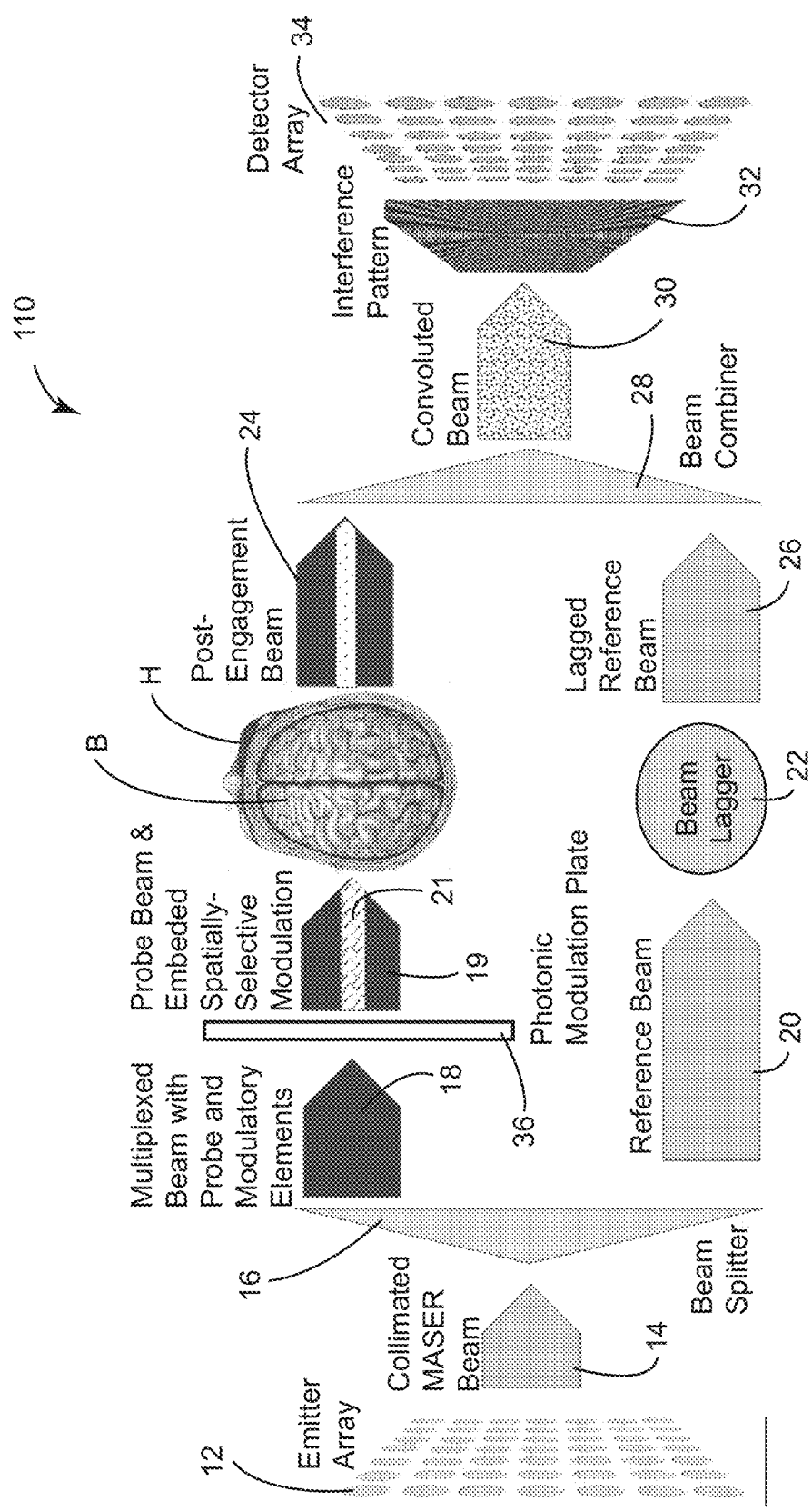
FIG. 21 is a diagram illustrating the components and operation of another exemplary embodiment of the invention.

The system 10 in FIG. 20 provides for acquiring data as to the function and performance of in-vivo mapping of brain activity as potentiated at the axonal interfaces. Moreover, modulation of the MASER emitter array 12 by temporal carrier generation permits selective enervation and energization of specific voxel points with the encephalon. The invention generates data rich 3-D energy maps of the brain B. These maps show significant differences in energy maps corresponding to discrete epochs in the behavioral task such as resting, visual-cue, go-cue, movement, feedback, and reward. Referring to FIG. 21, a photonic modulation plate 36 can be added to the system 110.

In addition to generating energy activity maps, MASER radiation can penetrate optically opaque tissues and can affect state conditions of vibratory molecules via resonant coupling. In this context, the goal is to de-energize molecules just enough to temporarily stop or perturb neuronal activity. The brain represents a complex mixture of atoms, molecules, membranes, and cells. However, some of the same considerations related to activity mapping apply. Neuronal processes such as axons or dendrites are antennas, preferentially coupling MASER emissions to molecules such as voltage-gated ion channels and receptors embedded within the phospholipid bilayer. Most features of neuronal activity, such as depolarization, generation of action potentials, and neurotransmitter release, are mediated through conformational changes of molecules embedded in phospholipid bilayer. The activity mapping identifies changes the spatial location of the changes. Molecules susceptible to energy coupling is apparent as spectral absorptions, or as stimulated emissions, occurring during the period of activity. Hence, the map can provide information regarding both the spatial location and the presence of molecular targets for enervation. With that information, it is possible to create a convolved beam 30 that contains a modulated interference map 32 of the structure. This beam 30 can be digitally modulated to result in a dissipative function for selecting an energy pathway away from the regular system. Dissipative energy is absorbed by the surrounding tissue. The goal is to correlate particular molecules with specific resonance frequencies, locations, and activity patterns.

Neuromodulation occurs when spatial modulation (e.g., via a photonic plate 36) of the probe beam 18 is superimposed upon the active brain structure B. This is a non-invasive means to either enervate or energize active potentiated neuronal voxels. MASER energy is delivered to the Nucleus accumbens (NAcc) and Caudate (CD) during presentation of evocative visual cues with the ability to abandon induced habits in favor of new behaviors reinforce.

FIG. 21 illustrates phase-shifted Rabi coupling to targeted signature receptors for enervation or ablation. Referring to FIG. 21, the system 110 includes a photonic modulation plate 36 through which the probe beam 18 passes prior to the passing through the patient's head H and brain B. The photonic modulation plate 36 may be square, made of quartz and controlled by piezoelectric means. In an alternative configuration, the active elements in the photonic modulation plate are nematic liquid crystals that in the presence of an electric 2 field produce a in the polarization of traversing light waves. When the system 110 is used for imaging as in FIG. 20, the photonic modulation plate 36 can be set to be completely transparent to the probe beam 18. However, the photonic modulation plate 36, or a region in the plate referred to as an "aperture" can be controlled to shift the phase of the probe beam 18, at the given frequency, in order to Rabi couple with targeted signature receptors in selected regions of the brain. FIG. 21 illustrates the probe beam 19 after it passes through the photonic modulation plate 36 as including an embedded spatially modulated portion 21. The coupling transfers energy to the targeted receptor, for neuromodulation such as enervation and/or ablation. It is contemplated that the system in FIG. 21 switch intermittently and in near real time between Rabi coupling to targeted signature receptors and activity mapping via diffraction-limited interferometry as described in FIG. 20. However, intermittent activity mapping may not be required in all applications.

As mentioned, the system 110 in FIG. 21 uses phase shift enhancement for Rabi coupling to target signature receptors.

The tuning of the modulatory beam component is now discussed in more detail. A modulatory element of the probe beam is adjusted in a temporally varying manner to modulate the abnormal patterns of activity observed with the probe beam mapping function in disorders such as addiction and other neuropsychiatric disorders.

Different frequency components are multiplexed into the beam using the technique of phase modulation. Typical phase modulation consists of a carrier frequency and a slower modulation frequency. The phase of the modulation frequency retards or advances the phase of the carrier frequency. The resulting multiplexed waveform is described in the time domain by the formula below where the value of y is at time (t), $A_c$ is amplitude of the carrier wave, $\omega_c$ is the circular frequency of the carrier wave, m is the phase of the modulatory wave, and $\varphi_c$ is the instantaneous phase deviation of the carrier frequency:

$$y(t) = A_c \sin(\omega_c t + m(t) + \varphi_c)$$

Figure 22:
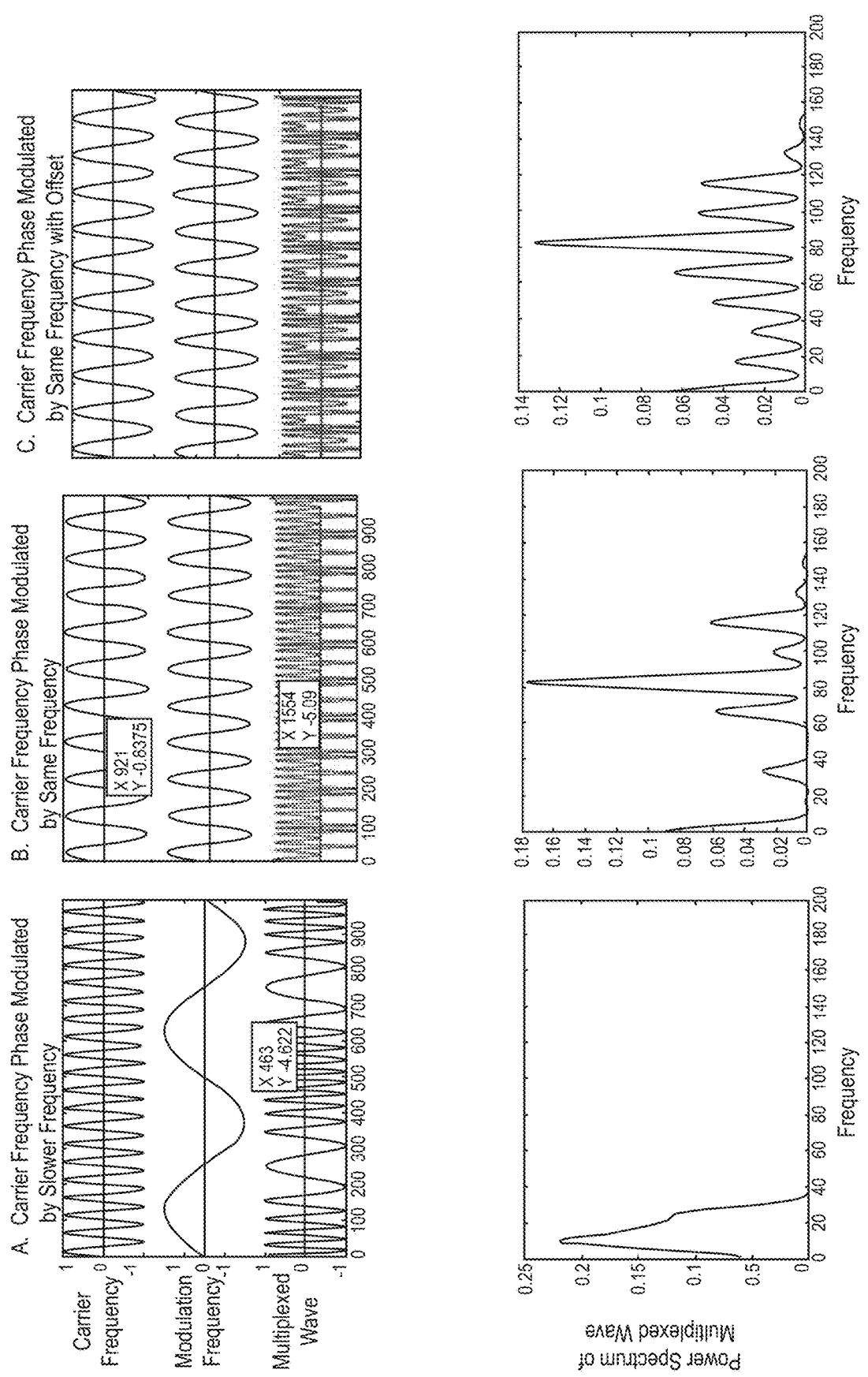
FIG. 22 includes charts illustrates the modulation of a carrier frequency, as the concept is applied in the present invention.
Figure 23:
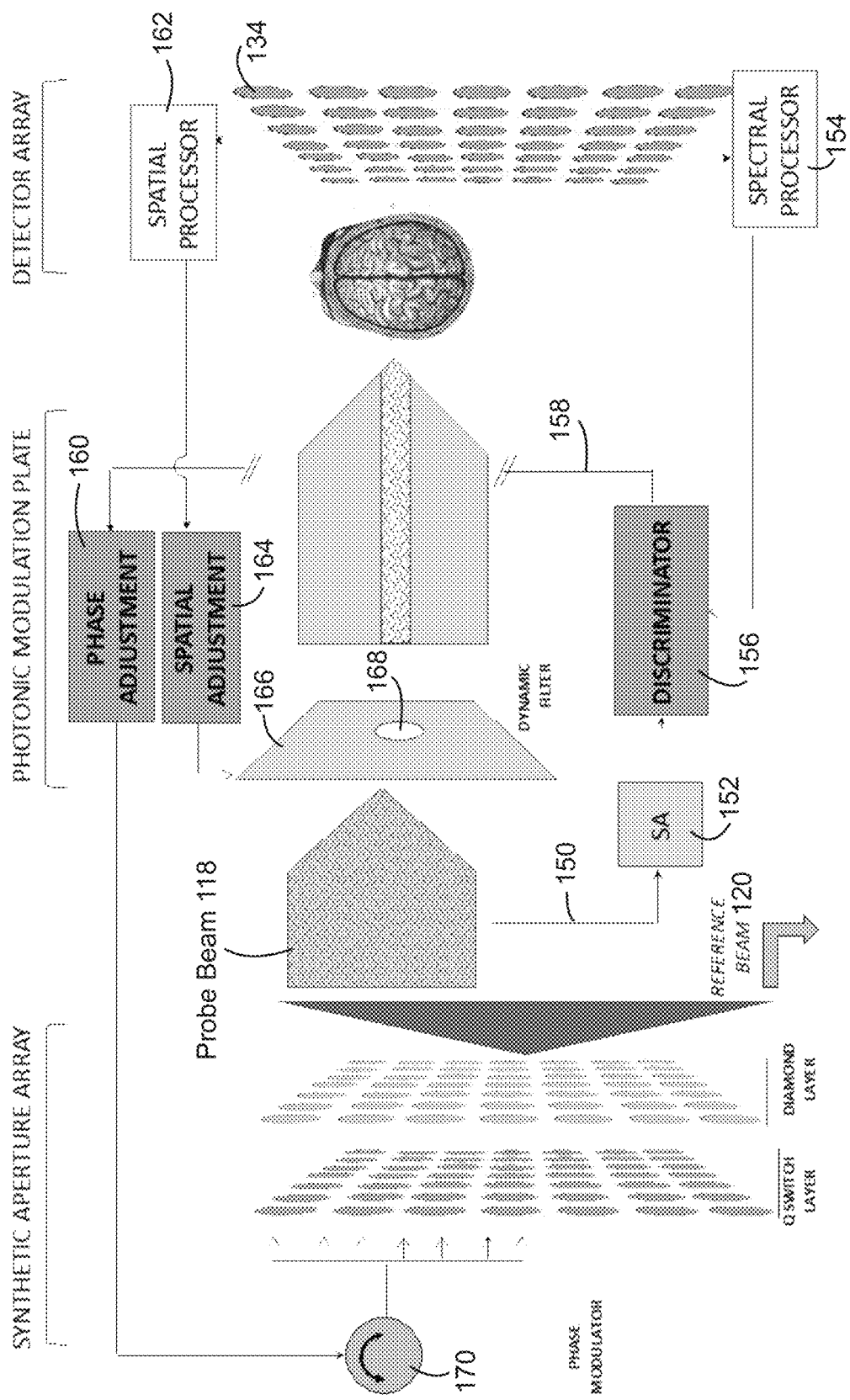
FIG. 23 is a schematic drawing illustrating closed-loop, phase and spatial adjustment of the probe beam in accordance with an embodiment of the invention.

FIG. 22 A (upper panel) demonstrates a carrier frequency of 20 Hz, a modulatory frequency of 2 Hz, and the resultant multiplexed waveform. FIG. 22 A, (lower panel) demonstrates that the power spectrum of the multiplexed wave that is broad, representing the range of frequencies around the carrier wave engendered by the phase modulation. FIG. 22 B (upper panel) demonstrates the effect on the multiplexed wave of using a modulatory wave with the same frequency and phase as the carrier wave. The multiplexed wave reflects a more complex pattern, and exhibits power in frequency bands, other than the carrier wave, in the power spectrum. FIG. 23 C (upper panel) demonstrates the effect of a modulatory wave also having a fixed offset (in this case ⅙ pi, or 30 degrees. In addition to exhibiting power at the carrier frequency of 20 Hz, there are additional bands at higher frequencies, the most prominent occurring at 80 Hz.

The relevant factor in multiplexed output is the instantaneous frequency. The use of phase modulation enables the system to deliver a broad range of instantaneous frequencies beyond the frequency of the parent beam so as to preferentially bias molecular conformations away from those associated with pathological or undesirable patterns of brain activity.

FIG. 23 schematically illustrates the arrangement of various elements and functions for implementing a neuromodulatory element in the MASER probe beam. During activity mapping, and the initial stage of neuro-modulation, the probe beam 118 is not modulated. A portion of the probe beam 150 is routed to spectrum analyzer (SA) 152. The target spectral signature extracted from by spectral processor 154 analyzing data from the detector array 134 is compared to the output of the spectral analyzer 152 by a discriminator 156, which outputs the difference 158 between the frequency components of the probe beam and the desired frequency elements. This information 158 is then used to generate a phase adjustment 160, which is then incorporated into the probe beam using a phase modulator 170. The phase modulator 170 adjusts the Q-switch layer to advance or retard the phase of the probe beam, thereby creating a feedback loop. This system self-adjusts to reach the distribution of frequencies that best eliminate or attenuate the spectral patterns associated with pathological brain activity.

An additional function is spatial adjustment. Pathological activity is found in certain brain areas at certain periods of time (100-200 ms) in the brain. As with phase modulation, the spatial pattern of activity is extracted from the detector array 134 (i.e., spatial processor 162) and used to create a spatial adjustment 164. The patterns of spatial adjustment drives nematic liquid crystals in the photonic modulation plate 166, so that there is an aperture that permits some or all frequencies to pass through an aperture 168 targeting the area of interest. The rest of the plate is adjusted so as to become a filter 166, allowing only the primary—unmodulated—frequency of the probe beam to pass through. This system also uses a feedback approach (not shown for clarity) to incrementally adjust the aperture 168.

Both the phase and spatial adjustments use a gradient-descent method aimed at minimizing the root mean squared (RMS) error. Given the rapidity of adjustments compared to the relatively slow rate of change in brain activity, the system will converge fairly quickly, within a few seconds, to an optimal solution. The use of internal feedback greatly reduces the computational burden as exact solutions do not need to be calculated, but rather empirical solutions are generated through an iterative approach.

Therapeutic neuromodulation is an important application of the invention. The invention can be used to treat certain neurological, psychiatric or behavioral disorders characterized by abnormal patterns of stimulus-evoked neuronal activation in the prefrontal cortex and striatum observed in addiction, pathologically prominent oscillations in the Beta band (15-25 Hz) in Parkinson Disease, and paroxysmal discharges in the Theta frequency band (4-8 Hz) in epilepsy.

Figure 24:
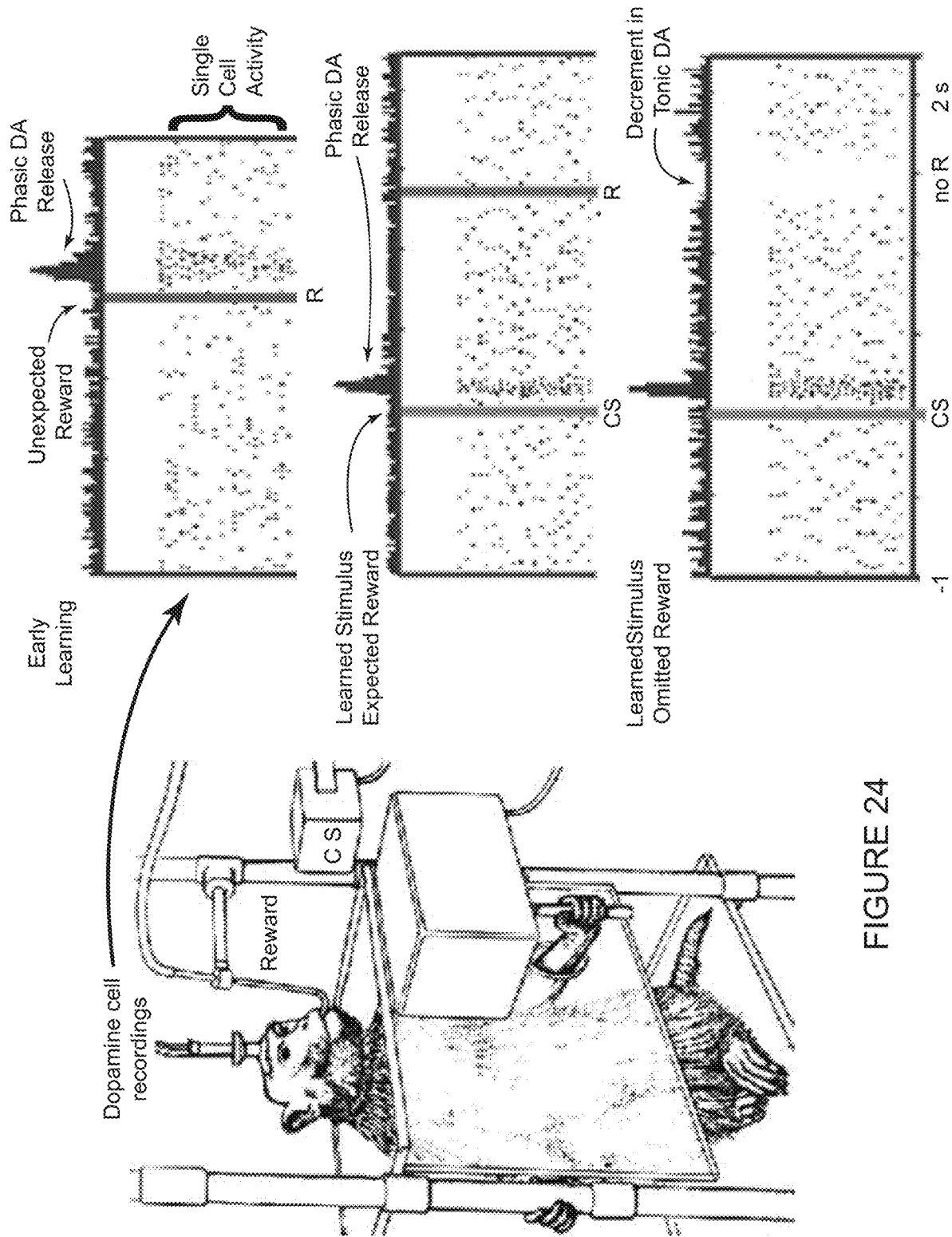
FIG. 24 is an illustration of known data pertaining to the release of dopamine (DA).

The envisaged use is for the treatment of psychiatric disorders including Addiction, Major Depression, Post Traumatic Stress Disorder (PTSD), and obsessive compulsive Disorder (OCD), along with neurological disorders such as Epilepsy, Parkinson Disease and Alzheimer Disease. An example is the treatment of addiction which is based on the similarity of neural circuits involved in learning and those implicated in addiction. Specifically, the Nucleus Accumbens (NAcc), the anterior caudate nucleus (CD), the dorsal putamen (PT), and reciprocally connected cortical areas such as the Orbital-Frontal cortex and the Dorsolateral Prefrontal Cortex (DLPFC). Another feature in the connection between learning and addiction is the central role of dopaminergic signaling in both processes. Referring to FIG. 24, phasic or pulsatile dopamine (DA) signals a reward prediction error (RPE), which is an important feedback signal in formal learning models, most notably temporal difference reinforcement learning (TDRL) (Schultz et al., 1993). DA neurons in the VTA have well-characterized properties: they fire maximally to unexpected reward, moderately to expected reward, and depress activity below their tonic baseline rates in response to omitted rewards (Schultz, 1998; Schultz et al., 1992). Effectively, dopaminergic neurons signal the discrepancy, or error, between expected and actual rewards. Critically, once an animal or human learns that a particular stimulus reliably predicts reward, Phasic DA release shifts and occurs at the time the predictive stimulus is perceived and not at the time the reward is delivered (FIG. 24). If the learned stimulus is presented, but is not followed by reward, there is a drop in tonic DA levels and over a period of time, the association is extinguished. The extinction of associations that cease to be rewarding is of equal importance to new learning, else the organism continue to accrue useless and potentially harmful associations. These useless associations compete with new learning and hamper or prevent adaptation.

Phasic DA results in long-lasting potentiation of active cortical-striatal synapses, providing a potential mechanism for the physical instantiation of learning in cortico-striatal circuits (Herndndez-López et al., 1997). Disrupted dopaminergic signaling has been implicated in addiction to stimulants, but more recently studies using cyclic voltammetry demonstrated that opiates and ethanol also evoke phasic DA release, suggesting that hyperactive phasic DA release, as opposed to tonic changes, is a feature common to many addictive substances (Covey et al., 2014)

Figure 25:
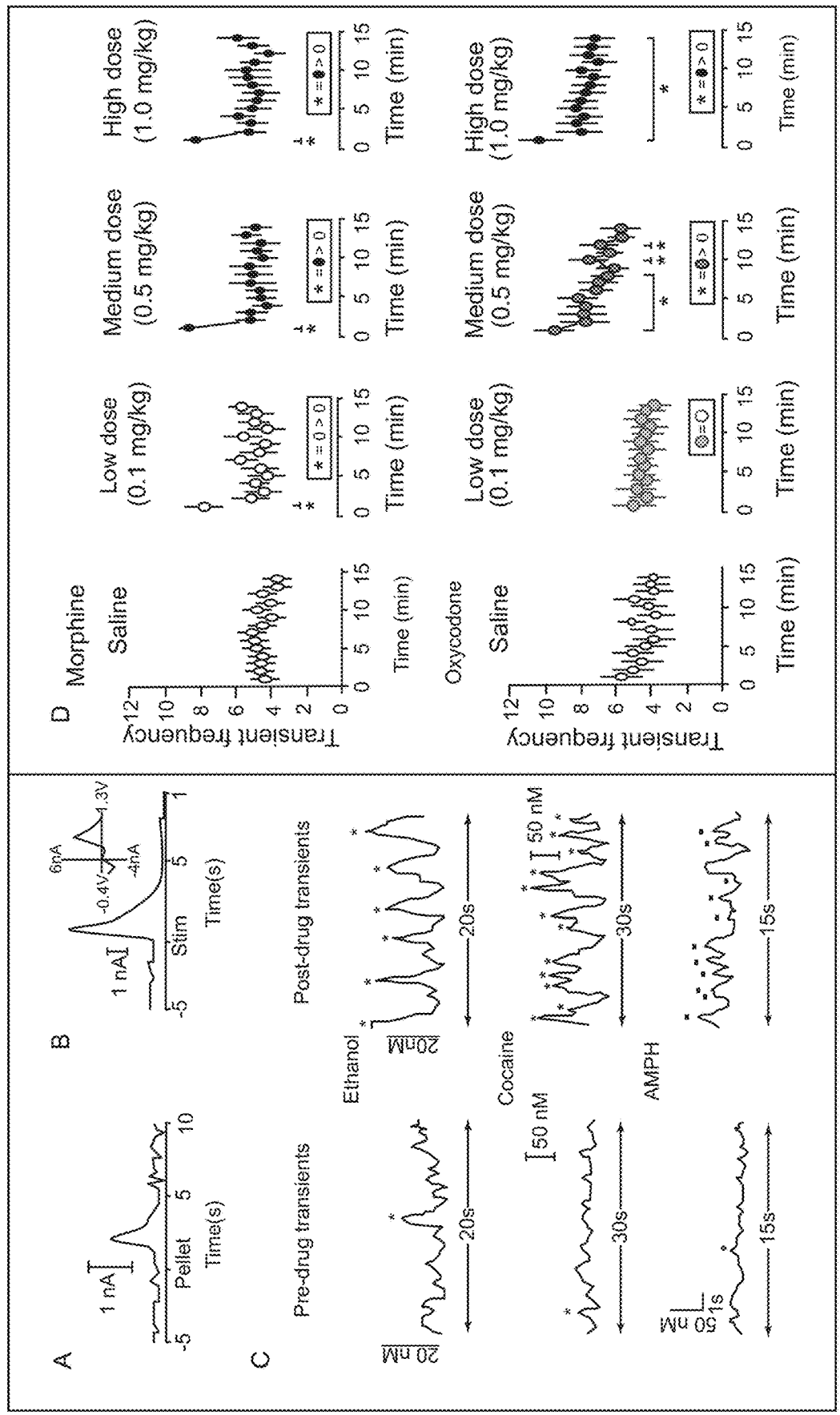
FIG. 25 illustrates data from a prior art study that in contrast to the isolated DA pulses evoked by natural rewards, the more direct effects of addictive substances can result in multiple high-amplitude pulses manifest as bursts of DA release.

Phasic DA signaling is necessary and sufficient for forming cue-reward associations and for cue-directed reward-seeking. The effect of biologically important, rewarding stimuli on DA neurons is indirect, being mediated by afferents from sensory and homeostatic systems. In contrast, many addictive substances—through inhibition of DA reuptake (stimulants), mu-receptor mediated inhibition of GABAergic interneurons (opiates), or modulation of ionic conductance (ethanol)—directly affect DA signaling. As shown in FIG. 25, recent studies have demonstrated that in contrast to the isolated DA pulses evoked by natural rewards, the more direct effects of addictive substances can result in multiple high-amplitude pulses manifest as bursts of DA release (Covey et al., 2014).

In summary, phasic DA release is an internal, tightly regulated control signal. Addictive substances can hijack this signal and directly potentiate active cortical-striatal synapses, enhancing stimulus-response patterns associated with their consumption relative to those associated with natural rewards. This effect is potentially compounded by an early and abnormal transition of the same stimulus-response pairings toward the habitual system, which is also mediated by Phasic DA release. Together, the two effects cause a profound distortion of the learning circuitry, leading to the rapid development of highly potent associations and behavioral patterns that are extremely difficult to abandon even in the face of demonstrable harm.

Figure 26:
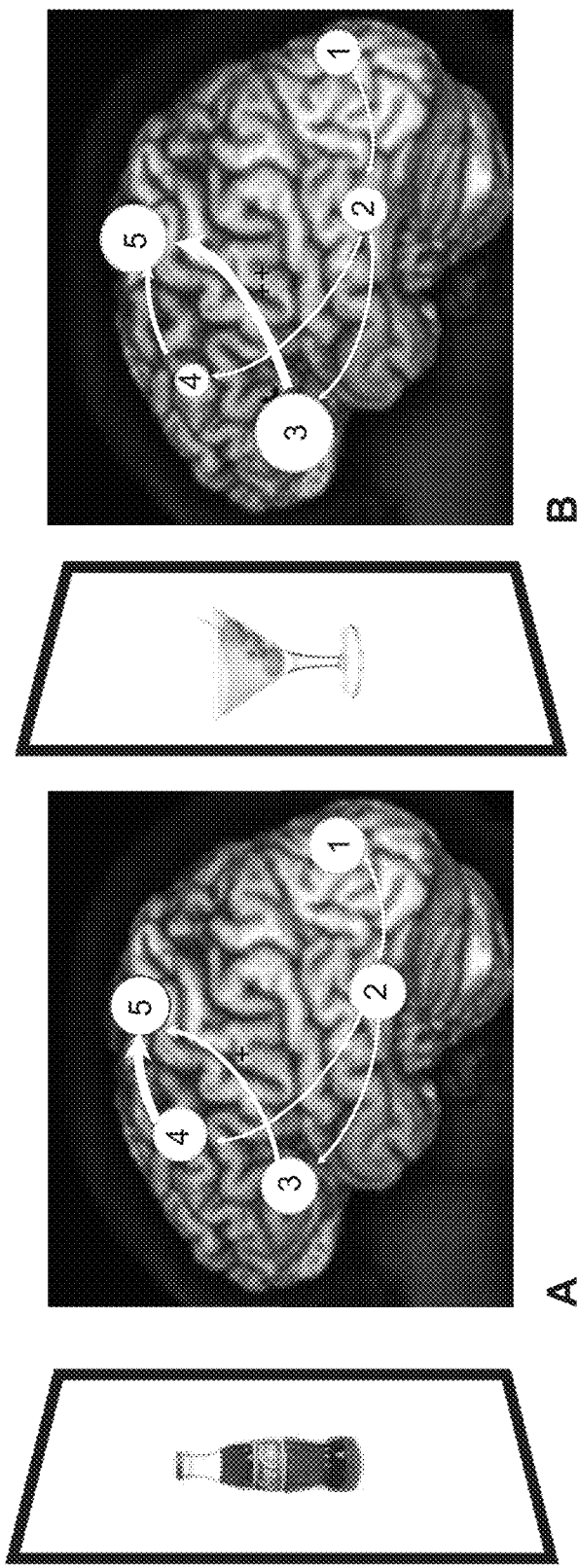
FIG. 26 illustrates aspects pertaining to the temporal sequence of brain activation in learning and addiction.

FIG. 26 illustrates aspects pertaining to the temporal sequence of brain activation in learning and addiction. Referring to FIG. 26A, presentation of a learned visual stimulus first activates the primary visual cortex (FIG. 26A, location 1) The object is quickly recognized by the temporal cortex (location 2) and then its value or salience is determined by the orbital-frontal cortex and Nucleus accumbens (location 3). The dorsal-lateral prefrontal cortex and caudate ascertain the potential risk of short and long-term harm of securing the object (location 4). The balance of these two circuits determines the decision. If the decision is to proceed, then the premotor and motor areas generate the appropriate plan and actual movement, respectively (location 5). Otherwise, no action is taken to secure the object.

In addiction (FIG. 26 B), the excess of dopaminergic reinforcement means that a stimulus associated with the substance of abuse results in exaggerated activation of the orbital-frontal cortex and greatly heightened salience (location 3), and a diminution of risk-avoidant function in the in dorsal-lateral prefrontal cortex (location 4). The balance overwhelmingly favors consuming the object, thereby triggering a habitual or compulsive behavioral pattern by the premotor and motor areas (location 5).

These patterns of activity are associated with increases in glucose metabolism, along with increased activity of G-protein coupled dopaminergic receptors, ligand-gated glutamate receptors, and voltage-gated ion channels. These changes occur in the different areas of the brain following the particular temporal and spatial sequence just described.

As an example, a patient with an addiction to alcohol would first undergo energy activity mapping with a system configured in accordance with the invention. The patient would then view a monitor and perform a behavioral task wherein images of various beverages are presented in separate trials (e.g., Coke, Orange Juice, Water, and Full Martini Glass). The subject performs a task to ensure they are engaging with the stimuli (e.g., indicating whether the current stimulus is the same as the previous stimulus). The activity maps generated by non-addictive beverages (Coke, Orange Juice, Water) are subtracted from the activity map generated by the Martini and the resultant map represents the pathological pattern of activity.

Unique or excessive temporal patterns of absorption associated with the addictive substance, but not the others, are then targeted for neuromodulation. Preferential suppression of these spectra means that Dopaminergic receptors, Glutamatergic receptors, voltage-gated ion channels, and other molecules associated with neuronal activity are energetically less favorable to undergoing the conformational changes associated with activation. If the pattern of activity is diminished, then the associations are no longer being reinforced with same intensity, leading to the eventual extinction of abnormal salience, overlearned associations, and habitual or compulsive behavior.

Other disorders are broadly analogous in exhibiting abnormal patterns of activity in different brain areas. Based on existing fMRI technology, where it is necessary to average data from multiple patients to identify a signal, there are weak associations between Major Depression and Area 25, PTSD and the amygdala, OCD and the dorsal Anterior Cingulate Cortex.

The mapping function is expected to map molecular, axonal, and neuronal activity at much greater levels of spatial and temporal resolution so that the unique patterns of abnormal associated with any given patient can be selectively identified and targeted for therapeutic modulation.

The various embodiments of the systems described above are contemplated for the following uses:

The use of MASER Dynamic Interferometry to study and characterize patterns of molecular activation in healthy subjects and in those suffering from psychiatric and neurological brain disorders.

The use of MASER Dynamic Interferometry to study and characterize activation of specific patterns of molecular activation in voltage-gated ion channels, ligand gated ion channels, and G receptor coupled channels.

The use of MASER Dynamic Interferometry to study patterns of neural activity associated with normal brain function in sensory, cognitive and emotional tasks.

The use of MASER Dynamic Interferometry to study, characterize, and diagnose abnormal protein deposition and patterns of neural activity associated with neurodegenerative disorders including ALS, MultipleSclerosis, MMN, Parkinson Disease and Alzheimer Disease.

The use of MASER Dynamic Interferometry to study, characterize, and diagnose patterns of neural activity Movement disorders such as tremor, dystonia, and tics.

The use of MASER Dynamic Interferometry to study, characterize, and diagnose disordered brain activity in epilepsy, migraine headaches, tinnitus and chronic pain.

The use of MASER Dynamic Interferometry to study, characterize, and diagnose patterns of neural activity in Psychiatric disorders including obsessive-compulsive disorder (OCD) major depression, bipolar depression, schizophrenia, generalized anxiety, post-traumatic stress disorder (PTSD), phobias, and panic attacks.

The use of MASER Dynamic Interferometry to study, characterize, and diagnose patterns of neural activity in behavioral disorders including substance addiction, pathological gambling, obesity, attention deficit hyperactivity disorder (ADHD), internet gaming disorder and autism.

The use of MASER enervation and MASER activation, either in isolation or in combination, to treat movement disorders including tremor, dystonia, and tics (Tourette's).

The use of MASER enervation and MASER activation, in isolation or in combination, to treat disorders of brain activity including epilepsy, migraine headache, tinnitus and chronic pain.

The use of MASER enervation and MASER activation, in isolation or in combination, to treat psychiatric disorders including obsessive-compulsive disorder (OCD) major depression, bipolar depression, schizophrenia, generalized anxiety, post-traumatic stress disorder (PTSD), phobias, and panic attacks.

The use of MASER enervation and MASER activation, in isolation or in combination, to enhance recovery of movement, speech, short-term memory, long-term memory and cognition following brain injury or stroke.

The use of MASER enervation and MASER activation, in isolation or in combination, to enhance memory in Alzheimer disease.

The use of MASER enervation and MASER activation, in isolation or in combination, to promote disaggregation and absorption of abnormal protein deposits including alpha-synuclein in Parkinson disease, amyloid in amyloidosis and beta-amyloid in Alzheimer disease.

The use of MASER beam modulation to cause cellular necrosis in discrete brain targets for the treatment of intrinsic or metastatic brain neoplasms, epilepsy, arteriovenous malformations, and essential tremor.

What is claimed is:

1. A method of activity mapping using a MASER diffraction-limited interferometer, the method comprising the steps of:

emitting a beam of coherent MASER radiation by an emitter array and passing the emitted beam through a collimator;

splitting of the collimated MASER beam into a probe beam and a reference beam;

passing the probe beam through a head and a brain, spinal column and spinal cord, or other biological parts of a patient to create a post-engagement beam while simultaneously passing the reference beam through a uniform substance resulting in a delay of the reference beam similar to that of the probe beam caused by the head or other body part of the patient in order to generate a lagged reference beam;

combining the lagged reference beam and the post-engagement beam to create a convolved beam characterized by a time-shifting interference pattern;

detecting the time-shifting interference pattern in the convolved beam by a detector array;

de-convolving the interference pattern to quantify changes in phase, modulation, amplitude, and lag between the post-engagement beam and the lagged reference beam to generate a holographic perspective map;

populating a voxel map with the processed data for the slice of time from the given holographic perspective and repeating this step from multiple holographic perspectives in accordance with a synthetic aperture algorithm;

associating the voxel map with an image generated by an MRI or CT scan to create a three-dimensional energy activity map for the given time slice.

2. The method in claim 1 wherein the activity map identifies one or more of the following: inferred changes to the conformation and energy states of saccharides including glucose, peptide neurotransmitters including glutamate, acetylcholine, GABA, dopamine, or serotonin, trans-membrane ion channels and receptors including voltage-gated ion channels, ligand-gated ion channels, or G-protein coupled receptors, reflecting changes in membrane potential or firing of action potentials in neuronal dendrites, soma, and axons.

3. The method in claim 1 wherein the activity map identifies changes associated with the neuronal firing of action potentials.

4. The method in claim 1 wherein the activity map identifies increases or decreases in glucose metabolism.

5. The method in claim 1 wherein the activity map identifies activity levels or conformational changes of g-protein coupled receptors.

6. The method in claim 1 wherein the activity map identifies activity levels or conformational changes of ligand-gated glutamate receptors.

7. The method in claim 1 wherein the activity map identifies activity levels or conformational changes in voltage-gated ion channels.

8. The method in claim 1, wherein the activity map identifies the activity or conformational changes of IL-13RA2 receptor and EphA2 receptors that are overexpressed in primary brain tumors.

* * * * *